(12) United States Patent
Yamamoto et al.

(10) Patent No.: US 7,485,697 B2
(45) Date of Patent: Feb. 3, 2009

(54) SOLUBLE RAGE PROTEIN

(75) Inventors: Hiroshi Yamamoto, Kanazawa (JP);
Hideto Yonekura, Kanazawa (JP);
Yasuhiko Yamamoto, Takaoka (JP);
Shigeru Sakurai, Kanazawa (JP);
Takuo Watanabe, Kanazawa (JP)

(73) Assignee: Japan as Represented by President of Kanazawa University, Ishikawa (JP)

( * ) Notice: Subject to any disclaimer, the term of this patent is extended or adjusted under 35 U.S.C. 154(b) by 598 days.

(21) Appl. No.: 10/472,507

(22) PCT Filed: Mar. 19, 2002

(86) PCT No.: PCT/JP02/02623

§ 371 (c)(1),
(2), (4) Date: May 12, 2004

(87) PCT Pub. No.: WO02/074805

PCT Pub. Date: Sep. 26, 2002

(65) Prior Publication Data

US 2005/0033017 A1    Feb. 10, 2005

(30) Foreign Application Priority Data

Mar. 19, 2001  (JP)  ............... 2001-078409
Aug. 10, 2001  (JP)  ............... 2001-243114
Feb. 25, 2002  (JP)  ............... 2002-048182

(51) Int. Cl.
*C07K 14/705*   (2006.01)
*C07H 21/04*    (2006.01)
*C12P 21/02*    (2006.01)
*G01N 33/53*    (2006.01)
*C12Q 1/68*     (2006.01)

(52) U.S. Cl. .................... 530/350; 435/6; 435/7.1; 435/69.1; 435/252.3; 435/254.11; 435/320.1; 435/325; 536/23.5

(58) Field of Classification Search ............... None
See application file for complete search history.

(56) References Cited

FOREIGN PATENT DOCUMENTS

| WO | 97/39121    | 10/1997 |
|----|-------------|---------|
| WO | 97/39125    | 10/1997 |
| WO | 99/07402 A1 | 2/1999  |
| WO | 00/20458 A1 | 4/2000  |
| WO | 01/92892 A2 | 12/2001 |

OTHER PUBLICATIONS

Neeper et al. Cloning and expression of a cell surface receptor for advanced glycosylation end products of proteins. J Biol Chem. Jul. 25, 1992;267(21):14998-5004.*

Malherbe et al, "cDNA cloning of a novel secreted isoform of the human receptor for advanced glycation end products and characterization of cells co-expressing cell-surface scavenger receptors and Swedish mutant amyloid precursor protein", *Molecular Brain Research*, vol. 71, pp. 159-170 (1999).

Giron et al, "Sequencing of Two Alternatively Spliced mRNAs Corresponding to the Extrancellular Domain of the Rat Receptor for Advanced Glycosylation End Products (RAGE)", *Biochemical and Biophysical Research Communications*, vol. 251, No. 1, pp. 230-234 (1998).

Abstract of Prevost et al, "Human Rage GLY82SER dimorphism and HLA class II DRB1-DQA1-DQB1 haplotypes in type 1 diabetes", *Eur. J. Immunogenet*, vol. 26, No. 5, pp. 343-348 (1999), Database Medline, National Library of Medicine, PMID: 10553500.

Fajardy et al, "Rage main exon 3 polymorphism and HLA class II inheritance in type 1 diabetic families", *Human Immunology*, vol. 61, suppl. 1, p. S75 (2000), Database Biosis Previews on Dialog, Biosis, No. 200000170507.

Lalla et al, "Blockade of Rage suppresses periodontitis-associated bone loss in diabetic mice", *J. Clin. Invest.*, vol. 105, No. 8, pp. 1117-1124 (Apr. 2000).

Tanaka et al, The receptor for advanced glycation end products is induced by the glycation products themselves and tumor necrosis factor-alpha through nuclear factor-kappa β, and by 17 beta-estradiol through Sp-1 in human vascular endothelial cells, *J. Biol. Chem.*, vol. 275, No. 33, pp. 25781-25790 (Aug. 2000).

Park et al., "Suppression of accelerated diabetic atherosclerosis by the soluble receptor for advanced glycation endproducts," *Nature Medicine*, Sep. 1998, pp. 1025-1031, vol. 4, No. 9, Nature Publishing Co., US.

Yonekura et al., "Novel splice variants of the receptor for advanced glycation end-products expressed in human vascular endothelial cells and pericytes, and their putative roles in diabetes-induced vascular injury," *Biochem. J.*, Mar. 15, 2003, pp. 1097-1109, vol. 370, Biochemical Society.

* cited by examiner

*Primary Examiner*—Elizabeth C. Kemmerer
*Assistant Examiner*—Gregory S. Emch
(74) *Attorney, Agent, or Firm*—Buchanan, Ingersoll & Rooney, P.C.

(57) ABSTRACT

The object of this invention is to elucidate the factors involved in the regulation of AGE (advanced glycation endproducts, which are produced in a living body accompanied with diabetes and aging) and RAGE (the receptor for AGE), in order to facilitate investigation on the biological activities, physiological phenomenon and diseases related to AGE and RAGE. Plural molecular species are known to exist for RAGE, and among such molecular species, soluble RAGE exhibits the activity to modulate interaction between AGE and transmembrane-type RAGE. Using this soluble RAGE or a nucleic acid encoding it, the soluble RAGE can be measured, in addition, investigation on various physiological phenomenon, biological activities, and diseases related to interaction between AGE and RAGE can be performed to facilitate development a medicine having further efficacy.

1 Claim, 10 Drawing Sheets
(5 of 10 Drawing Sheet(s) Filed in Color)

FIG. 2

```
fullRAGE.nuc    :GCCAGGACCCTGGAAGGAAGCAGGATGGCAGCCGGAACAGCAGTTGGAGCCTGGGTGCTG
US5864018.nuc   :----------------------ATGGCAGCCGGAACAGCAGTTGGAGCCTGGGTGCTG
solubleRAGE.nuc :GCCAGGACCCTGGAAGGAAGCAGGATGGCAGCCGGAACAGCAGTTGGAGCCTGGGTGCTG
                 .......................*********************************** fullRAGE.nuc    :GTCCTCAGTCTGTGGGGGGCAGTAGTAGGTGCTCAAAACATCACAGCCCGGATTGGCGAG
US5864018.nuc   :GTCCTCAGTCTGTGGGGGGCAGTAGTAGGTGCTCAAAACATCACAGCCCGGATTGGCGAG
solubleRAGE.nuc :GTCCTCAGTCTGTGGGGGGCAGTAGTAGGTGCTCAAAACATCACAGCCCGGATTGGCGAG
                 ************************************************************ fullRAGE.nuc    :CCACTGGTGCTGAAGTGTAAGGGGGCCCCCAAGAAACCACCCCAGCGGCTGGAATGGAAA
US5864018.nuc   :CCACTGGTGCTGAAGTGTAAGGGGGCCCCCAAGAAACCACCCCAGCGGCTGGAATGGAAA
solubleRAGE.nuc :CCACTGGTGCTGAAGTGTAAGGGGGCCCCCAAGAAACCACCCCAGCGGCTGGAATGGAAA
                 ************************************************************ fullRAGE.nuc    :CTGAACACAGGCCGGACAGAAGCTTGGAAGGTCCTGTCTCCCCAGGGAGGAGGCCCCTGG
US5864018.nuc   :CTGAACACAGGCCGGACAGAAGCTTGGAAGGTCCTGTCTCCCCAGGGAGGAGGCCCCTGG
solubleRAGE.nuc :CTGAACACAGGCCGGACAGAAGCTTGGAAGGTCCTGTCTCCCCAGGGAGGAGGCCCCTGG
                 ************************************************************ fullRAGE.nuc    :GACAGTGTGGCTCGTGTCCTTCCCAACGGCTCCCTCTTCCTTCCGGCTGTCGGGATCCAG
US5864018.nuc   :GACAGTGTGGCTCGTGTCCTTCCCAACGGCTCCCTCTTCCTTCCGGCTGTCGGGATCCAG
solubleRAGE.nuc :GACAGTGTGGCTCGTGTCCTTCCCAACGGCTCCCTCTTCCTTCCGGCTGTCGGGATCCAG
                 ************************************************************ fullRAGE.nuc    GATGAGGGGATTTTCCGGTGCCAGGCAATGAACAGGAATGGAAAGGAGACCAAGTCCAAC
US5864018.nuc   GATGAGGGGATTTTCCGGTGCAGGGCAATGAACAGGAATGGAAAGGAGACCAAGTCCAAC
solubleRAGE.nuc GATGAGGGGATTTTCCGGTGCCAGGCAATGAACAGGAATGGAAAGGAGACCAAGTCCAAC
                ******************  ************************************ fullRAGE.nuc    :TACCGAGTCCGTGTCTACCAGATTCCTGGGAAGCCAGAAATTGTAGATTCTGCCTCTGAA
US5864018.nuc   :TACCGAGTCCGTGTCTACCAGATTCCTGGGAAGCCAGAAATTGTAGATTCTGCCTCTGAA
solubleRAGE.nuc :TACCGAGTCCGTGTCTACCAGATTCCTGGGAAGCCAGAAATTGTAGATTCTGCCTCTGAA
                 ************************************************************ fullRAGE.nuc    CTCACGGCTGGTGTTCCCAATAAGGTGGGGACATGTGTGTCAGAGGGAAGCTACCCTGCA
US5864018.nuc   CTCACGGCTGGTGTTCCCAATAAGGTGGGGACATGTGTGTCAGAGGGAAGCTACCCTGCA
solubleRAGE.nuc CTCACGGCTGGTGTTCCCAATAAGGTGGGGACATGTGTGTCAGAGGGAAGCTACCCTGCA
                ************************************************************
```

FIG. 3

```
fullRAGE.nuc      :GGGACTCTTAGCTGGCACTTGGATGGGAAGCCCCTGGTGCCTAATGAGAAGGGAGTATCT
US5864018.nuc     :GGGACTCTTAGCTGGCACTTGGATGGGAAGCCCCTGGTGCCTAATGAGAAGGGAGTATCT
solubleRAGE.nuc   :GGGACTCTTAGCTGGCACTTGGATGGGAAGCCCCTGGTGCCTAATGAGAAGGGAGTATCT
                   ************************************************************ fullRAGE.nuc      :GTGAAGGAACAGACCAGGAGACACCCTGAGACAGGGCTCTTCACACTGCAGTCGGAGCTA
US5864018.nuc     :GTGAAGGAACAGACCAGGAGACACCCTGAGACAGGGCTCTTCACACTGCAGTCGGAGCTA
solubleRAGE.nuc   :GTGAAGGAACAGACCAGGAGACACCCTGAGACAGGGCTCTTCACACTGCAGTCGGAGCTA
                   ************************************************************ fullRAGE.nuc      :ATGGTGACCCCAGCCCGGGGAGGAGATCCCCGTCCCACCTTCTCCTGTAGCTTCAGCCCA
US5864018.nuc     :ATGGTGACCCCAGCCCGGGGAGGAGATCCCCGTCCCACCTTCTCCTGTAGCTTCAGCCCA
solubleRAGE.nuc   :ATGGTGACCCCAGCCCGGGGAGGAGATCCCCGTCCCACCTTCTCCTGTAGCTTCAGCCCA
                   ************************************************************ fullRAGE.nuc      :GGCCTTCCCCGACACCGGGCCTTGCGCACAGCCCCCATCCAGCCCCGTGTCTGGGAGCCT
US5864018.nuc     :GGCCTTCCCCGACACCGGGCCTTGCGCACAGCCCCCATCCAGCCCCGTGTCTGGGAGCCT
solubleRAGE.nuc   :GGCCTTCCCCGACACCGGGCCTTGCGCACAGCCCCCATCCAGCCCCGTGTCTGGGAGCCT
                   ************************************************************ fullRAGE.nuc      :GTGCCTCTGGAGGAGGTCCAATTGGTGGTGGAGCCAGAAGGTGGAGCAGTAGCTCCTGGT
US5864018.nuc     :GTGCCTCTGGAGGAGGTCCAATTGGTGGTGGAGCCAGAAGGTGGAGCAGTAGCTCCTGGT
solubleRAGE.nuc   :GTGCCTCTGGAGGAGGTCCAATTGGTGGTGGAGCCAGAAGGTGGAGCAGTAGCTCCTGGT
                   ************************************************************ fullRAGE.nuc      :GGAACCGTAACCCTGACCTGTGAAGTCCCTGCCCAGCCCTCTCCTCAAATCCACTGGATG
US5864018.nuc     :GGAACCGTAACCCTGACCTGTGAAGTCCCTGCCCAGCCCTCTCCTCAAATCCACTGGATG
solubleRAGE.nuc   :GGAACCGTAACCCTGACCTGTGAAGTCCCTGCCCAGCCCTCTCCTCAAATCCACTGGATG
                   ************************************************************ fullRAGE.nuc      :AAGGATGGTGTGCCCTTGCCCCTTCCCCCCAGCCCTGTGCTGATCCTCCCTGAGATAGGG
US5864018.nuc     :AAGGATGGTGTGCCCTTGCCCCTTCCCCCCAGCCCTGTGCTGATCCTCCCTGAGATAGGG
solubleRAGE.nuc   :AAGGATGGTGTGCCCTTGCCCCTTCCCCCCAGCCCTGTGCTGATCCTCCCTGAGATAGGG
                   ************************************************************ fullRAGE.nuc      :CCTCAGGACCAGGGAACCTACAGCTGTGTGGCCACCCATTCCAGCCACGGGCCCCAGGAA
US5864018.nuc     :CCTCAGGACCAGGGAACCTACAGCTGTGTGGCCACCCATTCCAGCCACGGGCCCCAGGAA
solubleRAGE.nuc   :CCTCAGGACCAGGGAACCTACAGCTGTGTGGCCACCCATTCCAGCCACGGGCCCCAGGAA
                   ************************************************************
```

FIG. 4

```
fullRAGE.nuc    :AGCCGTGCTGTCAGCATCAGCATCATCGAACCAGGCGAGGAGGGGCCAACTGCAG-----
US5864018.nuc   :AGCCGTGCTGTCAGCATCAGCATCATCGAACCAGGCGAGGAGGGGCCAACTGCAG-----
solubleRAGE.nuc :AGCCGTGCTGTCAGCATCAGCATCATCGAACCAGGCGAGGAGGGGCCAACTGCAGGTGAG
                 ************************************************************ fullRAGE.nuc    :------------------------------------------------------------
US5864018.nuc   :------------------------------------------------------------
solubleRAGE.nuc :GGGTTTGATAAAGTCAGGGAAGCAGAAGATAGCCCCCAACACATGTGACTGGGGGGATGG fullRAGE.nuc    :----------------GCTCTGTGGGAGGATCAGGGCTGGGAACTCTAGCCCTGGCCCT
US5864018.nuc   :----------------GCTCTGTGGGAGGATCAGGGCTGGGAACTTGA-----------
solubleRAGE.nuc :TCAACAAGAAAGGAATG------------------------------------------
                                 . . . . . . . . . . . . . . . . . . . . . . . . . . . . .

fullRAGE.nuc    :GGGGATCCTGGGAGGCCTGGGGACAGCCGCCCTGCTCATTGGGGTCATCTTGTGGCAAAG
US5864018.nuc   :------------------------------------------------------------
solubleRAGE.nuc :------------------------------------------------------------ fullRAGE.nuc    :GCGGCAACGCCGAGGAGAGGAGAGGAAGGCCCCAGAAAACCAGGAGGAAGAGGAGGAGCG
US5864018.nuc   :------------------------------------------------------------
solubleRAGE.nuc :-----------------------GAAGGCCCCAGAAAACCAGGAGGAAGAGGAGGAGCG
                                         . . . . . . . . . . . . . . . . . . . . . . . . . . . . . . . . .

fullRAGE.nuc    :TGCAGAACTGAATCAGTCGGAGGAACCTGAGGCAGGCGAGAGTAGTACTGGAGGGCCTTG
US5864018.nuc   :------------------------------------------------------------
solubleRAGE.nuc :TGCAGAACTGAATCAGTCGGAGGAACCTGAGGCAGGCGAGAGTAGTACTGGAGGGCCTTG
                 . . . . . . . . . . . . . . . . . . . . . . . . . . . . . . . . . . . . . . . . . . .

fullRAGE.nuc    :AGGGGCCCACAGACAGATCCCATCCATCAG
US5864018.nuc   :------------------------------
solubleRAGE.nuc :AGGGGCCCACAGACAGATCCCATCCATCAG
                 . . . . . . . . . . . . . . . . . . . . . . . . . . . . . .
```

FIG. 5

```
fullRAGE.ptn      :MAAGTAVGAWVLVLSLWGAVVGAQNITARIGEPLVLKCKGAPKKPPQRLEWKLNTGRTEA
US5864018.ptn     :MAAGTAVGAWVLVLSLWGAVVGAQNITARIGEPLVLKCKGAPKKPPQRLEWKLNTGRTEA
solubleRAGE.ptn   :MAAGTAVGAWVLVLSLWGAVVGAQNITARIGEPLVLKCKGAPKKPPQRLEWKLNTGRTEA
                   ************************************************************ fullRAGE.ptn      :WKVLSPQGGGPWDSVARVLPNGSLFLPAVGIQDEGIFRCQAMNRNGKETKSNYRVRVYQI
US5864018.ptn     :WKVLSPQGGGPWDSVARVLPNGSLFLPAVGIQDEGIFRCRAMNRNGKETKSNYRVRVYQI
solubleRAGE.ptn   :WKVLSPQGGGPWDSVARVLPNGSLFLPAVGIQDEGIFRCQAMNRNGKETKSNYRVRVYQI
                   ************************************* ****************** fullRAGE.ptn      :PGKPEIVDSASELTAGVPNKVGTCVSEGSYPAGTLSWHLDGKPLVPNEKGVSVKEQTRRH
US5864018.ptn     :PGKPEIVDSASELTAGVPNKVGTCVSEGSYPAGTLSWHLDGKPLVPNEKGVSVKEQTRRH
solubleRAGE.ptn   :PGKPEIVDSASELTAGVPNKVGTCVSEGSYPAGTLSWHLDGKPLVPNEKGVSVKEQTRRH
                   ************************************************************ fullRAGE.ptn      :PETGLFTLQSELMVTPARGGDPRPTFSCSFSPGLPRHRALRTAPIQPRVWEPVPLEEVQL
US5864018.ptn     :PETGLFTLQSELMVTPARGGDPRPTFSCSFSPGLPRHRALRTAPIQPRVWEPVPLEEVQL
solubleRAGE.ptn   :PETGLFTLQSELMVTPARGGDPRPTFSCSFSPGLPRHRALRTAPIQPRVWEPVPLEEVQL
                   ************************************************************ fullRAGE.ptn      :VVEPEGGAVAPGGTVTLTCEVPAQPSPQIHWMKDGVPLPLPPSPVLILPEIGPQDQGTYS
US5864018.ptn     :VVEPEGGAVAPGGTVTLTCEVPAQPSPQIHWMKDGVPLPLPPSPVLILPEIGPQDQGTYS
solubleRAGE.ptn   :VVEPEGGAVAPGGTVTLTCEVPAQPSPQIHWMKDGVPLPLPPSPVLILPEIGPQDQGTYS
                   ************************************************************ fullRAGE.ptn      : CVATHSSHGPQESRAVSISIIEPGEEGPTAG---------------SVGGSGLGTLALA
US5864018.ptn     : CVATHSSHGPQESRAVSISIIEPGEEGPTAG---------------SVGGSGLGTL
solubleRAGE.ptn   : CVATHSSHGPQESRAVSISIIEPGEEGPTAGEGFDKVREAEDSPQHM
                    ******************************* fullRAGE.ptn   345:LGILGGLGTAALLIGVILWQRRQRRGEERKAPENQEEEEERAELNQSEEPEAGESSTGGP
```

FIG. 7
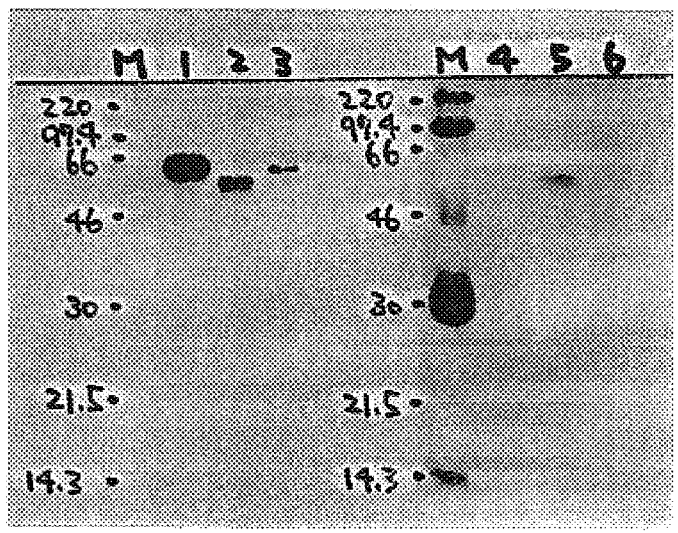
Positive cont.      269-4C9
Polyclonal Ab      Monoclonal Ab
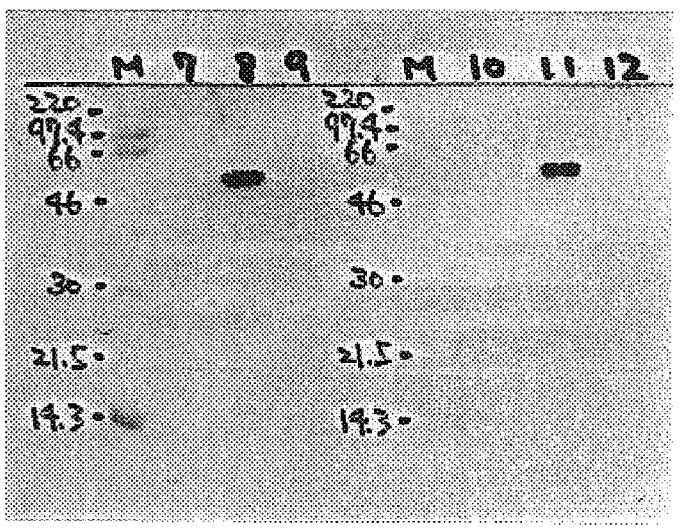 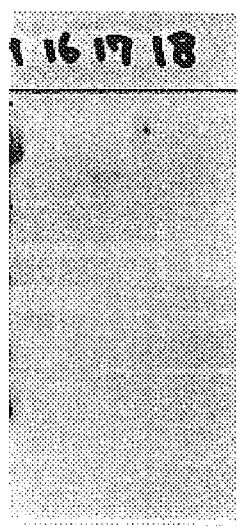
269-6B12      269-9C2      269-1D10
Monoclonal Ab      Monoclonal Ab      Monoclonal Ab 1: 269-1D10
2: 269-9C2
3: Normal mouse immunoglobulin

SEQUENCE LISTING

```
<160> NUMBER OF SEQ ID NOS: 7

<210> SEQ ID NO 1
<211> LENGTH: 1223
<212> TYPE: DNA
<213> ORGANISM: Homo sapiens
<220> FEATURE:
<221> NAME/KEY: CDS
<222> LOCATION: (25)...(1068)

<400> SEQUENCE: 1
gccaggaccc tggaaggaag cagg atg gca gcc gga aca gca gtt gga gcc        51
                           Met Ala Ala Gly Thr Ala Val Gly Ala
                            1               5 tgg gtg ctg gtc ctc agt ctg tgg ggg gca gta gta ggt gct caa aac       99
Trp Val Leu Val Leu Ser Leu Trp Gly Ala Val Val Gly Ala Gln Asn
 10              15                  20                  25 atc aca gcc cgg att ggc gag cca ctg gtg ctg aag tgt aag ggg gcc      147
Ile Thr Ala Arg Ile Gly Glu Pro Leu Val Leu Lys Cys Lys Gly Ala
                 30                  35                  40 ccc aag aaa cca ccc cag cgg ctg gaa tgg aaa ctg aac aca ggc cgg      195
Pro Lys Lys Pro Pro Gln Arg Leu Glu Trp Lys Leu Asn Thr Gly Arg
             45                  50                  55 aca gaa gct tgg aag gtc ctg tct ccc cag gga gga ggc ccc tgg gac      243
Thr Glu Ala Trp Lys Val Leu Ser Pro Gln Gly Gly Gly Pro Trp Asp
         60                  65                  70 agt gtg gct cgt gtc ctt ccc aac ggc tcc ctc ttc ctt ccg gct gtc      291
Ser Val Ala Arg Val Leu Pro Asn Gly Ser Leu Phe Leu Pro Ala Val
     75                  80                  85 ggg atc cag gat gag ggg att ttc cgg tgc cag gca atg aac agg aat      339
```

| | | | | | | | | | | | | | | | | |
|---|---|---|---|---|---|---|---|---|---|---|---|---|---|---|---|---|
| Gly | Ile | Gln | Asp | Glu | Gly | Ile | Phe | Arg | Cys | Gln | Ala | Met | Asn | Arg | Asn | |
| | 90 | | | | 95 | | | | 100 | | | | | 105 | | |

```
gga aag gag acc aag tcc aac tac cga gtc cgt gtc tac cag att cct      387
Gly Lys Glu Thr Lys Ser Asn Tyr Arg Val Arg Val Tyr Gln Ile Pro
            110                 115                 120 ggg aag cca gaa att gta gat tct gcc tct gaa ctc acg gct ggt gtt      435
Gly Lys Pro Glu Ile Val Asp Ser Ala Ser Glu Leu Thr Ala Gly Val
            125                 130                 135 ccc aat aag gtg ggg aca tgt gtg tca gag gga agc tac cct gca ggg      483
Pro Asn Lys Val Gly Thr Cys Val Ser Glu Gly Ser Tyr Pro Ala Gly
            140                 145                 150 act ctt agc tgg cac ttg gat ggg aag ccc ctg gtg cct aat gag aag      531
Thr Leu Ser Trp His Leu Asp Gly Lys Pro Leu Val Pro Asn Glu Lys
            155                 160                 165 gga gta tct gtg aag gaa cag acc agg aga cac cct gag aca ggg ctc      579
Gly Val Ser Val Lys Glu Gln Thr Arg Arg His Pro Glu Thr Gly Leu
170             175                 180                 185 ttc aca ctg cag tcg gag cta atg gtg acc cca gcc cgg gga gga gat      627
Phe Thr Leu Gln Ser Glu Leu Met Val Thr Pro Ala Arg Gly Gly Asp
            190                 195                 200 ccc cgt ccc acc ttc tcc tgt agc ttc agc cca ggc ctt ccc cga cac      675
Pro Arg Pro Thr Phe Ser Cys Ser Phe Ser Pro Gly Leu Pro Arg His
            205                 210                 215 cgg gcc ttg cgc aca gcc ccc atc cag ccc cgt gtc tgg gag cct gtg      723
Arg Ala Leu Arg Thr Ala Pro Ile Gln Pro Arg Val Trp Glu Pro Val
            220                 225                 230 cct ctg gag gag gtc caa ttg gtg gtg gag cca gaa ggt gga gca gta      771
Pro Leu Glu Glu Val Gln Leu Val Val Glu Pro Glu Gly Gly Ala Val
235                 240                 245 gct cct ggt gga acc gta acc ctg acc tgt gaa gtc cct gcc cag ccc      819
Ala Pro Gly Gly Thr Val Thr Leu Thr Cys Glu Val Pro Ala Gln Pro
250                 255                 260                 265 tct cct caa atc cac tgg atg aag gat ggt gtg ccc ttg ccc ctt ccc      867
Ser Pro Gln Ile His Trp Met Lys Asp Gly Val Pro Leu Pro Leu Pro
            270                 275                 280 ccc agc cct gtg ctg atc ctc cct gag ata ggg cct cag gac cag gga      915
Pro Ser Pro Val Leu Ile Leu Pro Glu Ile Gly Pro Gln Asp Gln Gly
            285                 290                 295 acc tac agc tgt gtg gcc acc cat tcc agc cac ggg ccc cag gaa agc      963
Thr Tyr Ser Cys Val Ala Thr His Ser Ser His Gly Pro Gln Glu Ser
            300                 305                 310 cgt gct gtc agc atc agc atc atc gaa cca ggc gag gag ggg cca act     1011
Arg Ala Val Ser Ile Ser Ile Ile Glu Pro Gly Glu Glu Gly Pro Thr
            315                 320                 325 gca ggt gag ggg ttt gat aaa gtc agg gaa gca gaa gat agc ccc caa     1059
Ala Gly Glu Gly Phe Asp Lys Val Arg Glu Ala Glu Asp Ser Pro Gln
330                 335                 340                 345 cac atg tga ctgggggat ggtcaacaag aaaggaatgg aaggccccag              1108
His Met * aaaaccagga ggaagaggag gagcgtgcag aactgaatca gtcggaggaa cctgaggcag   1168
gcgagagtag tactggaggg ccttgagggg cccacagaca gatcccatcc atcag        1223

<210> SEQ ID NO 2
<211> LENGTH: 347
<212> TYPE: PRT
<213> ORGANISM: Homo sapiens

<400> SEQUENCE: 2

Met Ala Ala Gly Thr Ala Val Gly Ala Trp Val Leu Val Leu Ser Leu
```

```
            1               5                  10                 15

Trp Gly Ala Val Val Gly Ala Gln Asn Ile Thr Ala Arg Ile Gly Glu
                        20                 25                 30

Pro Leu Val Leu Lys Cys Lys Gly Ala Pro Lys Lys Pro Pro Gln Arg
                        35                 40                 45

Leu Glu Trp Lys Leu Asn Thr Gly Arg Thr Glu Ala Trp Lys Val Leu
                        50                 55                 60

Ser Pro Gln Gly Gly Pro Trp Asp Ser Val Ala Arg Val Leu Pro
        65                      70                 75                 80

Asn Gly Ser Leu Phe Leu Pro Ala Val Gly Ile Gln Asp Glu Gly Ile
                            85                 90                 95

Phe Arg Cys Gln Ala Met Asn Arg Asn Gly Lys Glu Thr Lys Ser Asn
                        100                105                110

Tyr Arg Val Arg Val Tyr Gln Ile Pro Gly Lys Pro Glu Ile Val Asp
                        115                120                125

Ser Ala Ser Glu Leu Thr Ala Gly Val Pro Asn Lys Val Gly Thr Cys
                        130                135                140

Val Ser Glu Gly Ser Tyr Pro Ala Gly Thr Leu Ser Trp His Leu Asp
        145                     150                155                160

Gly Lys Pro Leu Val Pro Asn Glu Lys Gly Val Ser Val Lys Glu Gln
                            165                170                175

Thr Arg Arg His Pro Glu Thr Gly Leu Phe Thr Leu Gln Ser Glu Leu
                        180                185                190

Met Val Thr Pro Ala Arg Gly Gly Asp Pro Arg Pro Thr Phe Ser Cys
                        195                200                205

Ser Phe Ser Pro Gly Leu Pro Arg His Arg Ala Leu Arg Thr Ala Pro
                        210                215                220

Ile Gln Pro Arg Val Trp Glu Pro Val Pro Leu Glu Glu Val Gln Leu
        225                     230                235                240

Val Val Glu Pro Glu Gly Gly Ala Val Ala Pro Gly Gly Thr Val Thr
                            245                250                255

Leu Thr Cys Glu Val Pro Ala Gln Pro Ser Pro Gln Ile His Trp Met
                        260                265                270

Lys Asp Gly Val Pro Leu Pro Leu Pro Pro Ser Pro Val Leu Ile Leu
                        275                280                285

Pro Glu Ile Gly Pro Gln Asp Gln Gly Thr Tyr Ser Cys Val Ala Thr
                        290                295                300

His Ser Ser His Gly Pro Gln Glu Ser Arg Ala Val Ser Ile Ser Ile
        305                     310                315                320

Ile Glu Pro Gly Glu Glu Gly Pro Thr Ala Gly Glu Gly Phe Asp Lys
                            325                330                335

Val Arg Glu Ala Glu Asp Ser Pro Gln His Met
                        340                345

<210> SEQ ID NO 3
<211> LENGTH: 22
<212> TYPE: DNA
<213> ORGANISM: Artificial Sequence
<220> FEATURE:
<223> OTHER INFORMATION: Oligonucleotide to act as a primer for PCR

<400> SEQUENCE: 3
gccaggaccc tggaaggaag ca                                           22

<210> SEQ ID NO 4
```

```
<211> LENGTH: 23
<212> TYPE: DNA
<213> ORGANISM: Artificial Sequence
<220> FEATURE:
<223> OTHER INFORMATION: Oligonucleotide to act as a primer for PCR

<400> SEQUENCE: 4
ctgatggatg ggatctgtct gtg                                          23

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide to act as a primer for PCR

<400> SEQUENCE: 5
gagaattcgc caggaccctg gaaggaagca                                   30

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide to act as a primer for PCR

<400> SEQUENCE: 6
gatctagaga ttgttgacca tccccccag                                    29

<210> SEQ ID NO 7
<211> LENGTH: 17
<212> TYPE: PRT
<213> ORGANISM: Artificial Sequence
<220> FEATURE:
<223> OTHER INFORMATION: Designed peptide to act as an immuogen

<400> SEQUENCE: 7

Cys Glu Gly Phe Asp Lys Val Arg Glu Ala Glu Asp Ser Pro Gln His
 1               5                  10                  15
Met
```

SOLUBLE RAGE PROTEIN

BACKGROUND OF THE INVENTION

1. Field of the Invention

The present invention relates to a human soluble RAGE (receptor for advanced glycation endproducts) polypeptide, specifically to a native soluble RAGE polypeptide having a characteristic C terminal sequence, a nucleic acid encoding the polypeptide, a recombinant vector containing the nucleic acid, and a transformed cell, as well as use of them including screening, assay, diagnosis and treatment.

2. Description of the Related Art

Recently, the number of diabetic patients in Japan is steadily increasing, and according to the statistics published in 1998 by the Ministry of Health and Welfare of Japanese Government, the number of diabetic patients was estimated to be six millions and nine hundreds of thousands, and if sub-clinical patients were included, the number would amount to 14 millions. The factor that directly affects life duration and quality of life of a diabetic patient is systemic derangement in the vascular system secondarily caused by hyperglycemia (i.e. vascular complications), not primary malfunction resulting from deficiency in the insulin supply. In view of this, the mechanism involved in occurrence of such vascular complications should be elucidated and a strategy to conquer such complications based on the knowledge should be constructed, as these are significant problems which need urgent resolution.

The present inventors have been studied on the environmental and genetic factors involved in the development and progression of diabetic complications. The inventors performed in-vitro experiments on cultured vascular cells as well as in-vivo experiments on transgenic animals. Through such experiments, the inventors demonstrated that the environmental factors are mainly accounted for by advanced glycation endproducts (AGE), which increasingly accumulate with the development of diabetes. Moreover, the inventors demonstrated that the genetic factors are significantly related to the genes encoding RAGE which specifically recognize and bind to AGE, as well as genes existing downstream thereof encoding signal molecules and effector molecules(J. Biol. Chem., 272, 8723-8730, 1997; 275, 27781-25790, 2000; and J. Clin. Invest., 108, 261-268, 2001).

It has been predicted that there may be a genetic factor responsible for the susceptibility/resistance of vascular complications in diabetic patients, but identification of such a factor has not been performed yet.

It has been suggested that AGE are involved in the development of complications associated with diabetes and aging. Indeed, it was demonstrated that AGE bind to the receptors present on the surface of monocytes/macrophages, neurons, smooth muscle cells and vascular endothelial cells. It is thought that AGE interacts with these receptors, thereby exerting various physiological and biological actions to the living organisms and cells. For example, AGE act to enhance proliferation of vascular endothelial cells, and in addition, AGE are involved in enhancement of vascular permeability, and of formation of thrombus. As to effect of AGE on monocytes/macrophages, the release of cytokines from those cells would be enhanced, and release of various factors involved in cell proliferation and migration and synthesis of matrix would be also increased. It is further suspected that AGE might be involved in the inflammatory response observed in the wall of vessels.

SUMMARY OF THE INVENTION

Accumulating evidence indicates that AGE exert various physiological and biological effects on bodies and cells by binding to its receptor, which will lead to development and progression of various diseases. Based on these findings, it has been expected to find substances that could affect interaction between AGE and their receptor, thereby enabling application of such a substance for elucidation, prevention, diagnosis and treatment of various diseases.

Quite recently, Yamamoto (one of the inventors) revealed that a RAGE protein expressed on human vascular cell has molecular diversity, which may be ascribed to alternative splicing of RAGE gene transcription products (see FIG. 1). According to the finding, one of the major molecular species is the soluble RAGE protein, which is secreted out of the cell because it lacks its transmembrane domain. However, the protein has an extracellular domain identical with the corresponding domain of a matured, membrane-binding type protein, and thus it can also bind to AGE to capture them. Indeed, recombinant human soluble RAGE protein was purified, and the purified protein was revealed to bind to various AGE fractions with high affinity, when binding assay with AGE ligands were performed. If expression of the gene encoding the soluble RAGE protein has diversity among individuals, diabetic patients showing high blood level of the protein would be resistant to vascular complications whereas other patients showing low blood level of the protein would be comparatively susceptible to vascular complications.

The present invention provides a novel RAGE polypeptide, a nucleic acid comprising a base sequence encoding the polypeptide, a recombinant vector containing the nucleic acid, and a transformant containing the nucleic acid or the vector, as well as use of them for the purpose of screening, diagnosis and treatment. The present invention provides a technique for genetic diagnosis in relation to the soluble RAGE, for example, genetic diagnosis is performed on expression and polymorphism of the novel soluble RAGE protein, which is assumed to be a factor determining the resistance/susceptibility of a patient to diabetic complications, cancer and Alzheimer disease. Moreover, a technique for gene therapy is provided to reduce the risk of said diseases and related diseases based on the result of the diagnosis.

The present invention provides the inventions of following [1] to [22].

[1] A polypeptide described in any one of the following (1) to (4) or a salt thereof:
(1) (A) a soluble RAGE polypeptide, or
  (B) a polypeptide selected from the group consisting of the following or a salt thereof:
    (1) (i) a polypeptide having at least 60% homology with the amino acid sequence described in the ID No. 2 of the sequence listing, and;
    (ii) (a) a polypeptide deleted of the transmembrane domain of the membrane-bound type RAGE protein and having a serial amino acid sequence comprising at least 1 to 16 amino acid residues out of $Glu^{332}$ to $Met^{347}$ of the amino acid sequence described in the SEQ ID No. 2 of the sequence listing at its C terminal;
    (b) a polypeptide having a serial amino acid sequence comprising at least 1 to 117 amino acid residues out of $Met^1$ to $Val^{117}$ at the N terminal of the amino acid sequence described in the SEQ ID No. 2 of the sequence listing; deleted with the transmembrane domain of the membrane-bound type RAGE protein; and having a serial amino acid sequence comprising at least 1 to 16 amino acid residues out of $Glu^{332}$ to $Met^{347}$ of the amino acid sequence described in the SEQ ID No. 2 of the sequence listing at its C terminal;

(c) a polypeptide having a serial amino acid sequence comprising at least 1 to 117 amino acid residues out of a serial amino acid sequence comprising 1 to 117 amino acid residues at the N terminal of the amino acid sequence of the membrane-bound type RAGE polypeptide, and having a serial amino acid sequence comprising at least 1 to 16 amino acid residues out of $Glu^{332}$ to $Met^{347}$ of the amino acid sequence described in the SEQ ID No. 2 of the sequence listing at its C terminal; and (d) a polypeptide having amino acid sequence as described in the SEQ ID No. 2 of the sequence listing, or a polypeptide exhibiting substantially equivalent biological activity with the polypeptide described in the SEQ ID No. 2 of the sequence listing;

(2) a polypeptide comprising at least 1 to 16 amino acid residues out of $Glu^{332}$ to $Met^{347}$ of the amino acid sequence described in the SEQ ID No. 2 of the sequence listing; and comprising the following part of the amino acid sequence described in the SEQ ID No. 2 of the sequence listing or a salt thereof:

(i) a serial amino acid sequence comprising at least 5 to 115 amino acid residues;

(ii) a serial amino acid sequence comprising at least 116 to 230 amino acid residues;

(iii) a serial amino acid sequence comprising at least 231 to 347 amino acid residues;

(iv) a serial amino acid sequence comprising at least one amino acid residue out of the $1^{st}$ to $117^{th}$ amino acid residues;

(v) a serial amino acid sequence comprising at least one amino acid residue out of the $332^{nd}$ to $347^{th}$ amino acid residues;

(vi) an amino acid sequence comprising the $19^{th}$ to $347^{th}$ amino acid residues;

(vii) a serial amino acid sequence comprising the $1^{st}$ to $347^{th}$ amino acid residues; and (viii) a polypeptide having an amino acid sequence substantially equivalent to any one of the above-mentioned polypeptides;

(3) a polypeptide selected from the polypeptides previously described in (1) or (2), which has an activity toward diseases caused by alteration in the interaction between AGE and its receptor, the expression of the soluble RAGE and/or the activity to capture AGE, or a salt thereof; and (4) a partial peptide or a salt of a polypeptide selected from the polypeptides as described in (1), (2) and (3).

[2] A nucleic acid having a base sequence coding for the polypeptide according to [1].

[3] The nucleic acid according to [2] having a base sequence selected from a group comprising:

(i) a base sequence described in the SEQ ID No.1 of the sequence listing, comprising at least its open reading frame region;

(ii) a base sequence which at least hybridizes with the base sequence as described in said (i) under a stringent condition;

(iii) a base sequence which hybridizes, under a stringent condition, with a serial base sequence comprising five or more bases of the base sequence as described in the SEQ ID No. 1 of the sequence listing, and encodes for an amino acid sequence substantially equivalent to the soluble RAGE polypeptide;

(iv) a base sequence which hybridizes, under a stringent condition, with a serial base sequence comprising ten or more bases of the base sequence as described in the SEQ ID No. 1 of the sequence listing, and encodes for an amino acid sequence substantially equivalent to the soluble RAGE polypeptide;

(v) a base sequence which hybridizes, under a stringent condition, with a serial base sequence comprising fifteen or more bases of the base sequence as described in the SEQ ID No. 1 of the sequence listing, and encodes for an amino acid sequence substantially equivalent to the soluble RAGE polypeptide;

(vi) a base sequence which hybridizes, under a stringent condition, with a serial base sequence comprising twenty or more bases of the base sequence as described in the SEQ ID No. 1 of the sequence listing, and encodes for an amino acid sequence substantially equivalent to the soluble RAGE polypeptide; and (vii) a base sequence coding for a polypeptide comprising an amino acid sequence having at least 80% homology with the polypeptide described in the SEQ ID No. 2, and/or, a serial amino acid sequence comprising at least 1 to 16 amino acid residues of $Glu^{332}$ to $Met^{347}$ out of the amino acid sequence described in SEQ ID No.2, and exhibiting biological activity substantially equivalent to said soluble RAGE polypeptide-including AGE binding activity, suppressive or inhibitory activity on interaction between AGE and its receptor, and antigenicity substantially equivalent to said soluble RAGE polypeptide.

[4] The nucleic acid according to [2] or [3] containing the open reading frame region of the base sequence described in the SEQ ID No.1 of the sequence listing or a base sequence substantially equivalent to the open reading frame region.

[5] A vector containing the nucleic acid according to any one of [2] to [4].

[6] A transformant containing the nucleic acid according to any one of [2] to [4], or the vector according to [5].

[7] The transformant according to [6], wherein the host cell is selected from the group consisting of a prokaryotic cell including *E. coli*, an yeast and an eukaryotic cell including a plant cell and an animal cell including 293T cell, CHO cell and COS cell.

[8] A method for production of the polypeptide according to [1] or a salt thereof, by cultivating the transformant according to [6] or [7].

[9] The polypeptide according to [1] or a salt thereof, obtained by the expression of the transformant according to [6] or [7].

[10] A primer available for PCR amplification of the open reading frame region of the base sequence as described in the SEQ ID No.1 of the sequence listing, a partial sequence thereof, or a base sequence substantially equivalent to the open reading frame region.

[11] A composition containing the polypeptide according to [1] or a salt thereof, the nucleic acid according to any one of [2] to [4], the vector according to [5], or the transformant according to [6] or [7].

[12] A pharmaceutical composition containing the polypeptide according to [1] or a salt thereof, the nucleic acid according to any one of [2] to [4], or the vector according to [5].

[13] The pharmaceutical composition according to [12] which is available for treatment of pathological conditions or symptoms selected from a group consisting of initiation and/or development of diabetic complications, aging-related diseases, Alzheimer disease, arteriosclerosis and diseases resulting from glycation of proteins in living bodies; and invasion and diffusion of cancer cells.

[14] A diagnostic agent containing a polypeptide according to [1] or a salt thereof, the nucleic acid according to any one of [2] to [4], the vector according to [5], or the transformant according to [6] or [7], which is adapted for diagnosing diseases resulting from alteration in the interaction between AGE and their receptor; in the amount of expression of the soluble RAGE polypeptide; and/or in the activity to capture AGE.

[15] A pharmaceutical composition containing a compound capable of promoting or inhibiting biological activity of the polypeptide according to [1] or a salt thereof, or the nucleic acid according to any one of [2] to [4].

[16] A method for screening or a screening kit useful for carrying out the method, for screening a compound capable of promoting or inhibiting the biological activity of the polypeptide according to [1] or a salt thereof, or the nucleic acid according to any one of [2] to [4], using any one selected from the group consisting of the polypeptide according to [1] or a salt thereof, the nucleic acid according to any one of [2] to [4], and the vector according to [5] or a transformant according to [6] or [7]

[17] The method for screening or the screening kit according to [16], which is a method for screening or a screening kit available for screening a compound effective for preventing initiation and/or development of diabetic complications.

[18] A compound that regulates production of the soluble RAGE polypeptide which is obtained by using the method for screening or the screening kit according to [16] or [17].

[19] A chimera molecular compound obtained by conjugating the polypeptide according to [1] with an amino acid sequence derived from a organism of different species.

[20] A genetic diagnosis agent for diagnosing diseases related to the soluble RAGE polypeptide, which is for detection of presence of a mutated region existing in the soluble RAGE polypeptide, or in the gene or RNA coding for the soluble RAGE, wherein the mutated region is capable of altering expression or activity of the soluble RAGE polypeptide.

[21] The genetic diagnosis agent according to [20], using one selected from a group consisting of a restriction enzyme capable of specific recognition of a possible mutated region, if any, existing in one selected from gene, mRNA and hnRNA coding for the soluble RAGE polypeptide, and its isoschizomers; and oligonucleotide primers available for gene amplification of a possible mutated region, if any, existing in one selected from gene, mRNA and hnRNA coding for the soluble RAGE polypeptide.

[22] A method for genetic diagnosis for diseases related to the soluble RAGE gene comprising the steps of:
(a) obtaining a nucleic acid sample;
(b) amplifying the nucleic acid sample obtained by the step (a), thereby obtaining amplified nucleic acid fragments which contain a possible mutated region, if any, existing in the soluble RAGE gene; and
(c) detecting the presence of the mutated region in the nucleic acid fragments obtained in the step (b).

The other objects, features and advantages of the present invention will be apparent to those skilled in the art upon reading the following description of this Specification. However, it should be understood that the following description of examples herein concerns only with preferred embodiments, and implemented only for illustration purposes. It will be quite obvious to those skilled in the art that one can easily develop various variations and/or modifications by referring to the description hereof without departing the scope and intention of this invention as defined herein. All the patent documents and references cited herein are cited only for illustration purposes, and their contents should be considered as a part hereof.

The term "and/or" used herein means existence of both of (1) concomitant conjugation and (2) selective conjugation. For example, "treatment and/or prevention" means both of (1) treatment and prevention, and (2) treatment or prevention. In other status, the term "and/or" is intended to mean both of (1) concomitant conjugation and (2) selective conjugation in the same manner.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows base sequences of the nucleic acids coding for the soluble RAGE according to this invention, in comparison with transmembrane type RAGE (full RAGE) which is so-called "soluble RAGE" (U.S. Pat. No. 5,864,018) prepared by artificial genetic engineering using a gene coding for the full RAGE containing the transmembrane domain.

FIG. 3 shows base sequences of full RAGE, U.S. Pat. No. 5,864,018 and soluble RAGE following those of FIG. 2.

FIG. 4 shows base sequences of full RAGE, U.S. Pat. No. 5,864,018 and soluble RAGE following those of FIG. 3.

FIG. 5 shows amino acid sequences of the soluble RAGE polypeptide of this invention, in comparison with the full RAGE and U.S. Pat. No. 5,864,018.

FIG. 7 shows photograph of western blotting using a monoclonal antibody of the soluble RAGE polypeptide according to this invention.

A matured RAGE polypeptide (R), supernatant of the culture medium of COS7 cells with over-expression of the soluble RAGE polypeptide (CM), proteins extracted from human lung (L), and molecular marker containing seven kinds of proteins (M) were separated by SDS-PAGE, and western blotting was performed utilizing supernatant obtained from the culture medium of hybridoma cells capable of producing monoclonal antibody specific to the soluble RAGE peptide.

Figure 9:
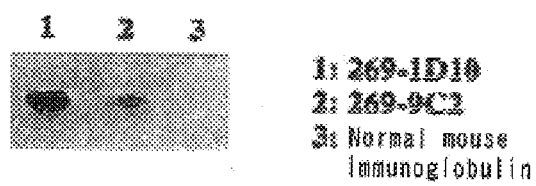

FIG. 9 is a photograph of electrophoresis showing the result of immunoprecipitation using monoclonal antibody of the soluble RAGE polypeptide.

Monoclonal antibody 269-1D10 specific to the soluble RAGE polypeptide (1), 269-9C2 (2), and an immunoglobulin obtained from the normal mouse (3) were separately bound to a protein G Sepharose. A culture medium of COS7 cells with over-expression of the soluble RAGE polypeptide had been prepared, said protein was immunoprecipitated from the supernatant using the protein G Sepharose, then separated by SDS-PAGE, and the soluble RAGE polypeptide was detected by western blotting.

Figure 10:
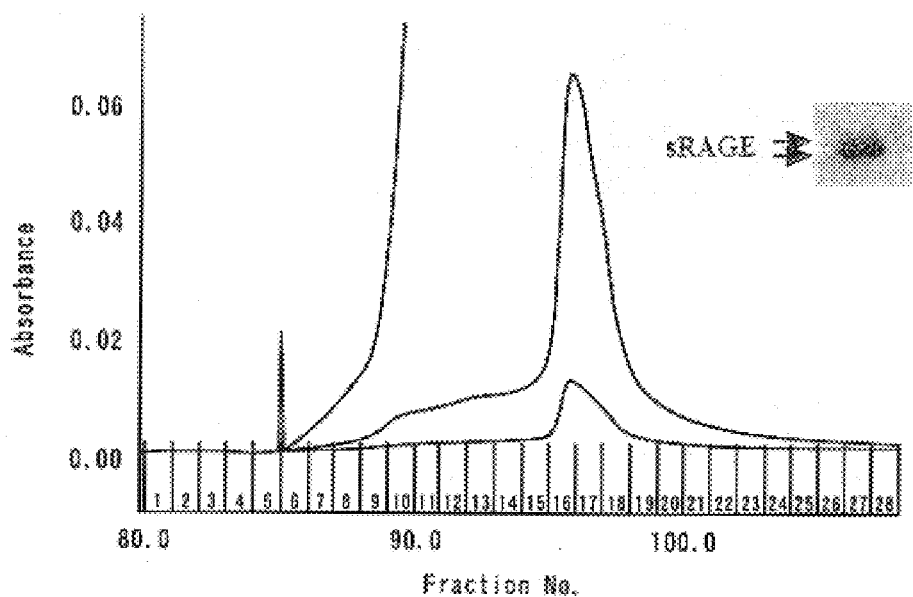

FIG. 10 is a graph showing elution pattern of immunoaffinity column chromatography of human serum using a monoclonal antibody specific to the human soluble RAGE polypeptide, in order to detect the presence of the soluble RAGE polypeptide in human serum, and an electrophoretic photograph of immunoblots of the peak fractions.

Two ml of human serum was applied to an immunoaffinity column conjugated with 2.5 mg of monoclonal antibody 269-1D10 specific to the human soluble RAGE, and then immunoaffinity column chromatography was performed. Fractions (Nos. 16 to 18) showing peak absorption were treated with TCA; the precipitate was separated by SDS-PAGE; and then western blotting was performed using a rabbit polyclonal antibody specific to the human soluble RAGE polypeptide.

Figure 11:
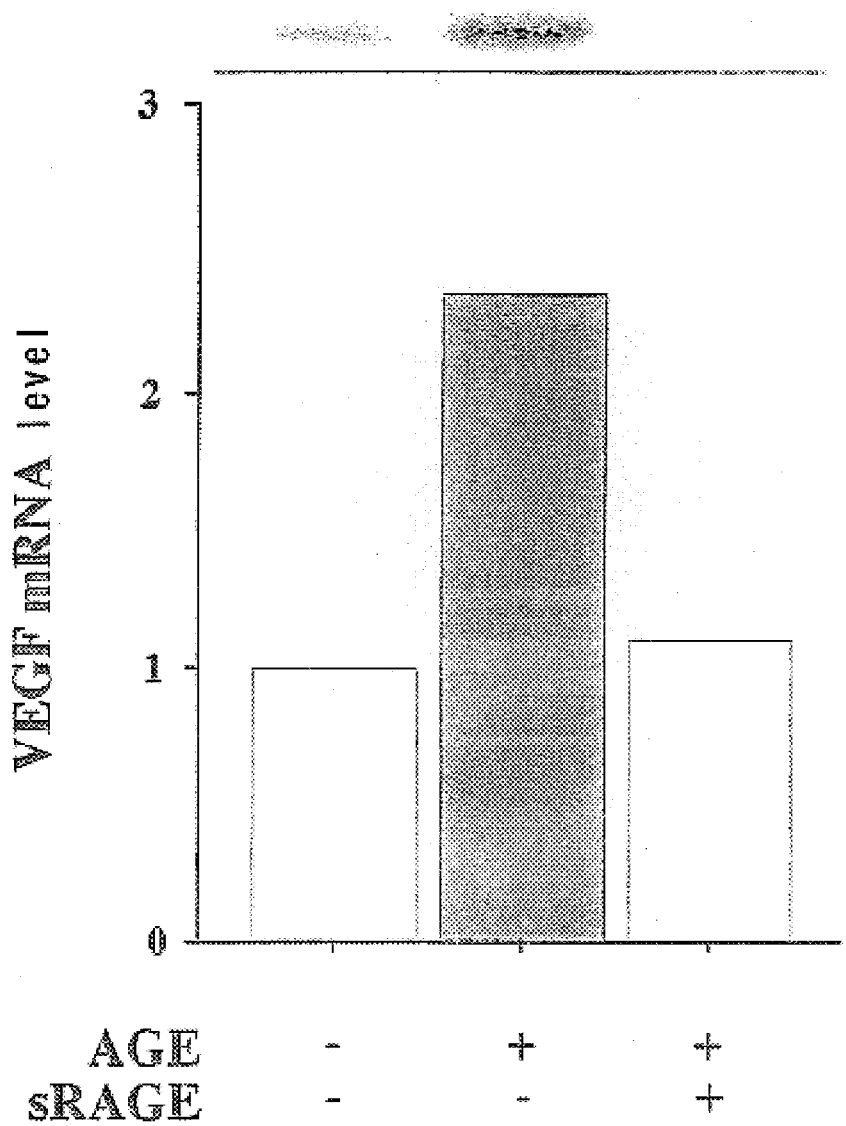

FIG. 11 is a photograph showing neutralization of AGE action on the endothelium by the soluble RAGE. Microvascular endothelial cells derived from human skin were treated with vehicle alone (1), or with 10 µg/ml of AGE-BSA (2), or in the presence of 10 µg/ml of AGE-BSA and 25 µg/ml of purified soluble RAGE polypeptide (3), then poly(A)$^+$ oligonucleotide was separated from the cell to detect VEGF mRNA.

DETAILED DESCRIPTION OF THE PREFERRED EMBODIMENTS

The term "soluble RAGE" as used herein is a polypeptide related to the receptor for advanced glycation endproducts (RAGE), which is closely involved in development of diabetic complications, and refers to a novel polypeptide disclosed in this invention, which is a splicing variant of the RAGE which do not contain a transmembrane domain. The soluble RAGE polypeptide is a polypeptide comprising 347 amino acid residues, having a characteristic amino acid sequence of GluGlyPheAspLysValArgGluAla-GluAspSerProGlnHisMet on its C terminal, and lacks the transmembrane domain of full-length RAGE polypeptide (referred to as membrane type or membrane bound type RAGE), which is unique feature of the soluble RAGE polypeptide. The soluble RAGE polypeptide has activity to specifically bind to advanced glycation endproducts (AGEs), or to suppress or inhibit the binding between AGE and its receptors. Typically, the soluble RAGE polypeptide according to this invention is a native form peptide (intrinsic or endogenous RAGE polypeptide) existing in a living body and differs from conventional RAGE protein at 16 amino acid residues existing at its C terminal. The representative soluble RAGE polypeptide of this invention includes novel polypeptides encoded and produced by the DNA described in the SEQ ID No.1 of the sequence listing, or the polypeptide comprising the amino acid sequence as described in the SEQ ID No.2 of the sequence listing, or an amino acid sequences substantially equivalent to said sequence. The representative soluble RAGE polypeptide according to this invention includes novel polypeptides that comprise, on their C terminal, a serial amino acid sequence comprising 1 to 16 amino acid residues out of the amino acid sequence of Glu$^{332}$ to Met$^{347}$ of the SEQ ID No.2 of the sequence listing, and exhibiting the activity to bind to AGE; polypeptides that comprise, on their N terminal, a serial amino acid sequence comprising 1 to 117 amino acid residues out of the amino acid sequence of Met$^1$ to Val$^{117}$ of the SEQ ID No. 2 of the sequence listing, and exhibiting the activity to bind to AGE; or polypeptides that comprise an amino acid sequence having at least 60% homology with the amino acid sequence of Tyr$^{118}$ to Gly$^{331}$ of the SEQ ID No. 2 of the sequence listing, and exhibiting the activity to bind to AGE.

The term "polypeptide" as used herein includes any polypeptides as will be described below. The basic structure of a polypeptide is well known, and is exhaustively described in many textbooks, reference books and journals in the relevant technical fields. In view of these references, the term "polypeptide" as used herein means peptides or proteins obtained by conjugating two or more amino acids via peptide bonding or via any other modified peptide bonding, that is, peptides or proteins having any given length. The "polypeptide" as used herein may include, for example, short chain peptides such as peptides, oligopeptides and peptide oligomers, and long chain peptides such as so-called proteins which are known to have widely different structures. The polypeptide may optionally comprise amino acids other than the twenty standard amino acids (native amino acids, or amino acids encoded by genes). It should be understood that said polypeptide, including its terminal, may undergo natural alterations (modifications) by natural process such as processing which occurs after the majority of amino acid residues has been translated and other alterations (modifications), as well as by chemical modification techniques well known to those skilled in the art. As to the alterations (modifications) made to the polypeptide, various manners are known and described in details in many basic textbooks, and research papers and journals in the relevant fields, and are well known to those skilled in the art. The common alterations/modifications may include, for example, glycosylation, lipid bonding, sulfation, γ-carboxylation of glutamic acid residues, hydroxylation and ADP-ribosylation. See, for example, description in T. E. Creighton, "Proteins-Structure and Molecular Properties," Second Edition, W.H. Freeman and Co., New York (1993); B. C. Johnson (Ed.), "Post Traslational Covalent Modification of Proteins," Academic Press, New York (1983) (Wold, F., "Posttranslational Protein Modifications: Perspectives and Prospects," pp. 1-12); Seifter et al., "Analysis for Protein Modifications and Nonprotein Cofactors," Meth. Enzymol., 182:626-646(1990); and Rattan et al., "Protein Synthesis: Posttranslational Modification and Aging," Ann. N. Y. Acad. Sci., 663:pp. 48-62(1992).

The "polypeptide" of this invention particularly includes the soluble RAGE polypeptide and its related polypeptides. The soluble RAGE polypeptide and its related polypeptides include those derived from human, or those that are water-soluble and exhibit the activity to bind to AGE, or those lacking the transmembrane domain existing in the transmembrane-type RAGE polypeptide, for example, that one lacks transmembrane domain exhibiting the activity to bind to AGE. The representative soluble RAGE polypeptide includes polypeptides having the characteristic amino acid sequence comprising GluGlyPheAspLysValArgGluAla-GluAspSerProGlnHisMet at its C terminal, or more specifically polypeptides that have an amino acid sequence comprising at least 332nd to 347th, 1st to 117th, 19th to 347th, or 1st to 347th amino acid residues out of the amino acid sequence described in the SEQ ID No.2 of the sequence listing, or polypeptides that have at least 60%, preferably at least 70%, more preferably at least 80%, yet more preferably at least 85%, yet more preferably at least 90%, yet more preferably at least 95%, or most preferably at least 97% homology with any one of said polypeptides and still exhibiting substantially equivalent biologically activity, such as AGE binding activity, i.e. suppressive or inhibitory activity on interaction between AGE and its receptor; and the same extent of antigenicity.

The human soluble RAGE polypeptide according to this invention may include any polypeptides; free polypeptides not bound to membrane; water-soluble polypeptides exhibiting the activity to specifically bind to AGE; polypeptides lacking the transmembrane domain commonly observed in the transmembrane-type RAGE polypeptide; polypeptides containing an amino acid sequence comprising Glu-Gly-Phe-Asp-Lys-Val-Arg-Glu-Ala-Glu-Asp-Ser-Pro-Gln-His-Met or a partial peptide thereof at its C terminal, which are one of splicing variants of RAGE family polypeptides and still having a novel amino acid sequence. More preferably, the soluble RAGE polypeptide of this invention includes, out of the polypeptides having at least 60% homology with RAGE family polypeptides, those lacking the transmembrane domain and containing a serial amino acid sequence comprising at least 1 to 16 amino acid residues out of $Glu^{332}$ to $Met^{347}$ of the sequence ID No.2 of the sequence listing, particularly those containing a serial amino acid sequence comprising at least the sequence region of 332nd to 347th amino acid residues, 1st to 117th amino acid residues or a part of the sequence bearing the principle function (e.g., a serial amino acid sequence containing all or a part of 332nd to 347th amino acid residues, or a serial amino acid sequence comprising five or more, preferably ten or more, more preferably 20 or more, yet more preferably 30 or more, yet more preferably 40 or more, yet more preferably 50 or more, yet more preferably 60 or more, yet more preferably 70 or more, yet more preferably 80 or more, yet preferably 90 or more, most preferably 100 or more, yet further preferably 110 or more of 1st to 347th amino acid residues out of the above-mentioned amino acid sequence) listed in the SEQ ID No.2 of the sequence listing. The representative polypeptide of this invention includes one selected from a group comprising polypeptides that have an amino acid sequence comprising at least 19th to 347th amino acid residues out of the amino acid sequence described in the SEQ ID No. 2 of the sequence listing, and polypeptides that have an amino acid sequence essentially equivalent to either one of that of the above polypeptides. The polypeptide according to this invention may further include polypeptides that have an amino acid sequence comprising entirely or a part of the amino acid sequence described in the SEQ ID No.2 of the sequence listing. All the polypeptides cited above may be included within the scope of this invention.

The term "homology" as used herein means the quantity (number) that enables determination of identity between two polypeptide sequences (or amino acid sequences) or polynucleotide sequences (or base sequences), in matching each of the amino acid residues or each of the bases constituting the two strands, which means the degree representing the sequence similarity between the two polypeptide sequences or two polynucleotide sequences. The homology between a given pair of polypeptides or polynucleotides can be easily determined. Many methods have been developed for determination of the homology between a given pair of polypeptides or polynucleotides, and the meaning meant by the term "homology" is widely known among those skilled in the art (see, for example, Lesk, A. M. (Ed.), "Computational Molecular Biology," Oxford University Press, New York (1988); Smith, D. W. (Ed.), "Biocomputing: Informatics and Genome Projects," Academic Press, New York (1993); Griffin, A. M. & Griffin, H. G. (Ed.), "Computer Analysis of Sequence Data: Part I," Human Press, New Jersey (1994); von Heinje, G., "Sequence Analysis in Molecular Biology," Academic Press, New York (1987); Gribskov, M. & Devereux, J. (Ed.), "Sequence Analysis Primer," M-Stockton Press, New York (1991), etc.). The conventional method used for determining the homology between two sequences includes, for example, those as disclosed in Martin, J. Bishop (Ed.), "Guide to Huge Computers," Academic Press, San Diego (1994); Carillo, H. & Lipman, D., "SIAM," J. Applied Math., 48:1073(1988), etc., but not to be limited to them. A preferred method for determining the homology between two sequences includes one that designed to obtain a part of two sequences exhibiting the highest matching. Such method includes that accomplished by a computer program. The preferred computer program designed to determine the homology between two sequences includes computer program packages such as GCG program package (Devereux, J. et al., Nucleic Acid Research, 12(1):387(1984)), BLASTP, BLASTN, FASTA (Atschul, S. F. et al., J. Molec. Biol., 215:403(1990), etc., but it is not intended to limited to them, and may include any known appropriate program known in the relevant field.

The nucleic acid coding for the soluble RAGE polypeptide according to this invention typically includes those that contain base sequences coding for the polypeptide as represented by the amino acid sequence is as described in the SEQ ID No.2 of the sequence listing and a serial amino acid sequence derived from a part thereof, for example, nucleic acids that have a base sequence comprising at least the 25th to 1068th bases out of the base sequence described in the SEQ ID No.1 of the sequence listing; nucleic acids that have a base sequence comprising at least 136th to 1065th bases out of the base sequence described in the SEQ ID No.1 of the sequence listing; nucleic acids that have a base sequence comprising from ATG at the 25th to 27th bases to TGA at the 1066th to 1068th bases (TGA stop codon at the 1066th to 1068th may be TAA or TAG) out of the base sequence described in the SEQ ID No.1 of the sequence listing; nucleic acids that have a base sequence comprising the 25th to 1065th bases out of the base sequence described in the SEQ ID No.1 of the sequence listing; nucleic acids with the start codon (codon coding for Met) and the stop codon added to the nucleic acid sequences just mentioned above; and any of the nucleic acids exhibiting essentially equivalent functionality comprising base sequences coding for polypeptides exhibiting at least 80% homology with amino acid sequence of the protein and still containing at least 1 to 16 amino acid residues out of $Glu^{332}$ to $Met^{347}$ of the amino acid sequence described in the SEQ ID No.2 of the sequence listing, yet exhibiting substantially equivalent biological activity to the soluble RAGE polypeptide, such as the activity to bind with AGE, the activity to suppress or inhibit the interaction between AGE and their receptor, or equivalent antigenicity. The nucleic acid coding for the soluble RAGE polypeptide includes nucleic acid such as a single strand DNA, double strand DNA, RNA, DNA/RNA hybrid, and synthetic DNA, or may be human genomic DNA, human genomic DNA library, cDNA derived from a human tissue or cell, or synthetic DNA. The base sequence of the nucleic acid coding for the RAGE polypeptide may undergo modifications (e.g., insertion, deletion or substitution), and this invention may include such modified nucleic acids. The nucleic acid according to this invention may include those coding for the peptides of this invention or a part thereof, preferably a DNA. The base sequence "exhibiting essentially equivalent functionality" described above includes those that can hybridize with base sequences comprising five or more, preferably ten or more, yet more preferably 15 or more, yet more preferably 20 or more serial bases of the base sequence described in the SEQ ID No.1 of the sequence listing, still coding for polypeptides essentially equivalent to the soluble RAGE polypeptide.

The DNA according to this invention having a base sequence represented by the sequence ID No. 1 of the sequence listing, or DNA exhibiting essentially equivalent functionality to said DNA can be obtained, for example, by the following methods.

Recombinant DNA technique can be performed according to the methods described in the following documents, or to the methods described in the references cited in the documents, or methods or modified methods essentially similar to above. The documents are: J. Sambrook, E. F. Fritsch & T. Maniatis, "Molecular Cloning: A Laboratory Manual (2nd edition)," Cold Spring Harbor Laboratory Press, Cold Spring Harbor, N.Y. (1989); D. M. Glover et al., (ed.) "DNA Cloning," 2nd ed., Vols. 1 to 4, (The Practical Approach Series), IRL Press, Oxford University Press (1995); Japanese Society for Biochemistry (ed.), "Further Lecture on Biochemical Experiment 1, Studies on Genes II," Tokyo Kagaku Doujin (1986); Japanese Society for Biochemistry (ed.), "New Lecture on Biochemical Experiment 2, Nucleic Acid III (Recombinant DNA Technique)," Tokyo Kagaku Doujin (1992); R. Wu (ed.), "Methods in Enzymology," Vol. 68 (Recombinant DNA)," Academic Press, New York (1980); R. Wu et al. (ed.), "Methods in Enzymology," Vols. 100 (Recombinant DNA, Part B) & 101 (Recombinant DNA, Part C), Academic Press, New York (1983); R. Wu et al. (ed.), "Methods in Enzymology," Vols. 153 (Recombinant DNA, Part D), 154 (Recombinant DNA, Part E) & 155 (Recombinant DNA, Part F), Academic Press, New York (1987); J. H. Miller (ed.), "Methods in Enzymology," Vol. 204, Academic Press, New York (1991); and R. Wu et al. (ed.), "Methods in Enzymology," Vol. 218, Academic Press, New York (1993). Those documents are incorporated herein by way of citation.

A human cDNA library has been constructed from various human tissues or cultured cell (particularly from human kidney, brain, pineal body, posterior lobule of hypophysis, nerve cells, retina, retinal vascular cells, thymus, vessels, endothelial cells, vascular smooth muscle cells, blood cells, macrophages, lymphocytes, testicle, ovary, uterus, bowel, heart, liver, pancreas, small intestine, colon, gingival cells, cutaneous cells, glomerular cells, uriniferous tubule, connective tissue, etc.), and plasmids containing the inserted cDNA sequence derived from the cDNA library were screened using an appropriate detection system, based on at least one of the following activities as an index, those are; AGE binding activity, suppressive or inhibitory activity on interaction between AGE and their receptor. This screening method may be repeated. The identified nucleic acid is subjected to sequencing. Appropriate primers are designed and synthesized according to thus identified nucleotide sequence, and the sequence of purpose can be amplified using PCR (Polymerase Chain Reaction), occasionally using cDNA library derived from an animal which is the origin of the identified sequence. The DNA fragment thus obtained can be used as a probe for screening human genomic DNA library or human derived cDNA library constructed from various human tissues or cultured cells etc., then clones capable of hybridizing to the probe are selected, base sequence of the cDNA inserts are sequenced; and thus DNA fragments having base sequence coding for the novel soluble RAGE polypeptide or related sequences can be identified and obtained. The DNA inserts may be subcloned as needed. Based on the DNA sequence coding for the novel polypeptide, it is possible to obtain genes encoding the soluble RAGE polypeptide and the related sequences. Furthermore, using the DNA sequences coding for the novel soluble RAGE polypeptide and related sequences, a sense primer and an anti-sense primer may be designed and synthesized. The sense primer may preferably selected and synthesized based on the exon region at 5' end of the DNA segment assumed to be coding for the polypeptide, while the antisense primer is preferably selected and synthesized based on the exon region at 3' end of the same DNA segment. Preferably, the exon region used for designing the antisense primer may be selected from a region different from the region used for synthesis of the sense primer.

An attempt may be made to obtain full length of the cDNA segment at one time. Alternatively, however, using the analyzed exon region (plural exon regions), plural primers can be designed and synthesized for plural PCR (the sequenced DNA fragment is subjected to analysis as needed, entire base sequence of the cDNA is determined, then cloning is performed based on the sequence), then base sequence of the cDNA can be determined, then cDNA of the purpose can be accompanied with the DNA fragment obtained. The primer may include oligo-nucleotides having a length of preferably five or more bases, more preferably ten or more bases, yet more preferably 18 to 25 bases. Preparation of primers may be achieved by the methods conventionally known in the art represented by the methods based on phosphodiester method, phosphotriester method or phosphoramidite method, for example, using an automated DNA synthesizer such as a model 381A DNA synthesizer (Applied Biosystems). PCR may be performed using the cDNA library and the sense and antisense primers, for amplification of the cDNA. Alternatively, the nucleic acid can be obtained by preparing a specific hybridization probe based on the identified clone as described above, screening cDNA library originated from human and selecting clones that hybridizes with the probe. The probe may be labeled with a radioactive isotope. For this purpose, commercially available kits such as a random prime DNA labeling kit (Boehringer Mannheim) may be used. A DNA probe may be labeled with $[\alpha\text{-}^{32}P]dCTP$ (Amersham) using a random-priming kit (Pharmacia LKB, Uppsala) to give a radiolabeled probe.

The template may be prepared from commercially available cDNA libraries originated from various tissues and provided, for example, by Stratagen, Invitrogen, Clonetech, etc. Typically, a gene library prepared from the labeled DNA fragment and human tissues or cells, such as a bacterial artificial chromosomes human genomic library (Human Genome Mapping Resource Center), human brain cDNA library(for example, available from Clonetech), etc., can be used for hybridization. A human brain cDNA library may be constructed in a phage such as λgt10; the phage can be infected to a host *E. coli* such as C600hfl; and then there are formed plaques on the culture. The DNA insert may be subcloned as needed. It is possible to separate the desired DNA fragment using the determined base sequence obtained above.

Sequencing of a DNA fragment may be achieved by dideoxy method such as M13 dideoxy method, or by Maxam Gilbert method using a commercially available sequencing kit such as a Taq di-primer cycle sequencing kit (Applied Biosystems), Sequenase v 2.0 kit, automated sequencer such as fluorescence-based DNA sequencer (e.g., Model 1373A, Applied Biosystems). The polymerase used in the dideoxy method includes, for example, Klenow fragment from DNA polymerase I, AMV reverse transcriptase, Taq DNA polymerase, T7DNA polymerase and modified T7 DNA polymerase.

The "polymerase chain reaction" or "PCR" as used herein refers generally to a method as described in the U.S. Pat. No. 4,683,195, particularly to an in-vitro method for enzymatic amplification of a desired nucleotide sequence. Generally, PCR method is achieved by employing a template nucleotide sequence, and two oligonucleotide primers, which have a strong tendency to hybridize to the template nucleic acid, allowing elongation of the primers in accordance with the template for each cycle, and repeating the cycle at plural times. Typically, primers used in PCR may be a primer complementary to the nucleotide sequence within the template to be amplified, for example, those complementary to the both ends of the desired nucleotide sequence, preferably consisting of nucleotide sequences flanking the desired nucleotide sequence.

PCR may be achieved by any publicly known methods, methods essentially similar to them, or their modified methods, for example, by the methods as described in R. Saiki et al., Science 230:1350, 1985; R. Saiki et al., Science 239:487, 1988; H. A. Ehrlich (ed.), "PCR Technology," Stockton Press, 1989; D. M. Glover et al. (ed.), "DNA Cloning," 2nd ed., Vol. 1, (The Practical Approach Series), IRL Press, Oxford University Press(1985); M. A. Innis et al. (ed.), "PCR Protocols: A Guide to Methods and Applications," Academic Press, New York (1990); M. J. McPherson, P. Quirke and G. R. Taylor (ed.), "PCR: A Practical Approach," IRL Press, Oxford (1991); and M. A. Frohman et al., Proc. Natl. Acad. Sci. USA 85:8998-9002(1988), otherwise the modification of these methods or variants of these methods. PCR method may be achieved using a commercially available kit in accordance with a protocol available from the manufacturer or distributor.

Typical PCR occurs, for example, as follows. The first DNA strand serving as a template and the primers are combined with 10× buffer (attached to the Taq polymerase preparation), dNTPs (mixture of deoxynucleoside triphosphates, i.e., dATP, dGTP, dCTP and dTTP), Taq DNA polymerase and deionized or distilled water. The mixture is applied, for example, to an automated thermal cycler (e.g., GeneAmp 2400PCR system, Perkin-Elmer/Cetus), and 25 to 60 cycles of amplification are repeated under a normal PCR cycle condition. However, the number of amplification cycle may be varied as appropriate depending on the given purpose. Usually the PCR cycle includes denaturation at 90-95° C. for 5 to 100 sec; annealing at 40-60° C. for 5 to 150 sec; and elongation at 65-75° C. for 30 to 300 sec, preferably denaturation at 94° C. for 15 sec; annealing at 58° C. for 15 sec; and elongation at 72° C. for 45 sec. The temperature and reaction time used for annealing may be varied depending on the given experimental conditions, and the temperature and reaction time adopted for denaturation and elongation may be varied depending on the expected length of the PCR product. The reaction temperature for annealing may be generally adjusted in accordance with the Tm value of hybrid between the primer and the template DNA. The reaction time for elongation may be adjusted in such a manner, so as to permit one minute for the elongation of every 1000 bp, but the reaction time may be reduced if needed.

The PCR product obtained is usually subjected to gel electrophoresis with 1-2% agarose gel; gel bands are separated; and DNA is extracted from each band using a commercially available kit such as a gene clean kit (Bio 101). The DNA molecule may be cleaved with an appropriately chosen restriction enzyme, and purified as needed, and optionally the 5' ends of cleaved DNA fragments are phosphorylated with T4 polynucleotide kinase. The DNA fragments are ligated with an appropriately chosen plasmid vector, e.g., pUC vectors such as PUC18, used to transform appropriately chosen competent cells. Then the base sequences of the PCR products thus cloned are sequenced.

Incidentally, in the exon region of the gene, a primer designed based on the analyzed 5' end exon region can be utilized to obtain cDNA at the 5' end of the desired cDNA. Meanwhile, in the exon region of the gene, a primer designed based on the analyzed 3' end exon region can be utilized to obtain cDNA at the 3' end of the desired cDNA. Then these primers or information on the base sequence of the 5' or 3' end cDNA of the obtained gene can be used to design primers, if needed, the primers can be used to perform PCR amplification using the $1^{st}$ strand cDNA as a template to obtain the cDNA of the gene according to this invention, wherein the $1^{st}$ strand cDNA can be produced from mRNA by reverse transcriptase isolated prepared from human tissues, for example human brain.

The primer for the 5' end is selected to include at least the initiation codon, or to enable of DNA fragment amplification in the manner to include the initiation codon. Moreover, the primer for the 3' end is selected to include at least the stop codon, or to enable PCR amplification in the manner to include the stop codon. The PCR reaction can be performed as described above to obtain the full-length cDNA that corresponds to the gene, and the PCR condition may preferably be the cycle consisting of, for example, denaturation at 92-95° C. for 10-20 sec; annealing at 55-60° C. for 10-30 sec; and elongation at 65-75° C. for 150-300 sec, more preferably it may be the cycle consisting of, denaturation at 94° C. for 15 sec; annealing at 58° C. for 15 sec; and elongation at 68° C. for 4 minutes.

PCR products thus obtained were cloned by the above recombinant DNA technique and then the sequences were determined.

Moreover, primers may be designed based on the base sequence of the determined DNA, and screening may be performed using these primers and cDNA libraries obtained from various animal cells (e.g., cDNA library from various human cells) to obtain the target DNA in the same manner. Furthermore, PCR amplification may be carried out using the primers to obtain nucleic acid containing the target coding sequence, novel genes and the fragments thereof. In this way, PCR products with novel sequence exhibiting high homology with the soluble RAGE polypeptide can be obtained.

The term "oligonucleotide" in this specification means relatively short single stranded or double stranded polynucleotide chains, preferably it may be polydeoxynucleotide. The oligonucleotide can be chemically synthesized by a known method, such as triester method, phosphite method, phosphoamidite method and phosphonate method as described in Angew, Chem. Int. Ed. Engl., Vol. 28, pp. 716-734(1989). In general, such oligonucleotide can be synthesized conveniently on a solid support, for example, such synthesis can be achieved using a commercially available automated synthesizer. The oligonucleotide may contain one or more modified bases, for example, unusual nucleic acids such as inosine or tritylated bases.

The obtained PCR product can be cloned, and base sequence of the obtained PCR product can be determined to obtain DNA fragments containing the sequence coding for the novel soluble RAGE polypeptide or the polypeptides related to the RAGE polypeptide. Moreover, the DNA fragments can be used as a probe and various cDNA libraries can be screened in the same manner to isolate the target DNA. Cloning of the PCR product may be achieved by employing commercially available plasmid vectors such as p-Direct (Clontech), pCR-Script(TM) SK(+)(Stratagene), pGEM-T (Promega) and pAmp(TM) (Gibco-BRL).

To construct a cDNA library, it is requisite to obtain cDNA. This may be achieved as follows. For example, an mRNA can be isolated from various human tissues or culture cells. Here, isolation of mRNA can be achieved by methods conventionally known in this art or by a modified method substantially equivalent to such methods. The example of such method are those described in J. Sambrook et al., "Molecular Cloning," 2nd ed., Chapter 7, Cold Spring Harbor Laboratory Press, Cold Spring Harbor, N.Y., (1989); D. M. Glover et al. (ed.), "DNA Cloning," 2nd ed., Vol. 1, (The Practical Approach Series), IRL Press, Oxford University Press (1995); L. Grossman et al. (ed.), "Methods in Enzymology," Vol. 12, Part A & B, Academic Press, New York (1968); S. L. Berger et al. (ed.), "Methods in Enzymology," Vol. 152, p. 33 & p. 215, Academic Press, New York (1987); and Biochemistry 18:5294-5299, 1979, for example, guanidine-cesium chloride method, guanidine thiocyanate method and phenol method. The commercially kit available for isolation of mRNA includes, for example, those provided by Pharmacia, Staragene and Gibco-BRL. The obtained total RNA can be purified using an oligo (dT)-cellulose column, a spin column or oligo(dT) binding magnetic beads to obtain poly $(A)^+$mRNA.

For production of the cDNA, this mRNA and transcriptase (RNA dependent DNA polymerase) can be utilized. In the reverse transcription reaction an oligo(dT) primer may be used. The oligo(dt) primer may preferably comprise 12 to 18 T residues. For the directional cloning, a synthetic oligonucleotide primer containing restriction site ligated to 5' site comprising 12 to 18 T residues may be preferably used. Such primer includes, for example, XbaI oligo(dt) primer-adapter. If a random hexamer primer is used, 5' end of mRNA can be obtained with high possibility. This random hexamer primer may be used alone or in combination with an oligo(dT) primer. In the reverse transcription reaction, a RNase inhibitor such as RNasin (Boehringer Mannheim) may be added as needed. Synthesis of cDNA using mRNA and reverse transcriptase may be achieved by any methods known in the art, or any other methods substantially identical to them or their variations. For example, such methods are described in H. Land et al., Nucleic Acids Res., 9:2251, 1981; U. Gubler et al., Gene, 25:263-269, 1983; and S. L. Beger et al. (ed.), "Methods in Enzymology," Vol. 152, p. 307, Academic Press, New York (1987).

Based on the cDNA thus obtained, a cDNA library can be constructed utilizing a phage vector or a plasmid vector. To achieve transformation of a host cell (such as *E. coli*) by a method other than a method utilizing phage vector, a conventional method in this art or a method substantially identical to the method can be utilized. Examples of such method can be listed as calcium method, rubidium/calcium method, calcium/manganese method, high efficiency TFB method, FSB freezing competent cell method, rapid colony method and electroporation method (D. Hanahan, J. Mol. Biol., 166:557, 1983).

In order to isolate the target DNA, RT-PCR (polymerase chain reaction coupled reverse transcription) or RACE (rapid amplification of cDNA ends) can be applied for this purpose. RACE may be carried out according to a method as described in M. A. Innis et al., (ed.), "PCR Protocols," in M. A. Frohman's "Guide to Methods and Applications," pp. 28-38, Academic Press, New York (1990). The products of RT-PCR may be cloned into a plasmid vector, and the plasmid vector may be introduced into high-efficient competent cells.

A method that enables isolation and purification of mRNA from minute quantities of cells or tissue can be adopted. For example, a commercially available kit such as REX kit (United States Biochemicals), or Glass MAX™ RNA spin cartridge system (Gibco-BRL) can be utilized to produce mRNA. The obtained mRNA is reverse transcribed using oligo(dT) primer to synthesize the 1st strand DNA, subsequently a homopolymer tail (e.g., a serial sequence of G residue) is attached to the 3' end of the 1st strand DNA or an adapter is attached to the DNA. Then PCR can be performed using the oligo(dT) primer and an oligo(dC) primer otherwise using the adapter-primer, to perform PCR amplification of the cDNA. The commercially available kit suitable for this purpose may include SuperScript (TM) pre-amplification system (Gibco-BRL) and cDNA Cycle(TM) kit (Invitrogen).

The plaques formed by the microorganisms with certain DNA inserts are transferred to a membrane such as a nylon filter to achieve hybridization. The nylon filter is subjected to denaturation, fixation and washing treatment as needed, and the transferred subject is allowed to react in a hybridization buffer with a labeled DNA probe fragment denatured according to need. Hybridization treatment usually occurs at 35-80° C., preferably at 50-65° C., for 15 minutes to 36 hours, preferably for 1-24 hours, but the optimal condition can be selected ad libitum. For example, typically hybridization treatment is performed at about 55° C. for about 18 hours. The hybridization buffer may be selected from those conventionally used in this art, for example, rapid hybridization buffer (Amersham) can be used. Denaturation of the transferred membrane may be achieved using an alkaline denaturation solution, subsequently it may be preferably treated by a neutralization solution or by a buffer. Fixation of the membrane may be achieved by baking the membrane usually at 40-100° C., preferably at 70-90° C., for 15 minutes to 24 hours, preferably for 1-4 hours, but the optimal condition can be selected ad libitum. For example, fixation of the filter may be achieved by baking at about 80° C. for about 2 hours. Washing treatment of the transferred membrane may be achieved by a washing solution conventionally used in this art, for example, with 1M NaCl, 1 mM EDTA, and 50 mM Tris-HCl buffer (pH8.0) containing 0.1% sodium dodecyl sulfate (SDS). The membrane such as nylon filter may be selected from those conventionally used in this art, for example, nylon filter Hybond-N (Amersham) may be used.

The alkaline denaturation solution, neutralizing solution and buffer described above may be selected from those conventionally used in this art. For example, the alkaline denaturation solution may include, for example, a solution containing 0.5M NaOH and a solution containing 1.5M NaCl; the neutralizing solution may include, for example, 0.5M Tris-HCl buffer (pH8.0) containing 1.5M NaCl; and the buffer may include, for example, 2×SSPE (0.36M NaCl, 20 mM $NaH_2PO_4$, and 2 mM EDTA). To prevent non-specific hybridization reaction, the transferred membrane may preferably be subjected to pre-hybridization treatment. The pre-hybridization treatment consists of, for example, immersing into pre-hybridization treatment solution [50% formamide, 5× Denhardt's solution (0.2% bovine serum albumin, 0.2% polyvinyl pyrrolidone), 5×SSPE, 0.1% SDS, 100 µg/ml of thermally denatured salmon sperm DNA], and reacting the mixture usually at 35-50° C., preferably at about 42° C., for 4-24 hours, preferably for 6-8 hours. The optimum incubation condition can be determined ad libitum by a skilled artisan by repeating experiments. Denaturation of the labeled probe DNA fragment used for hybridization may occur by heating usually at 70-100° C., preferably at 100° C., for 1-60 minutes, preferably for 5 minutes. Meanwhile, hybridization can be achieved by a conventional procedure or by a modified procedure. The stringent condition used in this specification means, for example, sodium concentration of 15-50 mM, preferably 19-40 mM, more preferably 19-20 mM, and temperature of approximately 35-85° C., preferably 50-70° C., more preferably 60-65° C.

After the hybridization is completed, the filter is thoroughly washed to remove unbound probe, except for the labeled probe DNA fragment bound as the result of the hybridization reaction. The washing treatment of the filter may be achieved by washing the filter with a solution selected from those conventionally utilized in this art, such as 0.5× SSC (0.15M NaCl, 15 mM citric acid) solution containing 0.1% SDS.

The hybridized plaques can be detected by a method such as autoradiography, an optimal procedure may be selected for detection of plaques from conventional utilized procedures in this art. The plaques corresponding to the detected signals may be suspended into an appropriate buffer such as SM solution (50 mM Tris-HCl buffer pH7.5 containing 100 mM NaCl and 10 mM $MgSO_4$). Then the phage suspension solution is properly diluted to infect *E. coli*. The obtained *E. coli* may be cultured, and transformant phage of the purpose may be obtained from the cultured *E. coli*. The probe DNA may be used according to need, and screening procedure of the target transformed phage from a gene library or a cDNA library can be repeated by hybridization treatment. Moreover, treatment of the cultured *E. coli* by extraction or centrifugation can provide the transformed phage of target.

The obtained phage particles can be purified and separated by a procedure commonly used in the field, such as glycerol-gradient ultracentrifugation (T. Maniatis (ed.), "Molecular Cloning, A Laboratory Manual," Cold Spring Harbor Laboratory, 2nd ed., p. 78, 1989). DNA can be purified and separated from phage particles by a procedure commonly used in this field. For example, the phage particles thus obtained can be treated to isolate DNA by a method consisting of; suspending the phage particles thus obtained into a TM solution (50 mM Tris-HCl buffer pH7.8 containing 10 mM $MgSO_4$); treating suspension with DNase I and RNase A; adding thereto a mixture consisting of 20 mM EDTA, 50 µg/ml proteinase K and 0.5% SDS; incubating the mixture at about 65° C. for one hour; subjecting the mixture to phenol extraction and diethylether extraction; and subjecting to ethanol extraction for DNA precipitation; washing the obtained DNA by 70% ethanol and drying it; and dissolving the DNA into TE solution (10 mM Tris-HCl buffer, pH8.0 containing 10 mM EDTA). Moreover, the DNA of the target can be obtained in a large scale by a procedure such as subclonig. The subclonig can be performed using *E.coli* as a host and a plasmid vector. The DNA obtained by such subcloning can be purified and separated by the procedure such as centrifugation, phenol extraction and ethanol precipitation, as describe above.

Thus, a clone containing the target DNA (for example, as a transformed phage) can be obtained according to this invention. For example, the total length of the determined base sequence of the isolated DNA insert isolated from the cloned transformed phage, consists of 1223 bp as described in the SEQ ID No. 1 of the sequence listing. In the identified DNA sequence, an open reading frame presumably encoding an amino acid comprising 347 amino acid residues is assumed to exist. The deduced amino acid sequence may be as described in the SEQ ID No. 2 of the sequence listing. This amino acid sequence is a splicing variant of the RAGE polypeptide having a characteristic sequence comprising Glu-Gly-Phe-Asp-Lys-Val-Arg-Glu-Ala-Glu-Asp-Ser-Pro-Gln-His-Met at its C terminal, and the sequence lacks the transmembrane domain existing in the normal membrane-penetrating type RAGE polypeptide. The assumed protein is one of the novel human RAGE polypeptides, and it is designated as "soluble RAGE polypeptide" in this specification. The gene encoding the soluble RAGE polypeptide obviously codes for the polypeptide included in the novel RAGE family, all of the recombinant plasmids produced using the soluble RAGE gene are novel, and transformants or transfectants obtained by transformation or transfection by the plasmids are also novel.

The nucleic acid consisting entirely or partly of the base sequence as described in the SEQ ID No. 1 of the sequence listing may be synthesized chemically. In the case, the fragments may be synthesized and the fragments can be ligated enzymatically. Alternatively, the sequence of the purpose may be obtained using above-mentioned chemically synthesized fragments as a primer or a probe. Primers used for the PCR method are not limited, so far as they can be utilized for amplifying the DNA fragment containing the above-mentioned region. Typically, the primers may comprise (a) oligonucleotides comprising base sequences corresponding to any given region of the base sequence as described in the SEQ ID No. 1 of the sequence listing, and (b) oligonucleotides comprising base sequences complementary to any given region of the base sequence as described in the SEQ ID No. 1 of the sequence listing; preferably (1) an oligonucleotide comprising a base sequence corresponding to any given segment of the 5' terminal region of the base sequence as described in the SEQ ID No. 1 of the sequence listing, and (2) an oligonucleotide comprising a base sequence corresponding to any given segment of the 3' terminal region of the base sequence as described in the SEQ ID No. 1 of the sequence listing, and the oligonucleotide may comprise, for example, five or more bases, preferably 10 or more bases, more preferably 15 or more bases, or the oligonucleotide may contain 3-150 nucleotides, more preferably 10-150 nucleotides, yet more preferably 10-50 nucleotides, yet more preferably 15-35 nucleotides. The condition for PCR is not specifically limited and conditions conventionally utilized in this field may be adopted, for example, the condition can be selected according to the descriptions in the literatures listed above. In PCR operation, a cycle consisting of denaturation of the DNA strand, primer annealing, and synthesis of complementary DNA strand by polymerase may be repeated, for example, 10 to 50 cycles, preferably 20 to 35 cycles, more preferably at 25 to 30 cycles.

The DNA fragment obtained in this invention may be inserted into an appropriate vector, for example, vectors such as planmidpEX, pMAMneo and pKG5, and may be expressed in a host cell such as *E. coli*, yeast, CHO cell and COS cell, and the list of the vectors and the host cells are described below in detail. Moreover, the DNA fragment may be used as it is or as a DNA fragment attached with an appropriate control sequence, and such DNA fragment may can be inserted into an appropriate vector, then the vector may be introduced into a an animal to produce a transgenic animal, for example an animal expressing soluble RAGE polypeptide. The animal available for this purpose includes mammals such as mice, rats, rabbits, guinea pigs and cattle. Preferably, production of a transgenic animal can be achieved by introducing the DNA fragment into a fertilized egg of an animal such as a mouse.

Confirmation on introduction of the soluble RAGE polypeptide product may be achieved by utilizing animal cells such as transfected 293T cells and COS-1 cells, as these cells are appropriate for this purpose. As a method available for introduction of this foreign gene into an animal cell such as a mammalian cell, any methods conventionally known in this art or other methods substantially similar to them can be utilized, for example, calcium phosphate method (see F. L. Graham et al., Virology, 52:456, 1973), DEAE-dextran method (see D. Warden et al., J. Gen. Virol., 3:371, 1968), electroporation method (see E. Neumann et al., EMBO J, 1:841, 1982), microinjection method, ribosomal method, viral infection method and phage particle method can be utilized. Thus, gene products produced from animal cells transformed with a gene of the soluble RAGE polypeptide can be analyzed.

As the plasmid used to insert the gene coding for the soluble RAGE polypeptide and the like (such as the DNA fragment obtained in this invention) any plasmid can be adopted so far as the expression of the DNA can be achieved in a host cell conventionally utilized for genetic engineering, for example, prokaryotic cells such as *E. coli*, *B. subtilis*; eukaryotic cells such as yeast, CHO cells, COS cells; and insect cells such as Sf21 cells. The sequence may include a modified codon advantageous for the expression of the DNA in the selected host cell, it may have a restriction site, or it may contain a regulatory sequence or an enhancing sequence useful to facilitate expression of the target gene, a linker or an adapter available to ligate a target gene, in addition a sequence available to regulate resistance to antibiotic, a sequence available for regulation of metabolism, or a sequence used for selection of the DNA (containing those coding for a hybrid protein or a fusion protein).

Preferably a proper prompter may be used here, for example, prompters such as tryptophan promoter (trp), lactose promoter (lac), tryptophan/lactose promoter (tac), lipoprotein promoter (lpp) and λphage $P_L$ promoter may be utilized for a plasmid utilizing *E. coli* as its host, prompters such as SV40 late promoter, MMTV LTR promoter, RSV LTR promoter, CMV promoter, SRα promoter may be utilized for a plasmid utilizing an animal cell as its host, GAL1 promoter and GAL10 promoter may be utilized for a plasmid utilizing yeast as its host.

A plasmid utilizing *E. coli* as its host may include, for example, pBR322, pUC18, pUC19, pUC118, pUC119, pSP64, pSP65, pTZ-18R/-18U, pTZ-19R/-19U, pGEM-3, pGEM-4, pGEM-3Z, pGEM-4Z, pGEM-5Zf(−) and pBluescript KS™ (Stratagene). The plasmid vector preferable to be utilized for the expression in *E. coli* may include pAS, pKK223 (Pharmacia), pMC1403, pMC931, pKC30 and pRSET-B (Invitrogen). The vector utilizing an animal cell as its host may include SV40 vector, polyoma virus vector, vaccinia virus vector and retrovirus vector such as pcD, pcD-SR, CDM8, pCEV4, pME18S, pBC12BI and pSG5 (Stratagene). The vector utilizing yeast as its host may include YIp type vector, YEp type vector, YRp type vector and YCp type vector such as pGPD-2. In the case *E. coli* is utilized as a host cell, the host cell may include those derived from K12 strain such as NM533, XL1-Blue, C600, DH1, DH5, DH11S, DH12S, DH5α, DH10B, HB101, MC1061, JM109 and STBL2; or those derived from B834 strain such as BL21 (DE3)pLysS. In the case an animal cell is utilized as a host cell, the host cell may include COS-7 cell, COS-1 cell and CV-1 cell from fibroblastoma of African green monkey; COP cell, MOP cell and WOP cell from mouse fibroblastoma; CHO cell and CHO DHFR⁻ cell from Chinese hamster cell; human HeLa cell; C127 cell from mouse cell; and NIH3T3 cell from mouse cell. When the host cell is an insect cell, Bombyx mori nuclear polyhedrosis virus or these derived from the virus may be utilized as a vector and silkworm larva or a cell line derived from silkworm such as BM-N cell may be utilized as a host cell. A plant cell may be also utilized as the host cell, and such plant cells and vectors suitable for the plant cells are widely known in the field.

In the technique of genetic engineering used in this invention, enzymes such as restriction enzyme; reverse transcriptase; DNA modification enzyme or decomposition enzyme that modifies or converts a DNA fragment into a structure suitable for cloning; DNA polymerase; terminal nucleotidyl transferase; and DNA ligase may be utilized. The restriction enzyme may include, for example, those as described in R. J. Roberts, Nucleic Acid Res., 13:r165, 1985; S. Linn et al. (ed.), "Nucleases," p. 109, Cold Spring Harbor Lab., Cold Spring Harbor, N.Y., 1982; and R. J. Roberts & D. Macelis, Nucleic Acid Res., 19:Suppl. 2077, 1991. The reverse transcriptase may include those derived from mouse Moloney leukemia virus (MMLV) and those derived from avian myeloblastosis virus (AMV). As a reverse transcriptases, RNase H deficient mutant may be preferred, particularly a modified MMLV RT deficient of RNase H activity may be preferred, moreover, such a variant with thermal stability is particularly preferred. The preferred reverse transcriptase includes MMLV RT (Gibco-BRL) and Superscript RT plus (Life Technologies).

The DNA polymerase includes DNA polymerase derived from *E. coli*, Klenow fragment which is a derivative thereof, *E. coli* phage T4 DNA polymerase, *E. coli* phage T7 DNA polymerase and heat-resistant DNA polymerase. The terminal nucleotidyl transferase includes TdTase which adds deoxynucleotide (dNMP) to —OH at the 3' terminal, as described in R. Wu et al. (ed.), "Methods in Enzymology," Vol. 100, p. 96, Academic Press, New York (1983). The DNA modification/digestion enzyme may include exonuclease and endonuclease, such as phosphodiesterase from snake venom, phosphodiesterase from spleen, *E. coli* DNA exonuclease I, *E. coli* DNA exonuclease III, *E. coli* DNA exonuclease VII, λexonuclease, DNase I, nuclease S1 and micrococcus nuclease. The DNA ligase may include, for example, *E. coli* DNA ligase and T4 DNA ligase.

The vector suited to be used to clone the target DNA and to construct DNA library containing the target DNA clone may include plasmid, λphage, cosmid, P1 phage, F factor and YAC, and preferably it may include vectors derived from λ phage such as Charon 4A, Charon 21A, λgt10, λgtII, λDASHII, λFIXII, λEMBL3 and λZAPII™ (Stratagene).

Those transformed with the expression vector containing the nucleic acid coding for the protein according to this invention are subjected to cloning repeatedly using an appropriate selection marker as needed, as a result, cell lines exhibiting stable expression of the gene can be obtained. For example, in the case of transformants using an animal cell as a host cell, dhfr gene can be used as a selective marker, the transformants can be cultured under gradually raised concentration of MTX, drug-resistant cells can be selected, and the DNA encoding the protein according to this invention can be amplified to obtain cell lines exhibiting expression of the gene with higher extent. The transformant of this invention can be cultivated under a condition enabling the expression of the nucleic acid coding for the polypeptide according to this invention, thereby production and accumulation of the target product can be achieved. The transformant can be cultured in a medium conventionally utilized in this art. For example, when the host of the transformant utilize prokaryotic cell such as *E. coli* and *B. subtilis*; and yeast, liquid medium may preferably be used to culture the transformants. The medium may contain carbon sources, nitrogen sources, inorganic compounds and other components necessary for the growth of the transformants. The carbon source may include, for example, glucose, dextrin, soluble starch and saccharose. The nitrogen source may include, for example, organic and inorganic compounds such as ammonium salt, nitrate, corn liquor, peptone, casein, meat extract, malt extract, soybean sediment and potato extract. The inorganic compound may include, for example, calcium chloride, sodium dihydrogen phosphate, magnesium chloride and calcium carbonate. The medium may further include yeast, vitamins, casamino acids, and growth stimulating factors. In order to facilitate the function of the promoter, agents such as 3âindolyl acrylic acid may be added as needed. The pH value of the medium may preferably be 5-8.

Cultivation of *E. coli* is usually performed at 15-45° C. for 3-75 hours, and the culture may be aerated and stirred as needed. In the case an animal cell is used as a host cell, cultivation of such transformants may be performed, for example, utilizing MEM medium, PRMI1640 medium and DMEM medium supplemented with 5-20% fetal bovine serum. The pH value of the medium may preferably be 6-8. The cultivation is usually carried out at 30-40° C. for 15-72 hours, and the culture may be aerated and stirred as needed. Extraction of culture products from the cultivated cells may be achieved by collecting the microorganisms and cells by a conventionally known method, suspending them in an appropriate buffer, disrupting the microorganisms or cells by sonication, lysozyme treatment and/or freeze-thaw, and the crude extract may be recovered by centrifugation and filtration. The buffer may contain a protein denaturing agent such as urea, and guanidine chloride; and a surfactant such as Triton X-100 (brand name) and Tween-80 (brand name). If the target product is secreted into the culture medium, on completion of cultivation, it is possible to separate the supernatant from the cells using a conventionally known method. The supernatant thus obtained or the target product contained in the extract solution may be purified by appropriately combining known methods for isolation and purification, for example, by salt dialysis using ammonium sulfate precipitation; gel filtration using Sephadex; ion exchange chromatography with a support having diethylaminoethyl group or carboxymethyl group; hydrophobic chromatography with a support having a group such as butyl group, octyl group and phenyl group; dye-gel chromatography; electrophoresis; dialysis; ultrafiltration; affinity chromatography; high performance liquid chromatography; as appropriate. Preferably, the isolation and purification can be achieved by polyacrylamide gel electrophoresis, affinity chromatography with a ligand fixed to a support, such as gelatin-agarose affinity chromatography and heparin-agarose chromatography.

Moreover, corresponding proteins introduced with mutation can be produced by substitution, deletion, insertion or transition of one or plural amino acids in the amino acid sequence constituting the soluble RAGE polypeptide, using a procedure conventionally used in genetic engineering. Introduction of such a mutation, substitution, modification may be achieved by the methods as described in Japanese Society for Biochemistry (ed.), "Continued Lecture on Biochemical Experiment 1, Genetic Study II," p. 105 (Susumu Hirose), Tokyo Chemistry Study Group (1986); Japanese Society for Biochemistry (ed.), "New Lecture on Biochemical Experiment 2, Nucleic Acid III (Recombinant DNA Technique)," p. 233 (Susumu Hirose), Tokyo Chemistry Study Group (1992); R. Wu & L. Grossman (ed.), "Methods in Enzymology," Vol. 154 p. 350 & 367, Academic Press, New York (1987); R. Wu & L. Grossman. (ed.), "Methods in Enzymology," Vol. 100, p. 457 & 468, Academic Press, New York (1983); J. A. Wells et al., Gene 34:315, 1985; T. Groundstroem et al., Nucleic Acids Res., 13:3305, 1985; J. Taylor et al., Nucleic Acids Res., 13:8765, 1985; R. Wu (ed.), "Methods in Enzymology," Vols. 155, p. 568, Academic Press, New York (1987); and A. R. Oliphant et al., Gene 44:177, 1986. The method suitable for such purpose may include, for example, site-directed mutagenesis (Zoller et al., Nucl. Acids Res. 10:6487, 1987; and Carter et al., Nucl. Acids Res., 13:4331, 1986); cassette mutagenesis (Wells et al., Gene 34:315, 1985); restriction selection mutagenesis (Wells et al., Philos. Trans. R. Soc. London Ser A.317, 415, 1986); alanine scanning (Cunningham & Wells, Science 244:1081-1085, 1989); PCR mutagenesis, Kunkel method, dNTP[αS] method (Eckstein) and site-directed mutagenesis using sulfite or nitrite.

In the protein according to this invention obtained as above, amino acid residues contained in the protein may be modified by a chemical method, otherwise subjected to enzymatic modification or partially digestion and converted into its derivatives by peptidases such as pepsin, chymotripsin, papain, bromelain, endopeptidase and exopeptidase. The protein according to this invention usually has carboxyl group (—COOH) or carboxylate (—COO⁻) at C terminal, but the C terminal can be amide (—CONH$_2$) or ester (—COOR). The R of the ester may include, for example, $C_{1-6}$ alkyl groups such as methyl, ethyl, n-propyl, isopropyl, n-butyl; $C_{3-8}$ cycloalkyl group such as cyclopentyl, cyclohexyl; $C_{6-12}$ aryl group such as phenyl, α-naphtyl; phenyl $C_{1-2}$ alkyl group such as benzyl, phenetyl; $C_{7-14}$ aralkyl group such as α-naphtyl-$C_{1-2}$ alkyl (for example, α-naphtyl methyl), in addition to pivaloyloxymethyl group, which is an ester group widely used for oral administration. If the protein according to this invention has a carboxyl group (or carboxylate) other than its C terminal, derivatives containing amide- or esterified-carboxyl group are also included in this invention. The ester available in this case may include the C terminal ester described above.

The protein according to this invention may include those in which methionine resides in the amino acid at its N terminal are protected by some protective group (for example, formyl group, $C_{1-6}$ acyl group such as $C_{1-5}$ alkyl-carbonyl group); those in which its N terminal is cleaved in vivo and/or the formed glutamyl group is pyroglutamated; in which those a substituent (for example, —OH, —COOH, amino group, imidazol group, indol group, guanidino group) existing on the side chain within the amino acid is protected by a proper protective group (for example, $C_{1-6}$ acyl group such as formyl group and acetyl group), and complex proteins such as glycoproteins conjugated with sugar chains. Moreover, when the protein according to this invention is produced by a technique of genetic engineering, it may be expressed as a fusion protein and may be converted or modified into a polypeptide exhibiting substantially equivalent biological activity with the native soluble RAGE polypeptide in vivo or in vitro. The method of fusion production conventionally utilized in genetic engineering may be adopted, such fused protein can be purified by a technique such as affinity chromatography using the fused portion. Such a fused protein may include those fused to histidine tag, and those fused to amino acid sequences of β-galactosidase (β-gal), maltose-bound protein (MBP), glutathione-S-transferase (GST), thioredoxin (TRX), and Cre recombinase. In the same manner, tags such as a heterogeneous epitope may be added to the polypeptide to achieve purification by immunoaffinity chromatography using an antibody that achieves specific binding to the epitope. In the preferred embodiment, the epitope tag may include, for example, AU5, C-Myc, CruzTag 09, CruzTag 22, CruzTag 41, Glu-Glu, HA Ha.11, KT3, FLAG (TM, Sigma-Aldrich), Omni-Probe, S-Probe, T7, Lex A., V5, VP16, GAL4 and VSV-G. Please refer to Field et al., Molecular and Cellular Biology, 8:2159-2165(1988); Evan et al., Molecular and Cellular Biology, 5:3610-3616(1985); Paborsky et al., Protein Engineering, 3(6):547-553(1990); Hopp et al., Bio-Technology, 6:1204-1210(1988); Martin et al., Science, 255: 192-194(1992); Skinner et al., J. Biol. Chem. 266:15163-15166(1991); and Lutz-Freyermuth et al., Proc. Natl. Acad. Sci. USA, 87:6393-6397(1990). The two hybrid method using yeast may be also employed. The fused proteins may be attached with some marker for detection of the protein. In a preferred embodiment, the detectable marker may be a fluorescent substance such as Biotin Avi Tag using biotin/avidin system. The fluorescent marker may include green fluorescent protein (GFP) derived from *Aequorea victorea*, or modified variants thereof (GFP variants) such as enhanced humanized GFP (EGFP), red-shift GFP (rSGFP), yellow fluorescent protein (YFP), green fluorescent protein (GFP), cyan fluorescent protein (CFP), blue fluorescent protein (BFP) and GFP from *Renilla reniformis* (Atsushi Miyazaki (ed.), "Lecture on Biochemical Experiment in Post-Genome Era 3—GFP and Bioimaging" Experimental Medicine, Suppl., Yodosha, (2000)). Detection of the fused polypeptide may be achieved by using an antibody (monoclonal antibody or its fragment) that enable specific recognition of the fusion tag.

In a preferred embodiment, a marker sequence available to achieve preferred purification, such as a marker sequence fused with hexa-histidine peptide, can be utilized. Expression and purification of such a fused protein may be achieved using a commercially available kit suitable for the purpose, in accordance with the protocol attached thereto. Modification/alteration on structure of a polypeptide may be achieved, for example, according to the methods described in Japanese Society for Biochemistry, "New Lecture on Biochemical Experiment 1, Protein VII, Protein Engineering," Tokyo Chemistry Study Group (1993), or those described in the references cited there, or any other method essentially equivalent to those methods. The biological activity of the polypeptide may include immunological activity, such as antigenicity. The modification/alteration may include de-amination, hydroxylation, phosphorylation, methylation, acetylation, ring opening, ring closure, substitution of the sugar chain contained in the protein, increase or decrease in the number of the sugar chains and substitution of amino acids to corresponding D-amino acids. Methods for such modification/alteration are well known in the field (see, for example, T. E. Creighton, "Proteins: Structure and Molecular Properties, pp. 79-86, W.H. Freeman & Co., San Francisco, USA (1983), etc.).

The human polypeptide according to this invention may differ from the native polypeptide in one or more amino acids, or the position of one or more amino acids of the human polypeptide may differ from the native polypeptide. The human protein according to this invention may include variant proteins deleted with one or more amino acids (for example, 1-80, preferably 1-60, more preferably 1-40, yet more preferably 1-20, most preferably 1-10 amino acids) in the amino acid residues characteristic in the soluble RAGE polypeptide; variant proteins substituted with one or more amino acids (e.g., 1-80, preferably 1-60, more preferably 1-40, yet more preferably 1-20, most preferably 1-10 amino acids) in the amino acid residue characteristic in the soluble RAGE; variant proteins added with one or more amino acid residues (e.g., 1-80, preferably 1-60, more preferably 1-40, yet more preferably 1-20, most preferably 1-10 amino acids) to the soluble RAGE. All of the variant proteins as described above may be included within the scope of this invention, as long as they maintain characteristic features of the native soluble RAGE polypeptide, such as the domain structure and the ligand binding ability. The soluble RAGE protein according to this invention may include proteins having substantially equivalent primary structure conformation to the native RAGE protein partly or entirely, and those exhibiting substantially equivalent biological activity to the native RAGE protein. Moreover, it may be one of the naturally occurring variants. The human protein according to this invention may include polypeptides having homology of 60%, 70% or higher depending to occasion, more preferably 80 or 90% or higher with an amino acid sequence selected from a group comprising (1) the 19th to 347th amino acid residues, (2) the 1st to 347th amino acid residues, and (3) at least the 38th to 117th and the 332nd to 347th amino acid residues in the amino acid sequence as described in the SEQ ID No. 2 of the sequence listing, particularly such polypeptides may be deleted with the transmembrane domain, and may contain an amino acid sequence comprising GluGlyPheAspLysValArg-GluAlaGluAspSerProGlnHisMet or a part thereof on the C terminal. A part of the human protein according to this invention may be any part of the peptide derived from the human protein (i.e. partial peptide of the protein), so far as it exhibits substantially equivalent biological activity with the soluble RAGE polypeptide according to this invention. For example, the partial peptide of the protein according to this invention may include peptides having amino acid sequence comprising at least five or more, preferably 20 or more, more preferably 50 or more, yet more preferably 70 or more, yet more preferably 100 or more, 200 or more in some occasion, out of the amino acid sequence of the soluble RAGE polypeptide according to this invention. Preferably such partial peptides may be those corresponding to a serial amino acid residues or, may have homology as described above on the homology of, for example, the corresponding region with the amino acid sequence as described in SEQ ID NO.2 of the sequence listing.

The term "substantially equivalent" as used herein means, for example, those having substantially equivalent inhibitory activity, physiological activity and biological activity. Furthermore, the meaning of the term may include substantially homogeneous activity, such as activity on the interaction between AGE and RAGE, for example, the binding activity to any one of the AGEs, suppressive or inhibitory effect on binding activity between the transmembrane RAGE and any one of the AGEs. Said substantially homogeneous activity means that these activities are homogeneous in properties such as physiological property, pharmacological property or biological property. For example, inhibitory activity on binding between AGE and transmembrane RAGE may be preferably equivalent (for example, approximately 0.001-1000, preferably approximately 0.01-100, more preferably approximately 0.1-20, yet more preferably 0.5-2 times), yet there may be difference on quantitative elements such as extent of these activities and molecular weight of the protein. Next, substitution, deletion or insertion of amino acids of an polypeptide do not necessarily cause significant alteration in physiological and chemical properties of the polypeptide, hence, such substituted, deleted or inserted polypeptide would be regarded substantially equivalent to the original polypeptide without substitution, deletion or insertion. In the amino acid sequence of such substituted polypeptide, the substituted amino acid substantially equivalent to the original amino acid may be selected from other amino acids included in the same class of amino acid. For example, the non-polar (hydrophobic) amino acid may be alanine, phenylalanine, leucine, isoleucine, valine, proline, tryptophan and methionine; the polar (neutral) amino acids may be glycine, serine, threonine, cysteine, tyrosine, asparagine and glutamine; amino acids with positive charge (basic amino acids) may be arginine, lysine and histidine, and amino acids with negative charge (acidic amino acids) may be aspartic acid and glutamic acid.

Synthesis of the protein according to this invention or a partial peptide thereof may achieved by any method known in this field, for example, by chemical synthesis such as liquid phase synthesis and solid phase synthesis. The method utilizes, for example, a resin for synthesis of protein or peptide, and properly protected amino acids are sequentially bonded by condensation reaction in the order of the desired amino acid sequence according to various procedures well known in this art. The condensation reaction may preferably be achieved by various activation reagents conventionally known in this art, and such reagent may preferably be, for example, carbodiimides such as dicyclohexyl carbodiimide. If the product has a protective group, removal of the protective group will result in production of the target product.

If the protein according to this invention or a partial peptide thereof is obtained as its free form, it can be converted into its salt by a known method or its modified method. On the other hand, if the protein according to this invention or a partial peptide thereof is obtained as a salt, it can be converted into a free form or another salt by a known method or its modified method. Salts of the protein according to this invention or its partial peptide may preferably be a physiologically acceptable salt or pharmacologically acceptable salt, but are not to be limited to them. The salt may be inorganic acids such as hydrochloric acid, hydrobromic acid, sulfuric acid, nitric acid and phosphoric acid; or it may be organic acid such as acetic acid, formic acid, maleic acid, fumaric acid, succinic acid, citric acid, tartaric acid, malic acid, benozoic acid, methane sulfonic acid, p-toluene sulfonic acid, benzene sulfonic acid. Moreover, the salt may be an organic base, for example, ammonium salt such as ethyl amine, dimethyl amine, trimethyl amine and hydroxyethyl amine.

The soluble RAGE polypeptide according to this invention and variants obtained by mutation, modification or derivation of the polypeptide may be subjected to separation/purification treatment in the manner as described above. The terms "fragment," "derivative," and "analog" means, in connection with the polypeptide defined in the SEQ ID No. 2 of the sequence listing, polypeptides that are transcribed from the sequence defined by the SEQ ID No. 1 of the sequence listing having undergone no splicing or polypeptides encoded by a specifically spliced hnRNA or mRNA, or polypeptides encoded by the genomic DNA, the "fragment," "derivative," and "analog" of such polypeptides described above means polypeptides exhibiting substantially equivalent biological function or activity with the original polypeptides. Therefore, the analog may include pro-proteins that produce active mature polypeptides as the result of removal of the pro-protein portions. The polypeptide according to this invention may be recombinant polypeptides, native polypeptides or synthetic polypeptides. In a particularly preferred embodiment, the polypeptides may be recombinant polypeptides.

The soluble RAGE polypeptide disclosed in the prior art is an artificial polypeptide produced from the RAGE gene having the transmembrane domain to give the extracellular domain by genetic manipulation. In contrast, the present soluble RAGE polypeptide according to this invention is a native polypeptide existing in vivo (endogenous polypeptide or intrinsic polypeptide), and these polypeptides absolutely differ in the 16 amino acid residues on its C terminal. The artificially produced soluble RAGE polypeptide disclosed in the prior art which is obtained by genetic manipulation is not native form existing in nature, and thus it is not physiological. Moreover, the previous soluble RAGE polypeptide is isolated and purified from host insect cells, therefore it is not completely free from contaminants of the host cells which can not be removed from in the process of separation/purification and may cause some immunological reaction. Moreover, the previous soluble RAGE polypeptide must be applied through a parenteral route such as an intravenous route, which is so painful and it may be burdensome to the patient. In contrast, the soluble RAGE polypeptide according to this invention is advantageous in that it exists in its native form produced endogenously, thus the polypeptide is physiological, and production of an antibody against to the polypeptide is unlikely to occur. Moreover, oral form medicine of the protein may be developed and if expression of the soluble RAGE polypeptide according to this invention can be induced by some a medicine, the patients with diabetes would be protected from complications without pain. The variants, modified compounds and derivatives obtained from the soluble RAGE polypeptide according to this invention will ensure the same advantages of the soluble RAGE polypeptide.

Meanwhile, this invention further includes DNA sequences coding for the polypeptides according to this invention, DNA sequences coding for the soluble RAGE polypeptides that maintains the native characteristic entirely or partially, as well as DNA sequences coding for the analogs and derivatives of these peptides. The polynucleotides according to this invention may encode the amino acids of the polypeptides such as the mature protein added with additional amino acids at its amino terminal or at its carboxyl terminal, or polypeptides endogenously existing in the mature protein (for example, the case that the mature polypeptide has plural polypeptide chains). Such sequence may be a sequence that exerts some function required when the precursor polypeptide is processed into the matured form polypeptide. For example, it may serve to enhance the migration or transfer of a protein, extend or shorten the half-life of the protein, or facilitate detection or production of the protein by manipulation of the protein. In general, for example, the additional amino acids may be processed by intracellular enzymes during the processing of the protein and may be removed from the mature protein. The pre-cursor protein comprising the matured form polypeptide fused with one or more additional pro-sequences may be an inactive form polypeptide. When the pro-sequence is removed, such inactive precursor usually takes its active form. Some or all of the pro-sequences may be removed prior to activation. Generally, such precursor is called to be pro-protein. The polypeptide according to this invention may be a mature protein; a mature protein added with a leader sequence (so-called pre-protein); a precursor of the mature protein comprising one or more pro-sequence(s) other than the leader sequence of pre-protein; and a pre-pro-protein which is a precursor of the pre-protein comprising a leader sequence and one or more pro-sequence(s). The pro-sequence may be removed during the step of processing required for the production of the normal active form polypeptide or mature form polypeptide.

Because the DNA sequence according to this invention provides information on a novel amino acid sequence of mammalian protein hitherto unknown, use of such information may be included within the scope of this invention. Such use of the information may include, for example, probe design used for isolation and detection of genomic DNA or cDNA coding for soluble RAGE protein and related proteins derived from a mammal, preferably from human being.

The DNA sequence according to this invention is useful as a probe for detection and isolation of the gene coding for the soluble RAGE polypeptide from a genomic DNA or cDNA prepared from a mammal such as mouse, rat and human being. The probe may be labeled with an antibody as needed and the label may be selected in relation to the antibody. Isolation of the gene may be achieved by PCR, PCR using reverse transcriptase (PCR-RT). The soluble RAGE cDNA and the related DNAs may be cloned; characteristic sequence region may be selected based on the amino acid sequence deduced from the determined cDNA sequence of the soluble RAGE polypeptide; primers may be designed and chemically synthesized; and the primers may be used for PCR, RT-PCR and other methods to be utilized for isolation, detection of the gene coding for the soluble RAGE polypeptide and the related gene. For example, the expression of mRNA coding for the soluble RAGE polypeptide in human tissues may be determined, by subjecting to northern blot analysis of poly (A)$^+$RNAs from various human tissues. Use of the cDNA according to this invention as a probe will enable detection/measurement of the expression of mRNA of the soluble RAGE polypeptide or the gene coding for the soluble RAGE polypeptide itself in human tissues, by the means of northern blotting, southern blotting and in situ hybridization. This knowledge will contribute to development of investigation on intracellular protein metabolism in human tissues, activation of hormone precursors, role of the interaction between AGE and RAGE, which are involved in various physiologic and pathologic processes in various cells including modification of tissue matrix and bones, Alzheimer disease, diabetic complications, arteriosclerosis, hyperlipidemia, allergic diseases, inflammatory diseases, neurodegenerative diseases and invasion/metastasis of cancer. Such knowledge will be useful for genetic diagnosis of diseases involved in the soluble RAGE. Such genetic diagnosis will be based on diagnosis on abnormalities, i.e. damages, mutations, reduced expression and over-expression of the gene coding for the soluble RAGE polypeptide and its related proteins.

The present invention provides a method for genetic diagnosis (detection) of the gene coding for the soluble RAGE polypeptide according to this invention. The diagnosis comprises the steps of (a) obtaining sample of a nucleic acid; (b) amplifying the nucleic acid sample obtained in the step (a) by the method of PCR, by nucleic acid amplification using RNA polymerase, or by chain replacement amplification; and obtaining amplified nucleic acid fragments by amplifying regions containing possible mutated sites existing in the soluble RAGE gene; and (c) examining on the existence of the mutation in the nucleic acid fragments obtained in step (b). The region to be tested for the presence of mutation is not to be limited to any specific region, as long as the region includes some mutation that may cause a disease. For example, the region may include any base sequence selected from the base sequence shown in the SEQ ID No. 1 of the sequence listing. In the step (c), detection of the mutation may be achieved by any method selected from conventional methods used for detection of mutation and such method is not to be specifically limited. However, such can be detected by examining DNA fragments, for example, by allele-specific PCR (ASPCR) method. The method for measuring the length of the DNA fragments is not to be specifically limited, for example, a fluorescent DNA sequencer can be used. The method available for detection of the mutation in this step may include, for example, the method based on detection of RFLP (restriction fragment length polymorphism). Alternatively, detection of a mutation may be achieved by other conventional methods such as the hybridization method using a proper DNA fragment containing the mutated site as a probe, or by SSCP (single strand conformation polymorphism) method. According to the genetic diagnosis method of the present invention, genetic diagnosis of diseases related to the soluble RAGE polypeptide of this invention can be achieved. For example, the method according to this invention enables genetic diagnosis of expression and polymorphism of the soluble RAGE polypeptide, which are assumed to be one predisposing factor that determines increased susceptibility or reduced resistance to diseases such as diabetic complications, cancer and Alzheimer disease. It will be further possible to perform a genetic therapy effective for reducing the risk of developing the above diseases based on the result of diagnosis.

The soluble RAGE polypeptide and its related proteins disclosed in this specification and their fragments, and the nucleic acids including DNA and RNA(including mRNA, and oligonucleotides) can be used alone or in a combined form, in addition, such polypeptide can be applied for genomics or proteomics technique (anti-sense method, antibodies including monoclonal antibodies, transgenic animals) in combination with the techniques described below. For example, a mutant of the soluble RAGE polypeptide will be useful for functional analysis based on dominant negative effects. A double strand RNA (dsRNA) derived from the mutated gene can be applied for the RNAi (RNA interference) technique. Therefore, the mutated gene will enable gene polymorphism analysis mainly on SNP (single nucleotide polymorphism), genetic expression analysis using a nucleic acid array or a protein array, genetic function analysis, protein-protein interaction, analysis on related diseases and analysis on therapeutic medicine. For example, according to the technique of nucleic acid array, samples can be analyzed using cDNA library, DNAs obtained by PCR technique can be arranged on a substrate using a spotting device in high density, and samples can be analyzed using hybridization. Preparation of the arrays can be performed using a needle or a pin, or using the technique of ink jet printer, by adhering the DNA on respective inherent position on the substrate such as slide glass, silicon plate and plastic plate. The data can be obtained by observation of the signals obtained as the result of the hybridization on the nucleic acid array. The signal may be derived from labels such as fluorescent dyes (for example, Cy3, Cy5, BODIPY, FITC, Alexa Fluor dyes (TM) and Texas red (TM)). Detection of the signal may be achieved with a laser scanner. And, analysis of the obtained data may be achieved by a computer system provided with a program operated in accordance with an appropriately chosen algorism. The protein array technique may utilize protein product of a recombinant expression protein added with a tag. Such technique may include two dimensional electrophoresis (2-DE); mass analysis including enzymatic digestion fragment (MS) (including electrospray ionization or ESI, matrix-assisted laser desorption/ionization or MALDI), as well as MALDI-TOF analyzer, ESI-3-tandem 4-poles analyzer, ESI-ion trap analyzer; staining; labeling by isotope for analysis; and imaging analysis technique. From the above, the present invention may include software and database related to the soluble RAGE polypeptide and its antibodies, which is obtainable and available as described above.

To transfer the DNA obtained in this invention (for example, DNA coding for the soluble RAGE polypeptide) into a target animal, the DNA can be advantageously ligated to the downstream of a promoter sequence capable of expressing the DNA in an animal cell. For example, in the case the DNA of the soluble RAGE polypeptide is transferred into a mouse, the soluble RAGE DNA obtained from an animal with high homology may be ligated downstream region of various promoters capable of being expressed in an animal cell to obtain a gene construct, then the gene construct can be micro-injected into fertilized egg of the target animal, for example fertilized egg of the mouse, thereby a transgenic mouse that achieves high-level production of the soluble RAGE polypeptide can be produced. The mouse available here is not particularly limited to pure strains, however, the mouse may include, for example, C57BL/6, Balb/C, C3H and (C57BL/6×DBA/2)F$_1$(BDF$_1$). The available promoter may include, for example, a viral promoter and promoter for ubiquitous expression such as metallothionein gene promoter. To achieve introduction of the soluble RAGE DNA, recombinant retrovirus containing the DNA can be produced. Preferably, the mouse fertilized egg introduced with the DNA can be implanted into a foster mother mouse such as ICR for development of the fertilized egg.

The DNA according to this invention (for example, DNA coding for the soluble RAGE) is transferred at the stage of development of the fertilized egg and it is ensured in the manner that the DNA exists in all germ cells and somatic cells of the target animal. The fact that DNA encoding the soluble RAGE exists in germ cells of the produced animal after DNA transfer means that all of the offsprings of the produced animals contain the DNA coding for the soluble RAGE polypeptide in all of the germ cells and somatic cells of the animal. The offsprings of such species inheriting the gene may possibly express the soluble RAGE polypeptide in all germ cells and somatic cells derived from the animal.

The transgenic animals can be mated to confirm that such transgenic animals can stably maintain the gene, and animals containing such DNA can be bread under usual breeding condition. It is further possible to obtain homozygote animals with the gene inserted into both homologous chromosomes, and the male and the female transgenic animals can be mated in order to propagate offspring in which all individual animals contain the DNA. The animals introduced with the soluble RAGE DNA exhibit over-expression of the soluble RAGE protein, therefore, such animal will be useful for the purpose to screen an inhibitor against the soluble RAGE. They will be also useful as an animal available for the purpose to screen anti-sense oligonucleotide, such as anti-sense DNA, that inhibit expression of the soluble RAGE gene.

The transgenic animal may be used as a resource of a cell line utilized in tissue culture. For example, a protein related to interaction between AGE and RAGE can be analyzed, by direct analysis on DNA or RNA existing in a tissue of the transgenic mouse, or by analysis on protein expression by these genes in a tissue. Cells derived from a tissue that produces the soluble RAGE may be cultured by a standard technique for tissue cultivation, these cells can be utilized for investigation on the functions of cells derived from various tissues, for example, cells from brain, thymus, vascular cells including vascular endothelial cell, blood cell, testicle, brain, intestine and kidney. Moreover, such cell can be utilized as a tool for development of a medicine that facilitates improvement of the function of various tissues. Techniques related to production of a transgenic mouse can be performed according to the description in literatures such as Brinster, R. L., et al., Proc. Natl. Acad. Sci. USA., 82:4438, 1985; and Constantini, F. & Jaenisch, R. (eds.), "Genetic Manipulation of the Early Mammalian Embryo," Cold Spring Harbor Laboratory, 1985, by the literatures cited in these literatures, or a modified method of the above.

It is possible to produce a gene-manupilated mouse with the gene according to this invention mutated, thereby failing to express the soluble RAGE polypeptide derived from mouse (knockout mouse). For example, a targeting vector having a mutated gene can be constructed, by inserting a gene cassette comprising an exon adjacent to the translation initiation codon locating at the center of approximately 8 kb genomic DNA containing 4 kb in the vicinity of the translation initiation codon of the gene and neo resistant gene-poly A additional signal. The gene cassette to be inserted is not limited to neo-resistant gene cassette, it may also include DT-A cassette, tk cassette and lacZ cassette. The targeting vector may be opened into a straight chain, the vector may be introduced into an established mouse embryonic stem cell (ES cell) line via electroporation, then ES cells with neo resistance may be selected by cultivation. The ES cell may be selected and produced from a mouse strain such as 129, C57BL/6 and Fl(C57BL/6×CBA). The ES cells with neo resistance is expected to have received homologous recombination with the targeting vector inserted with the gene cassette at the region of mouse soluble RAGE gene, and at least one of mouse soluble RAGE gene allele is disrupted and the mouse soluble RAGE fails to be expressed normally. The method suited for selection can be chosen according to the inserted gene cassette, and introduction of mutation can be confirmed by the methods such as PCR, southern hybridization and northern hybridization.

The ES cell introduced with mutation may be injected into 8-cell stage germ cells derived from C57BL/6, BALB/c and ICR mouse, and the germ cell is cultivated for one day to achieve development into a blastocyst, which is implanted into a foster mother such as ICR to develop into an individual. This provides chimera mouse derived from a mutated ES cell and a normal host embryo, and the proportion of the cells derived from the ES cell can be determined based on the color of the mouse. Therefore, the color of the strain of the ES cell and that of the host embryo may preferably be different. Then obtained chimera mouse are heterozygous individuals and homozygous mouse can be obtained by mating the heterozygous individuals. In the homozygous mouse thus obtained, the soluble RAGE gene of the mouse received specific disruption and fails to express the mouse soluble RAGE entirely in the germ cell and in the somatic cell, and this trait would be inherited to its offsprings.

By comparing the normal mouse with the knockout mouse, the role of RAGE and/or the soluble RAGE polypeptide in the lifecycle of an individual including development, growth, reproduction, aging and death; and the function of the soluble RAGE peptide in various organs and tissues can be elucidated. The knockout mouse will be also useful for development of a medicine related to the interaction between AGE and RAGE. The knockout mouse will be available not only as model animals for such purpose, it will be also available as a resource for tissue cultivation to be utilized for cell level functional analysis of the soluble RAGE peptide. The technique related to production of knockout mouse may be achieved by the methods described in Mansour, S. L., et al., Nature 336:348-352, 1988; Joyner, A. L. (ed.), "Gene Targeting," IRL Press, 1993; Shinichi Aizawa, "Production of Mutant Mouse Using a Gene-Targeting ES Cell," Yodo Publ. 1995, and methods mentioned in references cited therein, and their modifications.

According to this invention, it is possible to design and synthesis an anti-sense oligonucleotide (nucleic acid), which can inhibit expression of the soluble RAGE gene based on the sequence of the base sequence information of the DNA encoding the cloned or determined soluble RAGE polypeptide. Such oligonucleotide (nucleic acid) can hybridize with the mRNA of the soluble RAGE gene, thereby it can inhibit the function of the mRNA, or it can control/regulate the expression of the soluble RAGE gene via interaction with soluble RAGE related mRNA. Oligonucleotides having a sequence complementary to a selected sequence of the soluble RAGE related gene, and oligonucleotides that can specifically hybridize with the sequence of the soluble RAGE related gene will be useful to control/regulate the expression of the soluble RAGE gene in vivo and in vitro, thereby it is useful for diagnosis or treatment of diseases related to the soluble RAGE gene. In this specification, the term "correspond" means that a sequence is homologous or complementary to a nucleotide, base sequence or a certain sequence of a nucleic acid including a gene. In general, a peptide (protein) "correspond" to a nucleic acid, a base sequence or a nucleic acid means that the peptide (protein) is induced and under control of the nucleotide (nucleic acid) sequence or its complementary strand. The 5' terminal hairpin loop, 5' terminal 6-base pair repeat, 5' terminal non-translation region, polypeptide translation initiation codon, protein coding region, ORF translation initiation codon, 3' terminal non-translation region, 3' terminal palindrome region, and 3' terminal hairpin loop of the gene may be selected as a preferred target region, and any region in the gene may be selected as the target.

In the case that an oligonucleotide is complementary to a partial region of the target region of the nucleic acid of the purpose, it means that the oligonucleotide can hybridize with the target sequence, and such relation is so-called "antisense". The anti-sense oligonucleotide may include a polydeoxynucleotide comprising 2-deoxy-D-ribose, polydeoxynucleotide comprising D-ribose, another type poly-nucleotide comprising N-glycoside of purine or pyrimidine base, polymer containing a non-nucleotide skeleton (for example, commercially available protein nucleic acids and nucleic acid polymers specific to synthetic sequence), and other polymers containing a special bonding (with the proviso that the polymer contains a polynucleotide having an arrangement that permits base pairing or base attachment observed in DNA and RNA). The oligonucleotide may include double stranded DNA, single stranded DNA, double stranded RNA, single stranded RNA or DNA/RNA hybrid; unmodified polynucleotides or unmodified oligonucleotides; oligonucleotides added with modification known in this field, for example, such as by labeling, capping, methylation; oligonucleotides obtained by substituting one or more native nucleotides by their analogs; oligonucleotides with a nucleotide in its molecular modified; for example, oligonucleotides having a non-charged bonding (for example, methylphosphonate, phosphotriester, phosphoramidate and carbamate); oligonucleotides having a charged bonding or a bonding containing sulfur (for example, phosphorothioate and phosphorodithioate); oligonucleotides having side chain group of a protein (for example, nuclease, nuclease inhibitor, toxin, antibody, signal peptide and poly-L-lysine) or sugars (for example, monosaccharide); oligonucleotides having intercurrent compounds (for example, acridine and psoralen); oligonucleotides having chelate compounds (for example, metal, radioactive metal, boron and acidic metal); oligonucleotides containing an alkylating agent; oligonucleotides having a modified bonding (for example, α-anomeric nucleic acid). The terms "nucleoside," "nucleotide," and "nucleic acid" as used herein mean not only conventionally known compounds containing purine or pyrimidine bases but also the other compounds with modification such as those having heterocyclic base. The modification may include methylated purine or pyrimidine, acylated purine or pyrimidine, or those containing other heterocyclic ring. The sugar portion of the modified oligonucleoside and the modified oligonucleotide may be modified; for example, one or more hydroxyl groups may be substituted by a halogen or by an aliphatic group, otherwise may be substituted by functional groups such as ether and amine.

The anti-sense nucleic acid according to this invention may include RNA, DNA and a modified nucleic acid. The modified nucleic acid sequence may include, for example, sulfur derivatives of a nucleic acid and thiophosphate derivatives, in addition to polynucleoside amides or oligonucleoside amides having resistance to decomposition, but it is not to be limited to them. Preferably, the anti-sense nucleic acid according to this invention can be designed as follows. That is, it may be designed to enhance the stability of the anti-sense nucleic acid in a cell; the cellular permeability of the oligonucleotide; or the affinity of the oligonucleotide to the target sense sequence. If the oligonucleotide exhibits some toxicity, the modification should reduce the toxicity.

Many kinds of such modification are known in this field, for example, as disclosed in J. Kawakami et al., Pharm. Tech. Japan 8:247, 1992; 3:395, 1992; and S. T., Crooke et al. (ed.), "Antisense Research and Applications," CRC Press, 1993. The anti-sense nucleic acid according to this invention may be altered; or may contain a modified sugar, base or bonding; it may be provided as a special form such as liposomes and microspheres; or it may be applied for gene therapy; or it may be provided as an added form. Those utilized as such added form may include polycation compounds such as polylysine serving to neutralize the electric charge of the phosphate group backbone; or hydrophobic compounds such as lipids (for example, phospholipid, cholesterol and etc.) serving to promote the interaction with cell membrane, or to increase the incorporation of the nucleic acid. The lipid to be used for the purpose of such addition may include cholesterol and its derivatives (for example, cholesterylchloroformate and cholic acid). Such compounds may be attached via 3' or 5' terminal of a nucleic acid, and they may be attached via a base, a sugar or an intramolecular nucleoside binding. Other groups may include a group specifically arranged at 3' or 5' terminal of an oligonucleotide for the purpose of capping, thereby preventing digestion by nuclease such as exonuclease and RNase. Such groups for capping may include conventionally known hydroxyl protective groups such as glycols including polyethylene glycol, tetraethylene glycol, etc., but it is not to be limited to them.

Inhibitory effect of an anti-sense nucleic acid can be examined using a transformant according to this invention, in-vivo or in-vitro gene expression system according to this invention, or in-vivo or in-vitro translation system the soluble RAGE gene. The nucleic acid itself can be applied to a cell by various known methods.

According to the result of the investigation as described above, the present invention provides a method comprising the steps of introducing the soluble RAGE gene and a recombinant DNA molecular into a host; allowing the expression of the soluble RAGE polypeptide; and obtaining the soluble RAGE polypeptide of the purpose. The present invention also provides a transformant or a transfectant capable of substantially expressing the soluble RAGE gene, a method for producing the transformant or transfectant, as well as use of the transformant or transfectant.

In a further aspect, this invention relates to the native soluble RAGE that belongs to RAGE family (especially endogenous soluble RAGE), and this invention relates to a nucleic acid such as DNA or RNA capable of expressing, in a prokaryotic cell such as *E.coli* or in a eucaryotic cell such as mammalian cell, a polypeptide comprising at least a part or entirely of a protein, the protein having activity toward interaction between AGE and RAGE (for example, suppressive or inhibitory effect on binding AGE and membrane-bound type RAGE), and one of the polypeptides having a serial amino acid sequence comprising at least 1 to 16 amino acid residues out of $Glu^{332}$ to $Met^{347}$ of the amino acid sequence described in the SEQ ID No. 2 of the sequence listing at its C terminal, still having substantially equivalent activity with the native human soluble RAGE polypeptide and its salt, more preferably those having substantially equivalent activity or substantially equivalent primary conformation with the soluble RAGE or its salt. Moreover, the nucleic acid, especially DNA, may comprise (a) a sequence encoding an amino acid sequence as described in SEQ ID No. 2 of the sequence listing, or a sequence complementary to said sequence; (b) a sequence that hybridizes with the DNA sequence (a) or its fragment; and (c) a sequence containing degenerated codons that hybridizes to said sequences (a) or (b). Here, the condition for hybridization should be a stringent condition. A prokaryotic cell such as *E. coli* or a eukaryotic cell such as a mammalian cell, which are transformed with the above nucleic acid sequence and capable of expressing a polypeptide of this invention, are also included within the aspect of this invention.

A typical object of this invention is to provide a prominent method for detection/determination of the soluble RAGE polypeptide or its gene in a test sample, as well as RAGE producing cell and a reagent kit for detection of the above, using the soluble RAGE gene and a probe derived from the gene, or optionally using an inhibitor against the soluble RAGE polypeptide. The embodiment according to this invention should be comprehended to include all of the reagents used in a reagent kit that enables detection and determination of the soluble RAGE polypeptide or its gene, or the RAGE producing cell. Furthermore, another object of this invention is to provide a method, a reagent or a diagnostic reagent available for monitoring the role of interaction between AGE and RAGE, which is involved in many processes occurring in the normal cell such as intracellular protein metabolism, activation of hormone precursors and alteration of tissue matrix and bones, and various diseases such as diabetic complications, arteriosclerosis, thrombosis, hyperlipidemia, Alzheimer disease, allergic diseases, inflammatory diseases, osteoporosis, neural degenerative diseases and invasion/metastasis of cancer. This invention and its embodiments may include various use of above-mentioned reagents in the field of medicine and physiology, as well as use of such reagents for the purpose of investigation, analysis, measurement, diagnosis, prevention and treatment on the responses, symptoms, diseases caused by the interaction between AGE and RAGE.

The soluble RAGE polypeptide according to this invention and its salt exhibits activity on the interaction between AGE and RAGE, for example, it exhibits suppressive or inhibitory activity on binding AGE to transmembrane-type RAGE, which is assumed to be an important factor, for example, in defense of a living body, aging, development of adult vascular disorders and cancer. The protein may be effective for the treatment of patients with soluble RAGE polypeptide-related functional disorders, i.e. patients showing symptoms such as soluble RAGE aplasia, soluble RAGE hypogenesis and soluble RAGE deficiency. That is, the use of a medicine, containing the soluble RAGE polypeptide, its mutated compound, its modified compound or its derivative, will enable treatment of patients suffering from deficiency in the activity of the soluble RAGE polypeptide. The polypeptide according to this invention is one of AGE inhibitors, thus it would be useful as a medicine for treatment and/or prevention of various disorders caused by decreased expression of the protein or decreased inhibitory effect on the AGE action. Moreover, the polypeptide according to this invention would be useful as a medicine for treatment and/or prevention of various disorders caused by increased AGE activity. For example, in the case of patients with insufficient or abnormal cellular RAGE biological activity caused by in vivo decrease or deficiency in the soluble RAGE polypeptide, the symptoms in the patients may be improved via supplying the protein according to this invention in vivo by the means of (A) administrating the polypeptide of this invention to the patients, (B) administrating a nucleic acid such as the DNA according to this invention to the patient for in vivo expression of the protein according to this invention, or (C) transplanting with a cell introduced with a nucleic acid such as DNA according to this invention to enable its expression, into a patient.

Compounds (agonists or stimulants) enhancing the biological activity (for example, the activity to suppress or inhibit the binding between the AGE and the transmembrane-type RAGE) of the soluble RAGE polypeptide according to this invention or salts thereof may be used as useful medicine for treating and/or preventing various diseases such as deficiency in the soluble RAGE function, diabetic complications, arteriosclerosis, thrombosis, hyperlipemia, Alzheimer disease, neural degenerative diseases, rheumatoid arthritis and invasion/metastasis of cancer. On the other hand, compounds (antagonists or inhibitors) inhibiting biological activity (for example, the activity to suppress or inhibit the binding between the AGE and the transmembrane-type RAGE) of the soluble RAGE polypeptide according to this invention may be used as useful medicine for treating and/or preventing various diseases such as soluble RAGE polypeptide over-expression disorder, disorders or diseases caused by the interaction between AGE and RAGE and cancer. Because the soluble RAGE polypeptide suppresses or inhibits the physiological or biological activity of AGE, the soluble RAGE polypeptide will be effective as a medicine for treatment of diseases resulting from the over-production of AGE.

Then the soluble RAGE polypeptide according to this invention will serve as a reagent for screening a compound (or a salt thereof) that stimulatory (agonist) or inhibitory (antagonist) on the biological function (for example, the activity to suppress or inhibit the binding between the AGE and the transmembrane-type RAGE) of the soluble RAGE polypeptide. Namely, this invention also provides a method for screening a compound (or a salt thereof) having stimulatory (agonist) or inhibitory (antagonist) effect on the biological function (for example, the activity to suppress or inhibit the binding between the AGE and the transmembrane-type RAGE) of the soluble RAGE polypeptide according to this invention, a partial peptide thereof, or a salt thereof, using the soluble RAGE polypeptide according to this invention, a partial peptide thereof, or a salt thereof.

In the screening, comparison is performed between the following two samples, for example (i) contacting the protein according to this invention, a partial peptide thereof, or a salt thereof (including a transformant capable of expressing the protein, and so on) with a substrate such as AGE, (ii) contacting the protein according to this invention, a partial peptide thereof, or a salt thereof with the substrate and (in the presence of) a test sample. In concrete, in the screening described above, the biological activity (for example, an activity related to interaction between AGE and RAGE) was measured and compared. The screening may be performed in the presence of the transmembrane-type RAGE polypeptide.

The substrate may include any molecule, as long as they can serve as a substrate of AGE etc. For example, the substrate may be chosen from those available for measurement of the interaction between AGE and RAGE, but preferably it may be a synthesized AGE. The substrate may be used as it is, preferably it may be used in combination with a labeling such as by fluoresent labeling by fluorescein, enzyme labeling and radioisotope labeling.

The test sample may include, for example, a protein, a peptide, a non-peptide compound, a synthetic compound, a fermentation product, a plant extract, a tissue extract from an animal and a cell extract. A test compound used as a test sample may preferably be an anti-AGE antibody, an anti-RAGE antibody, an inhibitor of AGE—RAGE binding, a compound having inhibitory activity on protein glycation, especially it may include a synthetic compound. These compounds may be a novel compound, or a known compound. The screening may be performed according to any method conventionally known in the field used for measurement of binding activity. Moreover, various labeling, buffer systems or other appropriate reagents may be used, and may be performed as described in the accompanying document. The peptide to be used may be subjected to treatment by an activating agent, or the precursor or the pro-form may be converted into an active form prior to use. The measurement may be performed in a buffer unlikely to exert an adverse effect on the reaction system such as tris-hydrochloric buffer and phosphate buffer, for example, in a buffer of pH4-10 (preferably pH6-8). In the individual screening, technical consideration of a skilled artisan may be paid on the operating procedures, to construct an assay system in relation to the soluble RAGE polypeptide according to this invention, or a polypeptide or a peptide having substantially equivalent activity to the soluble RAGE polypeptide according to this invention. The details of the conventional technique in this field can be seen in reviews and monographs specialized in the field (see, for example, "Methods in Enzymology," Academic Press, USA).

The compound or its salt obtainable by the screening method or with a screening kit according to this invention may include a test compound described above, for example, may be a compound selected from peptides, proteins, non-protein compounds, synthetic compounds, fermentation products, cell extracts, plant extracts, extracts obtained from animal tissues, or a compound that enhances or inhibits the function of the protein according to this invention. A salt of the compound may be, for example, a pharmaceutically acceptable salt. For example, the salt of the compound may include a salt with an inorganic base, a salt with an organic base, a salt with an inorganic acid, a salt with an organic acid, and a salt with a basic or an acidic amino acid. The preferred salt with inorganic base may include, for example, alkali metal salts such as sodium salt and potassium salt; alkali earth metal salts such as calcium salt and magnesium salt; aluminum salt; and ammonium salt. The preferred salt with organic base may include, for example, a salt with trimethylamine, triethylamine, pyridine, picoline, 2,6-lutidine, ethanolamine, diethanolamine, triethanolamine, cyclohexylamine, dicyclohexylamine and N,N'-dibenzylethylenediamine. The preferred salt with inorganic acid may include, for example, a salt with hydrochloric acid, hydrobromic acid, sulfuric acid and phosphoric acid. The preferred salt with organic acid may include, for example, a salt with formic acid, acetic acid, propionic acid, fumaric acid, oxalic acid, tartaric acid, maleic acid, citric acid, succinic acid, malic acid, methane sulfonate, benzene sulfonate and benzoic acid. The preferred salt with basic amino acid may include, for example, a salt with arginine, lysine and ornithine. The preferred salt with acidic amino acid may include, for example, a salt with aspartic acid and glutamic acid.

The term "antibody" as used herein is meant to cover in a wide range of meaning, and it may include a single chain monoclonal antibody against the desired soluble RAGE polypeptides or their related peptide fragments, or it may include antibody compositions specific to various kinds of epitopes, or it may include monovalent antibodies or multivalent antibodies, as well as polyclonal antibodies and monoclonal antibodies. The term "antibody" may further represent an intact molecule and its fragments and derivatives, including fragments such as F(ab')$_2$, Fab' and Fab. The "antibody" may further include chimera antibodies or hybrid antibodies having at least two antigen or epitope binding sites or, for example, double specific recombinant antibodies such as quadrome and triome; interspecies hybrid antibodies; anti-idiotype antibodies; and derivatives of said antibodies obtained by chemically modification or processing; antibodies obtained by applying conventional techniques such as cell fusion, hybridoma production and antibody engineering; antibodies produced by synthetic or semi-synthetic techniques; antibodies produced by applying techniques conventionally utilized in the terms of antibody production and recombinant DNA techniques; and antibodies having neutralizing properties or binding properties to the target antigenic substance or to the target epitope. The most preferred antibody according to this invention includes one that allows specific recognition of the native soluble RAGE polypeptide, for example, one that enables distinction from the full-length RAGE polypeptide or the publicly known soluble RAGE polypeptide obtained by cleaving the N terminal or C terminal side from the full-length RAGE polypeptide.

A monoclonal antibody against the antigenic substance may be produced using an arbitrary method that can provide production of antibody molecules by a serial cell line in the cultivation. The term "monoclonal" as used herein means characteristic of the antibody that the antibody consists of substantially homologous mass of antibodies, and thus it should not be understood that such antibodies needs to be produced by some specific procedure. The individual antibody contains a population of monoclonal antibodies consisting of essentially identical properties, except that little amount of naturally occurring native variants may exist. The monoclonal antibody is highly specific to its antigen, and it is directed to a sole antigen determinant site. In contrast with the conventional polyclonal antibody preparations typically consisting of various antibodies directed to different antigenic determinants (epitopes), each of the monoclonal antibody is directed to a singular antigenic determinant on the antigen. In addition to such specificity, monoclonal antibodies are generally produced via hybridoma cultivation, and thus monoclonal antibodies are superior in that they contain no or little contaminants of other immunoglobulins. The monoclonal antibodies may include hybrid antibodies or recombinant antibodies. Such antibodies can be obtained by substituting the variable domain of an antibody with the constant domain (for example, humanized antibody), by substituting the light chain of an antibody with the heavy chain, by substituting one chain of a certain species with that derived from another species, or by producing a fusion protein with a heterogeneous protein, regardless of the origin or differences in immunoglobulin class or subclass, as far as they exhibit the desired biological activity (see, for example, U.S. Pat. No. 4,816,567; "Monoclonal Antibody Production Techniques and Applications, pp. 79-97, Marcel Dekker, Inc., New York, 1987, etc.). A preferred method for production of monoclonal antibodies may include hybridoma method (G. Kohler and C. Milstein, Nature 256, pp. 495-497, 1975); human B cell hybridoma method (Kozbor et al., Immunology Today, 4:72-79, 1983; Kozbor, J. Immunol., 133:3001, 1984; and Brodeur et al., "Monoclonal Antibody Production Techniques and Applications," pp. 51-63, Marcel Dekker, Inc., New York (1987)); trioma method; and EBV-hybridoma method (Cole et al., "Monoclonal Antibodies and Cancer Therapy," Alan R. Liss, Inc., pp. 77-96(1985) ("A method for production of human single chain monoclonal antibodies"); as well as U.S. Pat. No. 4,946,778("A technique for production of single chain antibodies"). In addition, following references can be listed in connection with antibodies: S. Biocca et al., EMBO J., 9:101-108 1990; R. E. Bird et al., Science, 242:423-426 1988; M. A. Boss et al., Nucl. Acids Res., 12:3791-3806 1984; J. Bukovsky et al., Hybridoma 6:219-228 1987; M. Daino et al., Anal. Biochem. 166:223-229 1987; J. S. Huston et al., Proc. Natl. Acad. Sci. USA, 85:5879-5883 1988; P. T. Jones et al., Nature 321:522-525 1986; J. J. Langone et al. (eds.), "Methods in Enzymology," Vol. 121 (Immunochemical Techniques. Part I: Hybridoma Technology and Monoclonal Antibodies), Academic Press, New York (1986); S. Morrison et al., Proc. Natl. Acad. Sci. USA, 81:6851-6855 (1984); V. T. Oi et al., BioTechniques 4:214-221 1986; L. Reichmann et al., Nature 332:323-327 1987; A. Tramontano et al., Proc. Natl. Acad. Sci. USA 83:6736-6740 1986; C. Wood et al., Nature 314: 446-449 1985; and Nature 314:452-454 1985, and references cited therein (all the references will be incorporated herein by way of citation).

The monoclonal antibody according to this invention is identical or homologous with the counterpart sequence of antibody which part of the heavy chain and/or the light chain is derived from a certain species, or belongs to a specific anti-body class or subclass, as far as exhibiting desired biological activity. Meanwhile, the monoclonal antibody according to this invention particularly include a "chimera antibody" in which the residual part of the chain is identical or homologous with the counterpart sequence of an antibody that belongs to another antibody class or subclass derived from another species (see U.S. Pat. No. 4,816,567; and Morrison et al., Proc. Natl. Acad. Sci. USA, 81:6851-6855 1984).

Production of an antibody according to this invention will be detailed below, with the example of production of the monoclonal antibody. The monoclonal antibody according to this invention may include monoclonal antibodies obtainable by cell fusion technique using myeloma cells, and may be produced via following steps.
1. Preparation of an immunogenic antigen
2. Immunization of an animal with the immunogenic antigen
3. Preparation of a myeloma cell (bone marrow tumor)
4. Cell fusion of the antibody producing cell with the myeloma cell
5. Selection of hybridoma (fused cell) and cloning
6. Production of monoclonal antibodies 1. Preparation of an Immunogenic Antigen As described above, the soluble RAGE polypeptide or fragments derived from it may be used as the antigen, but an appropriate oligopeptide may be chemically synthesized based on the information of the determined amino acid sequence of the soluble RAGE polypeptide and it can be utilized as the antigen. Typically, such peptide may be a peptide comprising at least five serial amino acid residues existing in the region selected from a group consisting of the following amino acid sequences of the sequence described in SEQ ID NO;2 of the sequence listing:
(1) amino acid sequence comprising at least 332nd to 347th amino acid residues;
(2) amino acid sequence comprising 1st to 117th amino acid residues;
(3) amino acid sequence comprising 19th to 347th amino acid residues; and
(4) amino acid sequence comprising 1st to 347th amino acid residues.

The antigen may be mixed with a proper adjuvant and it may be used to immunize an animal, and then it may be made to be an immunogenic conjugate. For example, the antigen serving as an immunogen may be a fragmented soluble RAGE polypeptide, or it may be a synthetic polypeptide fragment obtained by synthesizing a polypeptide designed based on the characteristic region selected according to the amino acid sequence. Moreover, the fragment can be bound to various carrier proteins via some proper condensing agent to produce an immunogenic conjugate such as hapten-protein conjugate and it may be utilized to design a monoclonal antibody capable of reacting with a certain specific sequence (or capable of recognizing a specific sequence). The polypeptide to be designed may be added with cysteine residues in advance, in order to facilitate preparation of the immunogenic conjugate. Prior to binding with the carrier protein, the carrier protein may be activated at first. The activation may be achieved by introduction of an activated binding group to the protein.

The activated binding group may include: (1) activated esters and activated carboxyl groups such as nitrophenylester group, pentafluorophenylester group, 1-benzotriazolester group, N-succinimideester group, and (2) activated dithio group such as 2-pyridylthio group. The carrier protein may include keyhole limpet hemocyanin (KLH), bovine serum albumin (BSA), egg white albumin, globulin, polypeptide such as polylysine and bacterial component such as BCG.

2. Immunization of an Animal with the Immunogenic Antigen

Immunization of an animal may be achieved by any method known to a skilled artisan, for example, according to a method described in Shigeru Muramatsu (ed.), "Lecture on Experimental Biology 14-Immunobiology," Maruzen, 1985; Japanese Society for Biochemistry (ed.), "Continued Lecture on Biochemical Experiment 5-Research Method of Immunobiochemistry," Tokyo Chemistry Study Group, 1986; and Japanese Society for Biochemistry (ed.), "New Lecture on Biochemical Experiment 12-Molecular Immunology III, Antigen/Antibody/Complement," Tokyo Chemistry Study Group, 1992. Immunization may be achieved by injecting an immunization agent (in combination with an adjuvant as needed) into a mammal one or plural times. Typically, immunization can be achieved by plural administration of an immunization agent and/or an adjuvant into a mammal via subcutaneous or intraperitoneal injection. The immunization agent may contain said antigenic polypeptides or its related peptide fragments. The immunization agent may be used after conjugate formation with a protein, (for example, said carrier protein) known to be immunogenic to the mammal to be immunized. The adjuvant may include, for example, Freund's complete adjuvant, Ribi adjuvant, pertussis vaccine, BCG, lipid A, liposome, aluminum hydroxide and silica. Immunization may be achieved using an appropriate animal, for example, a mouse such as BALB/c and hamster. In the case of mouse, the dose of the antigen to be administrated may be 1-400 µg per an animal, and it may be generally administrated via interperitoneal or subcutaneous route at the interval of 1-4 week, preferably at the interval of 1-2 week, then additional immunization may be repeated 2 to 10 times via intraperitoneal, subcutaneous, intraveneous or intramuscular route. As the mouse to be immunized, BALB/c mouse or F1 mouse derived from BALB/c mouse and a mouse of other line may be adopted. The system for measurement of the antibody titer may be prepared in needed, and the extent of the immunization may be confirmed by measuring the titer of the immunized animal. The antibody according to this invention may be obtained from an animal thus immunized and it may include, for example, antisera and polyclonal antibodies.

3. Preparation of Myeloma (Bone Marrow Tumor) Cell Line

The immortal cell line (tumor cell line) to be used for cell fusion may be selected from cell lines incapable of immunogloblin production, for example, P3-NS-1-Ag4-1 (NS-1, Eur. J. Immunol., 6:511-519 1976); SP-2/0-Ag14 (SP-2, Nature 276:269-270, 1978); P3-X63-Ag8-U1 derived from mouse myeloma cell line MOPC-21 (P3U1, Curr. Topics Microbiol.

Immunol. 81:1-7, 1978); P3-X63-Ag8 (X63, Nature, 256: 495-497, 1975); and P3-X63-Ag8-653 (653, J. Immunol., 123:1548-1550, 1979). The 8-azaguanine resistant mouse myeloma cell line may be sub-cultured in a culture medium such as Dulbecco MEM medium (DMEM medium) and RPMI1640 medium, supplemented with antibiotics such as penicillin and amikacin, fetal calf serum (FCS), and 8-azaguanine (for example, 5-45 μg/ml), then required number of cells may be prepared by transferring the cells into a normal medium, two to five days prior to cell fusion. The frozen cell line may be completely thawed at about 37° C., then it may be washed three times or more and it may be grown on a normal medium until a desired number of cells is obtained.

4. Cell Fusion of Antibody Producing Cell with Myeloma Cell

An animal such as mouse may be immunized according to the step 2 as described above, the spleen of the animal may be isolated two to five days after the last immunization, and suspension of the spleen cell may be obtained. In addition to the spleen cell, lymph node cells of various portions of the living organism may be obtained and they may be used for cell fusion. The spleen cell suspension thus obtained, together with the myeloma cell line obtained in the step 3, may be applied into a cell medium such as minimum essential medium (MEM), DMEM and RPMI-1640 medium, and a cell fusion agent such as polyethylene glycol may be added to the culture. The cell fusion agent may include any one conventionally known in the field such as inactivated Sendai virus (Hemagglutinating virus of Japan, HVJ). Preferably, 0.5-2 ml of 30-60% polyethylene glycol may be added. Preferably, polyethylene glycol used may have a molecular weight of 1,000-8,000, more preferably it may have a molecular weight of 1,000-4,000. The concentration of polyethylene glycol in the fusion medium may be kept preferably, for example, at 30-60%. A small amount of dimethylsulfoxide may be added as needed to facilitate cell fusion. The ratio of cells to be used for cell fusion, i.e. spleen cells (lymphocytes): myeloma cells, may preferably kept at 1:1 to 20:1, more preferably 4:1 to 7:1.

The fusion reaction may be allowed to occur for 1-10 minutes, then cell medium such as RPMI-1640 medium may be added. Cell fusion treatment may be repeated plural times. After completion of the cell fusion treatment, the cell is subjected to separation by centrifugation, then the separated cells may be transferred to a selection medium.

5. Selection of Hybridoma (Fused Cell) and Cloning

The selection medium may include FCS containing MEM medium or RPMI-1640 medium supplemented with hypoxanthine, aminopterin and thymidine, so-called HAT medium. The method for replacement of the selective medium may be as follows. In general, fresh medium corresponding to the volume dispensed into a culture plate may be added at the next day, then it may be repeatedly replaced with the half volume of HAT medium at 1-3 days interval, however, this procedure can be modified as needed. Eight to 16 days after the fusion, replacement of culture medium may occur by using aminopterin-free medium so-called HT medium at 1-4 days interval. For example, mouse thymocytes may be used as a feeder to give a good result.

Supernatant may be sampled from culture well exhibiting excellent hybridoma growth, and the supernatant may be screened by radioimmunoassay (RIA), enzyme-linked immunosorbent assay (ELISA), fluorescent immunoassay (FIA) or fluorescence-activated cell sorter (FACS), using the peptide fragment of interest as an antigen, or determining the target antibody using a labeled anti-mouse antibody, The hybridoma producing the target antibody may be cloned. Cloning of the hybridoma may be achieved by picking up the target colony on an agar plate, or by limiting dilution. Preferably, limiting dilution may be employed. Preferably, cloning may be repeated plural times.

6. Production of Monoclonal Antibody

The hybridoma obtained may be cultured on a proper growth medium for proliferation such as FCS-containing MEM medium and RPMI-1640 medium, and the monoclonal antibody of the purpose can be obtained from the medium supernatant. For massive production of an antibody, the hybridoma may be obtained as an abdominal dropsy. In this case, hybridoma may be transferred into abdominal cavity of an animal exhibiting the same histocompatibility with the animal from which the hybridoma has been obtained, then it may be proliferated and the monoclonal antibody produced in the animal may be recovered from the abdominal cavity of the animal. Prior to transplantation of the hybridoma, a mineral oil such as pristane (2,6,10,14-tetramethylpentadecane) may be administrated via interperitoneal route. After the treatment, hybridoma may be proliferated and the abdominal dropsy may be recovered. The abdominal dropsy may be used as it is, or may be purified by a conventional method such as salt dialysis using ammonium sulfate precipitation, gel filtration using Sephadex resin, ion exchange chromatography, electrophoresis, dialysis, ultra-filtration, affinity chromatography and high performance liquid chromatography, to produce monoclonal antibodies. Preferably, the abdominal dropsy containing monoclonal antibodies may be subjected to ammonium sulfate precipitation; then the precipitate may be applied to an anion exchange gel such as DEAE-Sepharose or an affinity column such as protein A column to perform purification treatment. Preferably the purification may be achieved by an affinity chromatography immobilized with antigen or antigen fragment (for example, synthetic peptide, recombinant antigen protein or peptide, antigen specific recognition site), or by affinity chromatography immobilized with protein A or hydroxyappatite chromatography.

Moreover, a transgenic mouse or other animals such as other mammals may be utilized to achieve expression of antibodies, such as humanized antibody, against immunogenic polypeptide product according to this invention.

The antibody can be also produced according to the genetic recombination technique, by determining the amino acid sequence of the antibody thus obtained at large scale, or by utilizing nucleic acid sequence coding for the antibody derived from the hybridoma strain. The nucleic acid coding for the monoclonal antibody may be isolated and determined according to the conventional techniques, for example, by utilizing oligonucleotide probe capable of specific binding to the gene encoding the heavy chain or light chain of the mouse antibody. Once the DNA has been isolated, it may be inserted into an expression vector as described above, and then it may be introduced into host cell such as CHO or COS cell. The DNA may be modified by replacement of homogeneous mouse sequence with constant region of human heavy chain and light chain (Morrison et al., Proc. Natl. Acad. Sci. USA, 81:6581, 1984). Namely, it is possible to produce a chimera antibody or hybrid antibody exhibiting the desired binding specificity. It is also possible to modify the given antibody using chemical technique for protein synthesis including adoption of condensing agents as described below, to produce a chimera or hybrid antibody.

Preparation of a humanized antibody may be achieved by any method known in the field (see, for example, Jones et al., Nature, 321:522-525 1986; Riechmann et al., Nature, 332:

323-327 1988; and Verhoeyen et al., Science, 239:1534-1536 1988). Preparation of a human monoclonal antibody may be also achieved by a method known in the field. Indeed, human myeloma cells and human/mouse heteromyeloma cells available for the production of human monoclonal antibodies are known in the field (Kozbor, J. Immunol., 133:3001, 1984; and Broedeur et al., "Monoclonal Antibody Production Technique and Applications," pp. 51-63, Marcel Dekker, Inc., New York (1987)). A method for preparation of a bi-specific antibody is also known in the field (Millstein et al., Nature, 305:537-539 1993; WO93/08829; Traunecker et al., EMBOJ., 10:3655-3659 1991; and Suresh et al., "Methods in Enzymology," Vol. 121, p. 210, (1986)).

Furthermore, the antibody may be treated with an enzyme such as trypsin, papain and pepsine, in some cases, antibody fragments such as Fab, Fab', F(ab')$_2$ may be also utilized.

The antibody may be used for any assay conventional known in this field, for example, direct competitive binding assay, direct or indirect sandwich ELISA assay and immunoprecipitation assay (Zola, "Monoclonal Antibodies: A Manual of Techniques, pp. 147-158, CRC Press, Inc., (1987)).

To achieve conjugation of an antibody to a detectable atomic group, conventional known methods in this field may be utilized. The examples of such method are described in David et al., Biochemistry, 13:1014-1021 1974; Pain et al., J. Immunol. Meth., 40:219-231 1981; and in "Methods in Enzymology," Vol. 184, pp. 138-163 (1990). An antibody to be labeled may include IgG fraction and Fab' which is a specific antigen binding site obtained by pepsin digestion succeeded by its reduction. The labeling may include an enzyme (for example, peroxidase, alkaliphosphatase and β-D-galactosidase), a chemical substance, a fluorescent substance and a radioisotope.

The detection/assay according to this invention may include immunostaining such as tissue staining and cell staining, immunoassay such as competitive or non-competitive immunoassay, radioimmunoassay and ELISA, and the measurement may be performed with or without B-F separation. The preferred assay includes radioimmunoassay, enzyme-linked immunosorbent assay and sandwich ELISA. For example, in the sandwich ELISA, one antibody may be prepared as an antibody specific to the soluble RAGE polypeptide of the present invention or its related polypeptide, and another antibody may be prepared as an antibody specific to C terminal residue of the soluble RAGE polypeptide, and one antibody may be labeled to enable detection. Another antibody that can recognize the same antigen may be immobilized to a solid support. A sample, the labeled antibody and the immobilized antibody may be incubated to allow sequential reaction; unbound antibodies may be removed; and the amount of labeled products may be determined. The amount of the labeled products thus determined correlates with the amount of antigen, i.e. the amount of the soluble RAGE polypeptide fragment antigen. This assay may be called simultaneous sandwich assay, forward sandwich assay or reverse sandwich assay, depending on the order of the addition of antibodies such as immobilized antibody and labeled antibody. Operations such as washing, stirring, vibration, filtration and pre-extraction of the antigen may be adopted in the measurement steps under certain circumstances, if necessary. The assay conditions, such as use of a certain reagent, concentration of a buffer, temperature and time for incubation, may be altered depending on the concentration of antigen in the sample or on the property of the sample. Those skilled in the art could easily determine an optimal condition ad libitum for a given assay utilizing conventional experimental method.

Support to which an antibody can be immobilized includes many known supports, and the assay of this invention may employ any one from among them ad libitum. The support utilized for antigen-antibody reaction may include many known supports. The assay according to this invention may employ any one out of those publicly known supports. The particularly preferred support may include, for example, those made from glass such as activated glass; porous glass; silica gel; silica-alumina; alumina; inorganic materials such as magnetized iron and magnetized alloy; polyethylene; polypropylene; polyvinyl chloride; polyvinylidene fluoride; polyvinyl acetate; polymethacrylate; polystyrene; styrene-butadiene copolymer; polyacrylamide; cross-linked polyacrylamide; styrene-methacrylate copolymer; polyglycidyl-methacrylate; acrolein γ-ethyleneglycol dimethacrylate copolymer; cross-linked albumin; collagen; gelatin; dextran; agarose; cross-linked agarose; natural or degenerated celluloses such as microcrystalline cellulose, carboxymethyl cellulose and cellulose acetate; cross-linked dextran; polyamides such as nylon; organic polymers such as polyurethane and polyepoxy resin; compounds obtained by emulsified polymerization of any of above substances; cell; erythrocyte; compounds having a functional group in need introduced via silane coupling agent.

The solid support may further include filter; beads; the internal wall of a test vessels, for example, test tube, titer plate and titer well; glass cell; cell made of a synthetic material such as synthetic resin cell; and the surface of solid substances (object) such as glass rod, rod made of a synthetic material, rod having a thickened or thinned end, rod with an end having a round or flat projection and rod of strip shape.

An antibody, preferably the monoclonal antibody capable of specific reaction to the antigen produced in this invention, may be bound to this support. Binding of the antibody to the support may be achieved by a physical means such as adsorption, or by a chemical means using a condensing agent, or an activated substance, or by a means utilizing a mutual chemical bonding.

The labeling of the antibody may be achieved by using an enzyme, enzyme substrate, enzyme inhibitor, prosthetic group, coenzyme, enzyme precursor, apo-enzyme, fluorescent substance, coloring agent, magnetic substance, metal particles such as gold colloid particles and radioactive substance. The enzyme may include oxydation-reduction enzymes such as dehydrogenase, reductase and oxidase; transferases that catalyzes transfer of amino group, carboxyl group, methyl group, acyl group and phosphate group; hydrolases that hydrolyze ester bonding, glycoside bonding, ether bonding and peptide bonding; lyase; isomerase; ligase. The enzyme may be utilized in combination of plural enzymes for the purpose of detection. For example, an enzymatic cycling may be also utilized.

The representative radiolabel may include [$^{32}$P], [$^{125}$I], [$^{131}$I], [$^{3}$H], [$^{14}$C] and [$^{35}$S].

The representative labeling enzyme may include peroxidase such as horseradish peroxidase; galactosidase such as β-D-galactosidase from *E. coli*; maleate dehydrogenase; glucose-6-phosphate dehydrogenase; glucose oxidase; glucoamylase; acetylcholine esterase; catalase; alkaline phosphatase such as alkaline phosphatase from bovine intestine and alkaline phosphatase from *E. coli*.

If alkaline phosphatase is used, umbelliferon derivatives such as 4-methylumbeliferylphosphate; phenol phosphate derivatives such as nitrophenyl-phosphate; enzyme cycling system utilizing NADP; ruciferin derivatives; and dioxetan derivatives may be used as a substrate, and measurement can be achieved using luminescence or fluorescence derived from the reaction. The assay may be based on a luciferin-luciferase system. Catalase reacts with hydrogen peroxide to generate oxygen, and the generated oxygen can be detected using an electrode. The electrode used for the purpose may include a glass electrode, ion electrode using a hardly soluble salt membrane, liquid membrane-type electrode and polymer membrane electrode.

Enzyme labeling may be substituted for a biotin labeled compound and enzyme-labeled avidin (streptoavidin). The labeling may be based on plural different kinds of markers. In such a case, plural labeling may be achieved continuously or non-continuously, or simultaneously or separately at different times.

According to this invention, signals may be generated in combination of enzyme reagents such as horseradish peroxidase with 4-hydroxyphenyl acetate, 1,2-phenylenediamine or tetramethylbenzene; β-D-galactosidase or glucose-6-phosphate dehydrogenase with umbelliferylgalactoside or nitrophenylgalactoside. The assay system may include quinol compounds such as hydroquinone, hydroxypenzoquinone and hydroxyanthraquinone; or thiol compounds such as lipoic acid and glutathione, as these compounds can form phenol compounds or ferrocene compounds through enzymatic reaction.

The fluorescent or chemical luminescent compound may include fluorescein isothiocyanate; rhodamine derivative such as rhodamine B isothiocyanate and tetramethylrhodamine isothiocyanate; dansyl chloride; dansyl fluoride; fluorescamine; phycobiliprotein; acridinium salt; luminol such as lumiferin, luciferase and aequorin; imidazol; oxalic acid ester; chelating compounds based on a rare earth element; and coumarin derivatives.

The method of labeling may be achieved by reacting thiol group with maleimide group, pyridyldisulfide group with thiol group and amino group with aldehyde group, by a method conventionally known in this field, or a method easily performed by those skilled in the art, or a modified method of the above. Moreover, condensing agents utilized for production of said immunogenic complex, condensing agents utilized for binding with a support may be also employed.

The condensing agent may include, for example, formaldehyde; glutaraldehyde; hexamethylene diisocyanate; hexamethylene diisothiocyanate; N,N'-polymethylene bisiodoacetamide; N,N'-ethylene bismaleimide; ethyleneglycol bissuccinimidyl succinate; bisdiazobenzene; 1-ethyl-3-(3-dimethylaminopropyl) carbodiimide; succinimidyl 3-(2-pyridyldithio) propionate (SPDP); N-succinimidyl 4-(N-maleimidomethyl) cylcohexane-1-carboxylate (SMCC); N-sulfosuccinimidyl 4-(N-maleimidomethyl) cyclohexane-1-carboxylate; N-succinimidyl (4-iodoacetyl) aminobenzoate; N-succinimidyl 4-(1-maleimidophenyl) butylate; N-(ε-maleimidocaproyloxy) succinic acid imide (EMCS); iminothioran; anhydrous S-acetylmercapto succinate; methyl-3-(4'-dithiopyridyl) propionimidate; methyl-4-mercaptobutylylimidate; methyl-3-mercaptopropionimidate; and N-succinimidyl-S-acetylmercapto acetate.

According to the assay method of this invention, a labeled antibody reagent such as a monoclonal antibody in which the target substance to be determined is labeled with an enzyme, and an antibody conjugated with the support, may be reacted sequentially or simultaneously. The order for addition of the reagents may be altered according to the type of solid support chosen. For example, if beads of sensitized plastic are used, it may be transferred into a proper test tube together with the test sample containing the substance in which the amount of the labeled antibody reagent is to be measured (for example, enzyme-labeled monoclonal antibody). Then measurement can be performed by addition of beads such as sensitized plastic.

An immunological method may be utilized for the assay method of this invention, and a solid support used for the measurement may be a ball, microplate, stick, fine particle and test tube, made of polystyrene, polycarbonate, polypropylene and polyvinyl, which exhibit excellent adsorption of proteins such as antibodies, and various materials and shapes of solid support can be selected ad libitum.

The measurement may be performed in buffer system adjusted to maintain optimum pH such as pH4-9. The most preferred buffer includes, for example, acetate buffer, citrate buffer, phosphate buffer, tris buffer, triethanolamine buffer, borate buffer, glycine buffer, carbonate buffer and tris-hycrochloride buffer. Each of the buffers may be mixed at a desired ratio. Preferably, the antigen-antibody reaction may be allowed to occur at the temperature of 0-60° C.

Incubation treatment of an antibody reagent such as an enzyme-labeled monoclonal antibody, an antibody reagent stabilized to a solid support, and a test sample to be measured may be continued until the reaction reaches to its equilibrium. Alternatively the reaction may be stopped by separation of the solid phase and the liquid phase at determined period after the incubation treatment prior to it reaches to its equilibrium, and the existence of the labeled enzyme may be determined in the liquid phase or in the solid phase. The operation may be achieved using an automated assay system such as luminescence detector or photo-detector, and the measurement may be achieved by detecting an indicator signal obtained by conversion of the substrate via enzymatic reaction.

In the antigen-antibody reaction, the reagents, the substance to be measured, and the labeling of the enzymes may be stabilized, and some proper means can be made to facilitate stabilization of the antigen-antibody reaction itself. Furthermore, protein, stabilizer, surfactant, chelating agent may be added to the incubation solution as needed, so as to remove unspecific reactions, to decrease inhibitory effects or to increase the determining reaction. The preferred chelating agent may include ethylenediaminetetraacetic acid (EDTA).

The assay system may be subjected to a blocking treatment as well known to those skilled in the field, to prevent unspecific binding reactions. The treatment may be achieved by normal serum protein from a mammal, albumin, skim milk, milk fermentation product, collagen and gelatin. The substance to be added is not limited to any specific substance, as long as the substance can prevent unspecific binding reaction.

The test sample to be measured by the assay method may include solutions of various forms, colloid solutions and non-fluid samples, but it may preferably be a biological sample, such as thymus, testicle, intestine, kidney, brain, breast tumor, ovarian tumor, colonal/rectal tumor, blood, serum, synovial fluid, cerebrospinal fluid, pancreatic juice, bile, saliva, amniotic fluid, urine, other body fluids, cell culture medium, tissue culture medium, tissue homogenate, biopsy specimen, tissue and cell.

Various analysis/determination method including respective immunological assay method may be applied for the assay method according to this invention, and setting of any specific condition or operation is not required. Some ordinal technological consideration may be paid on the conventional condition or operation of the assay method, in order to construct the assay system related to the target substance according to this invention or a substance having substantially equal activity.

The details of the conventional techniques can be obtained in reference to reviews and monographs in the field, (for example, Hiroshi Irie (ed.), "Radioimmunoassay," Kodansha, (1974); Hiroshi Irie (ed.), "Further Details of Radioimmunoassay," Kodansha, (1979); Eiji Ishikawa (ed.), "Enzyme-Linked Immunoassay," Igaku-Shoin, (1978); Eiji Ishikawa et al. (ed.), "Enzyme-Linked Immunoassay," 2nd ed., Igaku-Shoin, (1982); Eiji Ishikawa et al. (ed.), "Enzyme-Linked Immunoassay," 3rd ed., Igaku-Shoin, (1987); H. V. Vunakis et al. (ed.), "Methods in Enzymology," Vol. 70 (Immunochemical Techniques, Part A), Academic Press, New York (1980); J. J. Langone et al. (ed.), "Methods in Enzymology," Vol. 73 (Immunolochemical Techniques, Part B), Academic Press, New York (1981); J. J. Langone et al. (ed.), "Methods in Enzymology," Vol. 74 (Immunochemical Techniques, Part C), Academic Press, New York (1981); J. J. Langone et al. (ed.), "Methods in Enzymology," Vol. 84 (Immunochemical Techniques, Part D: Selected Immunoassays), Academic Press, New York (1982); J. J. Langone et al. (ed.), "Methods in Enzymology," Vol. 92 (Immunochemical Techniques, Part E: Monoclonal Antibodies and General Immunoassay Methods), Academic Press, New York (1983); J. J. Langone et al. (ed.), "Methods in Enzymology," Vol. 121 (Immunochemical Techniques, Part I: Hybridoma Technology and Monoclonal Antibodies), Academic Press, New York (1986); J. J. Langone et al. (ed.), "Methods in Enzymology," Vol. 178 (Antibodies, Antigens, and Molecular Mimicry), Academic Press, New York (1989); M. Wilchek et al. (ed.), "Methods in Enzymology," Vol. 184 (Avidin-Biotin Technology), Academic Press, New York (1990); J. J. Lagone et al. (ed.), "Methods in Enzymology," Vol. 203 (Molecular Design and Modeling: Concepts and Applications, Part B: Antibodies and Antigens, Nucleic Acids, Polysaccharides, and Drugs), Academic Press, New York (1991), etc., and the description of those references is incorporated herein by way of citation).

Use of the soluble RAGE polypeptide according to this invention, preferably a monoclonal antibody, enables epitope mapping, and detection/determination of the soluble RAGE polypeptide or its related fragment can be achieved using an antibody recognizing the respective epitope.

An antibody specific to the soluble RAGE polypeptide or related peptide fragments will be useful for detection and/or determination of the suppressive or inhibitory effect of the interaction between the AGE and the transmembrane-type RAGE receptor by the soluble RAGE polypeptide; for detection and/or determination of various physiological substances, or physiological or biological phenomenon caused by the presence of excessive AGE; and for investigation and development of factors involved in regulation of production of the soluble RAGE polypeptide. The antibody according to this invention, particularly a monoclonal antibody, will be useful (i) for detection of disorders, abnormalities and/or diseases of tissues and cells caused by the interaction between AGE and RAGE; (ii) for detection of oncogenesis of cells, cell migration, invasion, mobility and/or metastasis caused by the interaction between AGE and RAGE or those symptoms; (iii) for detection of disorders, abnormalities and/or diseases related to glycation of proteins or those symptoms; (iv) for determination of expression of the soluble RAGE polypeptide; (v) for detection and/or determination of the alteration of AGE capturing activity; (vi) for investigation on compounds that regulates production of the soluble RAGE polypeptide; and/or (vii) for detection and/or determination of the activity of compounds that regulates production of the soluble RAGE polypeptide. Namely, such an antibody is expected to be useful to evaluate the extent of diabetic complications, abnormality of tissues, or migration, invasion, mobility and/or metastasis of a tumor.

According to this invention, suppressive or inhibitory activity of the soluble RAGE polypeptide on the interaction between AGE and transmembrane-type RAGE polypeptide can be detected and/or determined, and it can be used as a tool for monitoring the therapeutic effect of a therapeutic agent for diabetes; a therapeutic agent for prevention/treatment of diabetic complications; a therapeutic agent for prevention/treatment of disorders in tissues; anti-inflammatory agent; anti-tumor agent; cancer metastasis inhibitor; therapeutic agent for arteriosclerosis; therapeutic agent for Alzheimer disease; therapeutic agent for arthritis; anti-allergy agent and/or immunosuppressing agent.

The present invention also provides a method for detection and/or measurement of abnormalities in tissues, cells or proteins caused by AGE.

Active components according to this invention (for example, (a) the soluble RAGE polypeptide, and a partial peptide thereof or its salt, or the related peptides; (b) nucleic acids such as DNA coding for the soluble RAGE polypeptides; (c) antibodies according to this invention, and a fragments thereof (including monoclonal antibodies) or derivatives thereof; (d) compounds (or salts thereof) that suppress and/or inhibit biological activities such as suppression or inhibition interaction between AGE and transmembrane-type RAGE by the soluble RAGE polypeptide, or biological activities such as degeneration, overproduction or decomposition of tissues or proteins; or compounds (or salts thereof) that regulate production of the soluble RAGE polypeptide; (e) anti-sense oligonucleotides to the nucleic acid such as DNA according to this invention; (f) when an active substance detected according to this invention is used as a medicine, for example, an agent that inhibit the interaction between AGE and RAGE or its salt can be administrated as a pharmaceutical composition or a pharmaceutical preparation, alone or in combination with various pharmaceutically acceptable coadjuvant. Preferably, such an agent may have a dosage form suitable for oral administration, topical administration or non-oral administration, or may take any dosage form depending on the given purpose (including inhalation and rectal application).

The biologically active component according to this invention may be used in combination with a therapeutic agent for diabetic complications; therapeutic agent for arteriosclerosis; anti-hyperlipidemia agent; anti-cancer agent; cancer metastasis inhibitor; anti-thrombosis agent; therapeutic agent for Alzheimer disease; therapeutic agent for arthritis; anti-inflammatory agent; and/or immunosuppressing agent. Such agent can be used with no limitation, so far as it exerts some advantageous effect, for example, such agent can be selected from those known in this art.

The non-oral dosage form may include topical, percutaneous, intravenous, intramuscular, subcutaneous, or intraperitoneal administration. The agent may be applied directly to the affected lesion, in some occasion it is even preferred. Preferably, the agent may be administered to mammals including human, orally or non-orally (for example, intracellular administration, tissue administration, intravenous administration, subcutaneous administration, intradermal administration, intraperitoneal administration, intrathoracical administration, intrathecal administration, intravenous administration, instillation, rectal instillation, intra-aural instillation, perocular instillation, intranasal instillation, application via tooth, skin or mucosa). The dosage form of the concrete formulated preparation may include a liquid formulation, dispersed formulation, semi-solid formulation, granular formulation, molded formulation and leaching formulation. The dosage form may include, for example, tablets, coated tablets, sugar coated tablets, pills, troche, hard capsules, soft capsules, micro-capsules, implants, powder, grain, granules, particles, injectable solution, liquid preparation, elixir, emulsion, enema, syrup, watery preparation, emulsion, suspension, liniment, lotion, aerosol, spraying preparation, inhalant, nebularizer, ointment, balm, patch, pasta, pap, cream, oil, suppository (for example, rectal suppository), tincture, liquid formulation for cutaneous use, eye drop, nasal drop, ear drop, embrocation, transfusion, powder for preparation of injection solution, freeze-dried formulation and gel preparation.

Preparation of the medicinal composition may be achieved by a conventional method. For example, the medicinal composition may include a physiologically acceptable carrier, pharmaceutically acceptable carrier, adjuvant, excipient, shape retaining agent, diluent, flavoring agent, perfume, sweetener, vehicle, antiseptic, stabilizer, binder, pH adjuster, buffer, surfactant, base, solvent, filler, extender, dilution enhancer, solubilizer, tonicity adjuster, emulsifier, suspension enhancer, dispersant, thickener, gelatinizer, hardening agent, adsorbent, adhesive, elasticizer, plasticizer, disintegrating agent, jet injector, preserver, anti-oxidant, light shielding agent, moisturizer, moderator, anti-static agent and soothing agent, and these agents can be utilized alone or in combination. It is also possible to combine these agents with the protein according to this invention to formulate into a unit dosage form required for conventionally accepted pharmaceutical preparation.

The formulation suited for non-oral use may be a sterile solution or suspension comprising an active component and water or other pharmaceutically acceptable medium, such as water for injection. In general, preferred liquid medium for injection may include water, saline, dextrose solution, other related sugar solutions, ethanol, glycols such as propylene glycol and polyethylene glycol. Preparation of an injectable solution may be performed using a carrier such as distilled water, Ringer' s solution or saline, and a proper dispersant, moisturizer or suspension, according to conventional method known in this field, to prepare an injectable formulation such as solution, suspension and emulsion.

The aqueous solution for injectable solution may include, for example, saline, isotonic solution containing glucose or other coadjuvants (for example, D-sorbitol, D-mannitol and sodium chloride). The solution may be used in combination with a pharmacologically acceptable solubilizing agent such as alcohol (for example, ethanol), polyalcohol (for example, propylene glycol and polyethylene glycol), nonionic surfactant (for example, polysorbate 80™, HCO-50). The oily solution may include sesame oil and soybean oil. The solubilizing agent such as benzyl benzoate and benzyl alcohol may be used simultaneously. Moreover, the formulation may include a buffer (for example, phosphate buffer and sodium acetate buffer), a reagent for adjustment of osmotic pressure, soothing agent (for example, benzalkonium chloride and procaine hydrochloride), stabilizer (for example, human serum albumin and polyethylene glycol), preservative (for example, benzylalcohol and phenol), anti-oxidant (for example, ascorbic acid) and adsorption enhancer. Usually, the injection solution prepared may be filled in ampoules.

For the purpose of non-oral administration, the medicine may be formulated into the form of sterilized pharmaceutically acceptable solution or suspension of vehicles, such as water, ethanol and oil, with or without addition of a surfactant and other pharmaceutically acceptable auxiliary agent. The oily vehicle or solution to be used for formulation may include natural, synthetic or semi-synthetic mono-, di- or tri-glyceride; and natural, semi-synthetic or synthetic fats or fatty acids such as plant oils including peanut oil, corn oil, soybean oil and sesame oil. The solution for injection may be prepared to contain the compound according to this invention at a concentration of 0.1-10 wt. %.

The formulation suitable for topical administration such as for oral or rectal use may include, for example, gargling agent, tooth paste, oral nebulizer, inhalator, ointment, dental filler, dental coating agent, dental paste and suppository. Preparation of a gargling agent and other dental agents may be prepared according to the conventional method using a pharmacologically acceptable carrier. In the case of an oral nebulizer or an inhalator, such may be administrated for dental used as fine powders for inhalation, by dissolving the compound according to this invention alone or together with a pharmacologically acceptable inert carrier, into a solvent suitable for preparation of aerosol or nebulizer. Preparation of an ointment may be achieved by combining an ordinal base, for example an ointment base (for example, white vaseline, paraffin, olive oil, macrogoal 400 and macrogoal ointment) by a conventional method.

Medicines for topical application to teeth or skin may be formulated to a solution or a suspension comprising properly steriled water or non-aqueous excipient. The additive may include, for example, buffering agent such as sodium hydrogen-sulfite or disodium edetate; antiseptic including antibacterial or anti-fungal agent such as acetic acid and phenylmercury acetate, benzarconium chloride and chlorohexdin; and thickening agent such as hypromellulose.

Preparation of suppository may be achieved using a carrier well known in this field, preferably an appropriate non-irritant excipient, for example, polyethylene glycols, lanolin, cacao fat, fatty acid triglyceride, which takes solid form at an ordinal temperature, but melts into liquid at the temperature in the rectum to release the active medicine into the body, according to the conventional method, so as to contain the compound according to this invention at a concentration of 0.1-95 wt. % in general. The medicine may be suspended or dissolved into excipient, depending on the excipient used and concentration of the medicine. Adminiculas such as local anesthetics, preservative or buffer is generally soluble to an excipient.

The preparation suited for oral use may include, for example, solid form compositions such as tablets, pills, capsules, powder, granules and troche, and liquid form compositions such as liquid formulation, syrup and suspension formulation. Formulation may be achieved using a pharmaceutical coadjuvant known in the field. The tablets and pills may be further formulated to be an enteric-coated form. When the formulated dosage form unit is capsule, such type of material may further contain a liquid carrier such as fat.

Furthermore, when a nucleic acid such as the DNA according to this invention is used as a treatment and/or prevention agent, the nucleic acid can be used solely or it can be bound to an appropriate vector used in a technique of artificial gene recombination as described above, for example a vector derived from a virus such as retroviral vector. A nucleic acid such as the DNA according to this invention may be administrated by a conventional method. The nucleic acid may be administrated as it is or it can be formulated with an appropriate coadjuvant or with a physiologically acceptable carrier, for example to facilitate intracellular uptake, in the form of medicinal composition or medicinal preparation. Moreover, a method known as gene therapy may be also adopted.

The dose of the active component according to this invention to be administered may be selected from a wide variety. The dose and frequency of administration may be determined in consideration of sex, age, body weight, general physical condition, diet, time of administration, route of administration, speed of excretion, combination of administrated medicines, the severity of the disease to be treated, and other factors.

For production of the medicine, the additives or the method for preparation may selected and adopted as needed by referring, for example, to Japan Pharmacopoeia Editing Committee (ed.), "14th Revised Annotation of Japan Pharmacopoeia, Hirokawa, 2001; Hisashi Ichibangase et al. (ed.), "Development of Medicine," Vol. 12 (Material of Medicine [I]), Hirokawa, 1990, and "Development of Medicine," Vol. 12 (Material of Medicine [II]), Hirokawa, 1990.

The active component according to this invention is not specifically limited as long as having the biological activity to suppress or inhibit AGE activity, particularly the interaction between AGE and RAGE, preferably such component may have an advantageous effect. The active component according to this invention may include, for example, (a) the soluble RAGE polypeptide, variants polypeptide thereof, and a partial peptide thereof or a salt thereof; (b) nucleic acids such as DNA encoding the soluble RAGE polypeptide, or DNA encoding variants of the soluble RAGE polypeptide; (c) antibodies according to this invention, a fragment thereof (including monoclonal antibodies), and derivatives thereof; and (d) compounds (or salts thereof) that exhibit a biologically advantageous effect, such as the effect to suppress or inhibit the interaction between AGE and RAGE by the soluble RAGE polypeptide.

It is expected that the active component according to this invention may be useful for suppression or inhibition of the alteration in various tissues and cells caused by the interaction between AGE and RAGE. Moreover, the active component is useful to suppress the AGE actions, that is, the active component is useful for prevention or treatment of disorders, abnormalities and/or diseases caused by the interaction between AGE and RAGE. Moreover, the active component is expected to be effective for control or inhibition of migration, invasion, mobility and/or metastasis of tumor cells, caused by the interaction between AGE and RAGE.

The soluble RAGE polypeptide and the related peptides may be effective for blockade and/or inhibition of migration, invasion and/or metastasis of malignant tumor (i.e. cancer), and the soluble RAGE polypeptide may deserve as a prospective angiogenesis inhibitor, anti-tumor agent and/or anti-metastasis agent. The soluble RAGE polypeptide may be effective for prevention and inhibition of disorders, abnormalities and/or diseases of blood cells associated with AGE. In addition, it may be effective for a preventive medicine or a therapeutic medicine for diabetic complications, arteriosclerosis thrombosis and inflammation and/or an immuno-suppressing agent. Moreover, it may be effective as a therapeutic medicine for Alzheimer disease and arthritis.

According to this invention, an amino acid sequence may be selected from a group comprising: (a) an amino acid sequence comprising 1st to 347th amino acid residues out of the amino acid sequence of the soluble RAGE polypeptide; (b) an amino acid sequence comprising 1st to 117th amino acid residues out of the amino acid sequence of the soluble RAGE polypeptide; (c) an amino acid sequence comprising 332nd to 347th amino acid residues out of the amino acid sequence of the soluble RAGE polypeptide, then based on the structure of the selected sequence, a new molecular may be designed to obtain a substance having suppressive or inhibitory effect on the interaction between AGE and RAGE. Novel substances thus obtained are also included in the scope of this invention, and can be regarded as an active component according to this invention. A certain characteristic region may be selected from the sequence and following techniques known in this field may be adopted and performed, (i) substituting a group involved in pharmacologically activity in the sequence for an isosteres; (ii) substituting at least one amino acid residue constituting the sequence for a corresponding D-amino acid residue; (iii) modifying the side chain of the amino acid residue; (iv) arranging and binding an amino acid residue different from that existing in the sequence; and (v) analyzing the three-dimensional structure and designing a mimic structure (see, for example, Koichi Syudo (ed.), "Development of Medicine," Vol. 7, (Molecular designing), Hirokawa, (1990) and references cited therein). Part of the above technique includes above-mentioned matters.

The terms cited in this specification and figures are used in accordance with IUPAC-IUB Commission on Biochemical Nomenclature, or in the meanings conventionally utilized in this field.

The hybridoma:269-9C2, which was used for the production of the monoclonal antibody described below in Example 2(g) and specific to the soluble RAGE polypeptide, was deposited to National Institute of Advanced Industrial Science and Technology, International. Patent Organism Depository :IPOD (previous name: National Institute of Bioscience and Human-Technology), Higashi 1-1-1, Central 6, Tsukuba-shi, Ibaragi Prefecture (previous address: Higashi 1-1-3, Tsukuba-shi, Ibaragi Prefecture), postal code 305-8566 on Feb. 22, 2001, and maintained in the institute (deposition No. FERM P-18218).

EXAMPLE

Examples are presented as below and the present invention is described in detail, but this invention is not limited to those Examples, and it should be understood that various embodiments base in the concept of this invention are possible All the Examples were carried out using standard techniques, or could be possibly achieved by the standard techniques well known to skilled artisan, except for otherwise stated.

All the following Examples were carried out, except for otherwise stated, by the methods as described in the following references. DNA cloning was based on J. Sambrook, E.F. Fritsch & T. Maniatis, "Molecular Cloning," 2nd ed., Cold Spring Harbor Laboratory, Cold Spring Harbor, N.Y. (1989); and D.M. Glover et al. (ed.), "DNA Cloning," 2nd ed., Vols. 1-4, (The Practical Approach Series), IRL Press, Oxford University Press (1995). Particularly, PCR was achieved by the method as described in H.A. Erlich (ed.), "PCR Technology," Stockton Press, (1989); D.M. Glover et al. (ed.), "DNA Cloning," 2nd ed., Vol. 1 (The Practical Approach Series), IRL Press, Oxford University Press (1995); and M.A. Innis et al. (ed.), "PCR Protocols," Academic Press, New York (1990). When commercially available reagents and kits were used, the protocols and chemicals attached thereto were used.

The reagents were mainly purchased from Wako Pure Chemicals, except for the following: Tween 20 (Bio-Rad); skim milk (Morinaga Dairy Products); Trizma base (Sigma); and ethanolamine (Sigma).

Example 1

[Cell]

The primary cultures of microvascular endothelial cells from human skin were obtained from Cascade Biologics, Inc. (Portland, Oreg.). The cells having undergone 5-10 passages were used for purification of poly(A)+RNA.

[Isolation of Polysome-Derived Poly(A)+RNA]

The microvascular endothelial cells from human skin were grown in a flask for tissue culture, and washed with ice-cooled phosphate buffer/saline. Then, the cells were scrapped off with a cell scraper. The cell suspension was centrifuged, and the cells were collected as pellet. The cell pellet was suspended in 10 mM Tris-HCl buffer (pH7.6) containing 0.25M KCl, 10 mM $MgCl_2$, 1 mM EDTA, 0.25M sucrose (RNase free), 0.1 mM DTT, 2 mM 4-(2-aminoethyl)-benzenesulfonylfluoride, and 1000 u/ml RNase inhibitor (Ambion, Inc., Austin, Tex.). The cells were then disrupted with a Dounce type homogenizer. The cell-lysate was centrifuged at 12,000×g for 15 minutes to remove nuclei and mitochondria, and the supernatant was collected. The obtained supernatant was centrifuged at 100,000×g for 60 minutes, and a polysome fraction was collected as precipitate. Isolation of poly(A)+ RNA from the obtained polysome fraction was achieved using a Quickprep micro mRNA isolation kit (Amersham Pharmacia Biotech).

Figure 1:
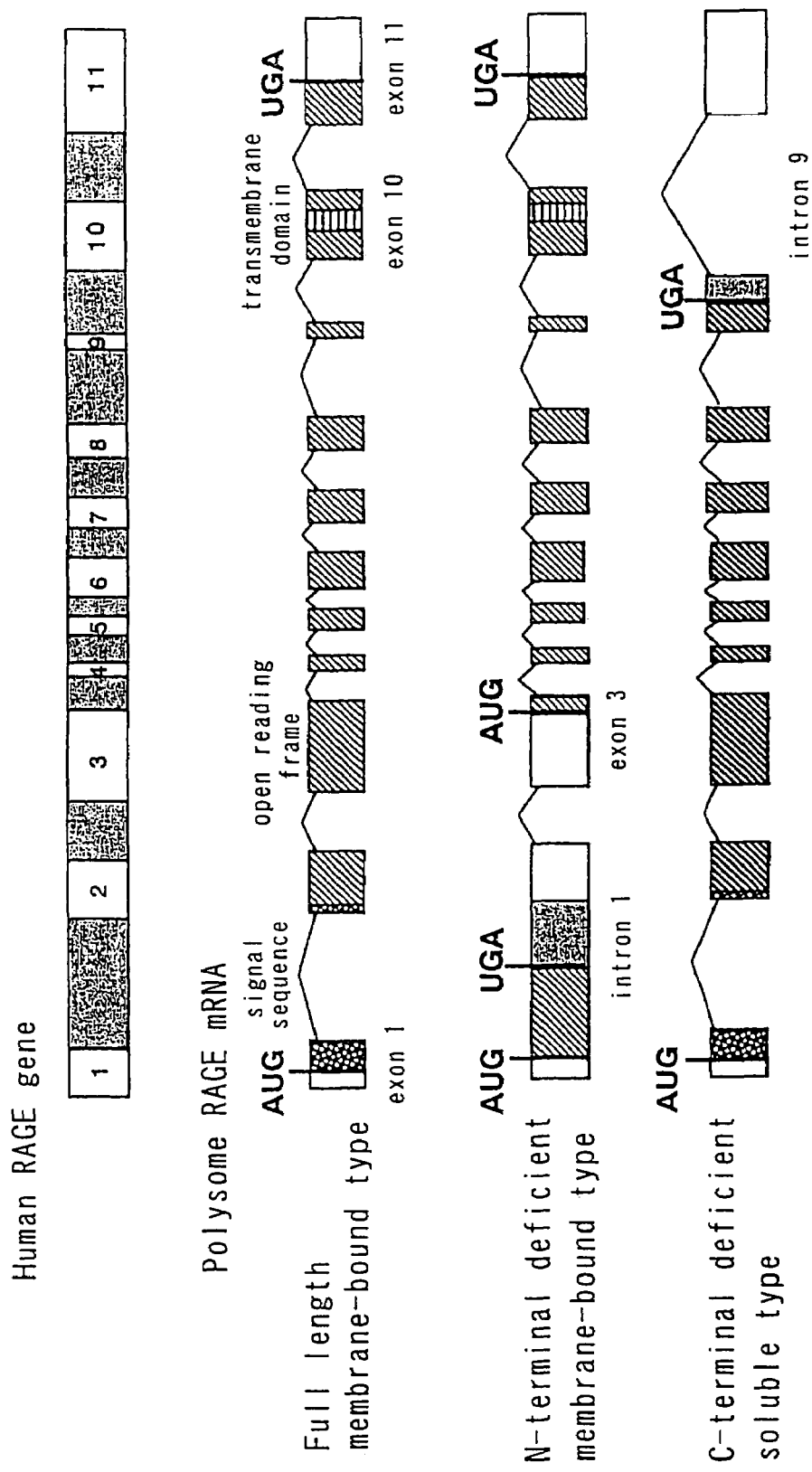
FIG. 1 represents the structure of a human gene and molecular diversity of the RAGE polypeptide produced by alternative splicing of the RAGE gene transcripts. The C terminal deficient type corresponds to the soluble RAGE according to this invention.

[Isolation of cDNA for a Soluble RAGE Polypeptide]

cDNA was synthesized by using poly(A)+RNA obtained from the polysomes of microvascular endothelial cells from human skin as a template an oligo(dT) primer and AMV-derived reverse transcriptase. The cDNA for a RAGE polypeptide was amplified using Primers (5'-GCCAGGAC-CCTGGAAGGAAGCA-3', sequence ID No. 3 in the sequence list; 5'-CTGATGGATGGGATCTGTCTGTG-3', sequence ID No.4 in the sequence list) corresponding to exons 1 and 11 (see FIG. 1) of a gene coding for a RAGE polypeptide and Takara LA Taq polymerase. The amplified RAGE cDNA was inserted into a pCR2.1 (Invitrogen) to transform E. coli XL1-Blue. The plasmid DNA was purified from 32 clones obtained recombinant E. coli colonies, and sequenced with a ABI377 sequencer (Aplid Biosystems, Inc.). Thus, cDNA coding for a soluble RAGE polypeptide was obtained.

The base sequence of the determined cDNA for a soluble RAGE polypeptide and the amino acid sequence coded by an open reading frame within the above sequence are listed in the sequence ID No. 1 in the sequence listing. The sequence ID No. 2 in the sequence listing shows the amino acid sequence of a soluble RAGE polypeptide.

FIGS. 2-4 shows the base sequences of the nucleic acids coding for a soluble RAGE polypeptide (soluble RAGE) of this invention in comparison with the transmembrane RAGE (full RAGE) polypeptide, from which artificially prepared recombinant soluble RAGE polypeptide (designated U.S. Pat. No. 5,864,018) was derived, using the RAGE cDNA having the transmembrane domain. FIG. 5 shows the amino acid sequences of soluble RAGE polypeptide of this invention, in comparison with the full RAGE polypeptide and the U.S. Pat. No. 5,864,018 polypeptide. The soluble RAGE polypeptide (soluble RAGE) of this invention is a native, endogenous polypeptide, and is different from the full RAGE polypeptide in the C-terminal 16 amino acid residues ($Glu^{332}$-$Met^{347}$ of the sequence ID No. 2).

[Preparation of Expression Vector for a Soluble RAGE Polypeptide]

The amplification was achieved by using cDNA coding for the soluble RAGE polypeptide as a template, the 5'-primer (5'-GAGAATTCGCCAGGACCCTGGAAGGAAGCA-3', sequence ID No. 5) having an EcoRI recognition site and the 3'-primer (5'-GATCTAGAGATTGTTGACCATC-CCCCCAG-3', sequence ID No. 6) having an Xba-I recognition site. The amplified DNA was purified and then digested with EcoRI and XbaI. The resulting DNA fragment was inserted into the EcoRI and XbaI sites of pCI-neo vector (Stratagene), which is an expression vector for animal cells. The expression vector DNA was purified using a plasmid purifying kit (Qiagen, Valencia, Calif.), and the sequence of the expressing vector DNA was confirmed by using ABI377 sequencer (Applied Biosystems, Inc.).

[Introduction of an Expression Vector for Soluble RAGE Polypeptide into a COS7 Cell and Isolation of Stable Transformants]

The expression vector for the soluble RAGE polypeptide was introduced into COS7 cell using Tfx-20 reagent (Promega Co., Madison, Wis.). Forty-eight hours after introduction of the expression vector, G418 (Geneticin) was added to the cell culture, and two weeks later several G418 resistant colonies were obtained. The obtained clones were separately grown, and cell extracts and culture media were analyzed with western blotting using the anti-human RAGE polypeptide antibody. Based on the result, a clone over-expressing the soluble RAGE polypeptide was selected.

[Cultivation of Transformant]

The COS7 cells over-expressing the soluble RAGE polypeptide were grown at 37° C. in the presence of 5% $CO_2$ on a Dulbecco-modified Eagle medium containing 5% fetal calf serum and 500 µg/ml G418 with a cell culture dish having a diameter of 150 mm until the cells became confluent. Then, the cell layer was washed twice with PBS ($Ca^{2+}$/$Mg^{2+}$-free), to remove the medium completely. Then, the cells were cultured for 48 hours on a serum-free, Dulbecco-modified Eagle medium. After it, the culture medium was recovered and centrifuged at 10,000 rpm for 20 minutes, and the supernatant was filtered with 0.22 µm membrane filter. The soluble RAGE polypeptide was purified from the obtained culture medium according to the following method.

[Purification of the Soluble RAGE Protein]

Four L of the obtained culture medium was applied at a flow rate of 3 ml/min to HiTrap Heparin column (column volume 3×5 ml, Amersham Pharmacia) equilibrated with 20 mM Tris-HCl (pH7.4), and then 75 ml of 20 mM Tris-HCl (pH7.4) containing 0.15M NaCl was allowed to flow at a rate of 2 ml/min to wash the column. Then, 75 ml each of 20 mM Tris-HCl, pH7.4 containing 0.3M, 0.5M and 1M NaCl were applied in a stepwise manner to the column, to sequentially eluate column-bound substances at a rate of 2 ml/min. Fractions each having 5 ml volume were collected. Fractions containing the eluted soluble RAGE protein were identified via western blotting.

Then, a fraction of the soluble RAGE polypeptide, diluted to five fold with 50 mM sodium acetate buffer (pH4.5), was applied to 1 ml RESOURCE S column (Amersham Pharmacia) equilibrated with 50 mM sodium acetate buffer (pH4.5) at a flow rate of 1 ml/min. Then, 3 ml of 50 mM sodium acetate buffer containing 0.2M NaCl was allowed to flow at a rate of 1 ml/min to wash the column. Next, 5 ml of 50 mM sodium acetate buffer was allowed to flow at a rate of 1 ml/min. so that a linear gradient of NaCl concentration ranging from 0.2 to 1.0M was prepared, cationic substances bound to the column to sequentially elute, and the eluate was collected in fractions having a volume of 0.5 ml. Fractions containing the soluble RAGE protein were identified via western blotting. Each 2 ml of the obtained soluble RAGE fraction was applied to a HiTrap Desalting column (column volume 2×5 ml, Amersham Pharmacia) equilibrated with PBS ($Ca^{2+}$/$Mg^{2+}$-free). Gel filtration was achieved in PBS ($Ca^{2+}$/$Mg^{2+}$-free) at a flow rate of 0.5 m/min. High molecular weight fractions were recovered. Then the fractions were subjected to ultrafiltration using Centricon YM-3 (Millipore) to prepare concentrated solution of the soluble RAGE polypeptide (sRAGE), if necessary.

Figure 6:
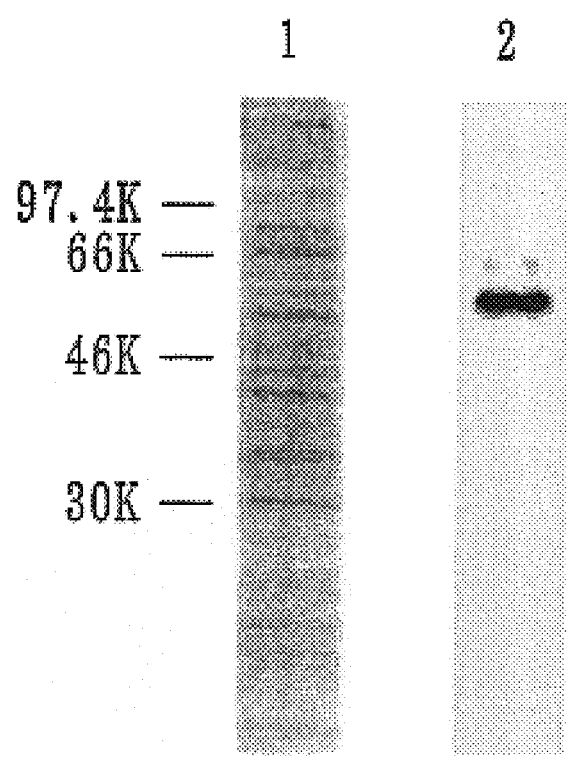
FIG. 6 is a photograph of electrophoresis after separation of sRAGE protein by 10% SDS-PAGE: 1 represents a silver stain image of supernatant sample obtained from cell culture; and 2 represents a silver stain image of purified protein.

The purity of the purified sRAGE polypeptide was evaluated by separating about 100 ng protein of sRAGE using 10% SDS-PAGE, and staining protein bands by the silver stain method. The result is shown in FIG. 6. In FIG. 6, 1 represents the picture of the cell culture supernatant, obtained by silver-staining, while 2 represents the picture of the purified protein, obtained by silver-staining.

The chromatography as described above was achieved by using an AKTA system (Amersham Pharmacia), and measuring the absorbance of eluate at 230, 280 and 300 nm, and monitoring it.

[Test for Evaluating the Binding of AGE with Soluble RAGE Polypeptide]

The binding of AGE to soluble RAGE polypeptide was checked by surface plasmon resonance using BIACORE system (Biacore, Sweden). The purified soluble RAGE polypeptide was fixed onto a sensor chip CM5 (Biacore) via amino coupling. The AGE-BSA prepared by incubating glucose and bovine serum albumin (BSA) at 37° C. for 12 weeks under a sterile condition, was added to microfludic flow system of Biacore system as an analyte at a concentration of 500 μg/ml. It was found, consequently, that the AGE-BSA did not show any response to the inline reference (control chip) nor to a tip fixed with immunoglobulin, but showed specific binding with only the sensor chip fixed with the soluble RAGE polypeptide.

Example 2

Preparation of Monoclonal Antibody (a) Immunizing Source

As an antigen to be used for immunization, a synthetic polypeptide designed on the basis of the amino acid sequences, such as the recombinant soluble RAGE polypeptide and the sequence ID No. 2 of the sequence listing can be used. Moreover, the obtained cDNA is ligated to an expression vector for animal cell for expression in CHO cell, and thus obtained recombinant sRAGE can also be used as an antigen. The antigen protein may be purified by ion exchange chromatography, gel filtration, or other various chromatography.

It is possible to use the purified antigen for immunization by a conventional method to establish immunization, antibody-producing cells can be induced, then antibody-producing cells can be obtained as hybridomas by cell fusion. Further, hybridoma can be cloned based on the reactivity toward the purified antigen for immunization, and it can be established as a cell line of monoclonal antibody-producing hybridoma.

As the antigen used to obtain a monoclonal antibody specific to the soluble RAGE polypeptide, a hapten-modified synthetic polypeptide having an amino acid sequence characteristic to the soluble RAGE polypeptide may be used.

For example, the preferred polypeptide may have, at its C terminal, a serial amino acid sequence comprising at least three or more, and preferably five or more amino acid residues, selected from the sequence of; Glu-Gly-Phe-Asp-Lys-Val-Arg-Glu-Ala-Glu-Asp-Ser-Pro-Gln-His-Met. Specifically, a polypeptide having a sequence of Cys-Glu-Gly-Phe-Asp-Lys-Val-Arg-Glu-Ala-Glu-Asp-Ser-Pro-Gln-His-Met (CEGFDKVREAEDSPQHM) is preferred as an antigen.

(b) Preparation of Antigen Polypeptide

A characteristic sequence was selected from the amino acid sequence of a human soluble RAGE polypeptide described in the sequence ID No. 2 of the sequence listing, and a polypeptide having the sequence was synthesized. Synthesis of the peptide may be achieved by Fmoc-bop method using peptide synthesizer (peptide synthesizer 9600, MilliGen/Biosearch). Cysteine was attached to the N terminal of the synthetic polypeptide. The synthetic polypeptide was purified by the methods, such as high performance liquid chromatography using a μ Bondasphere, C18 column (Waters). A synthetic polypeptide comprising Cys-Glu-Gly-Phe-Asp-Lys-Val-Arg-Glu-Ala-Glu-Asp-Ser-Pro-Gln-His-Met (sequence ID No. 7) was synthesized, and was used as an antigen in the following experiment.

(c) Preparation of Polypeptide-BSA Conjugate

The polypeptide was bound via the cysteine residue to bovine serum albumin (BSA) to produce an antigen conjugate. A solution obtained by dissolving 10.1 mg of BSA in 1 mL of 0.1M phosphate buffer, pH7.0 and another solution obtained by dissolving 1.14 mg of EMCS (N-(amaleimide-caproyloxy)-succinimide) in 24.9 μL of dimethylformamide were mixed, and the mixture was incubated at 30° C. for 30 minutes. Gel filtration chromatography of the mixture was then achieved by a gel column (13 mm in diameter, and 120 mm in length) of Sephadex G-25 (Pharmacia) equilibrated with 0.1M phosphate buffer, pH7.0. The polypeptide synthesized in above step (b) was dissolved in 0.1M phosphate buffer pH7.0, and the solution was mixed with the maleimide-bound BSA solution such that the molar ratio of polypeptide to maleimide-bound BSA became 50:1. Namely, the maleimide-bond BSA was mixed in the polypeptide, and the mixture was incubated at 4° C. for 20 hours to prepare a BSA-polypeptide conjugate.

The obtained BSA-polypeptide conjugate was diluted with 0.1M phosphate buffer, pH7.0 and 150 μL aliquots were then sampled and stored frozen at −30° C.

(d) Preparation of Antibody Producing Cells

The BSA-polypeptide conjugate prepared in above step (c) was injected intraperitoneally into a 6 week old female Balb/c mouse together complete with Freund's adjuvant to perform first immunization. About 18 days later, the BSA-polypeptide conjugate dissolved in 0.1M phosphate buffer, pH7.5 was injected intraperitoneally into the first immunized to prepare additional immunization. Further, fifty-two days later, the BSA-polypeptide conjugate dissolved in 0.1M phosphate buffer, pH7.5 was injected intravenously into the additionally mouse to perform final immunization. Four days later, the spleen was removed, and spleen cell suspension was prepared.

(e) Cell Fusion

Cell fusion was achieved using the following materials and method. RPMI-1640 medium: sodium hydrogencarbonate (24 mM), sodium pyruvate (1 mM), penicillin G potassium (50 U/ml), and amikacin sulfate (100 μg/ml) were added to an RPMI-1640 medium (flow lab.), and its pH was adjusted to pH7.2 with dry ice. The medium was filtered with a 0.2 μm Toyo membrane filter for sterilization. NS-1 medium: FCS (M.A. Bioproducts) was filtered for sterilization, and was added to the above RPMI-1640 medium to 15% (v/v). PEG-4000 solution: the serum-free medium, to which polyethylene glycol 4000 (PEG-4000, Merk & Co.) was added to an RPMI-1640 medium to 50% (w/w), was prepared.

Fusion with azaguanine-resistant myeloma cells SP2 (SP2/0-Ag14) was achieved by a method obtained by slightly modifying the method described by Oi et al. in: "Selected Method in Culture Immunology," pp. 351-372 (ed. B. B. Mishell and S. N. Shiigi), W. H. Freeman & Co., (1980).

The nucleated spleen cells (100% viability) prepared in the above step (d) and myeloma cells (100 viability) were fused together at a ratio of 5:1 to 10:1 according to the following procedure. A suspension containing the polypeptide-immunized spleen cells and myeloma cells, respectively, were washed with RPMI1640 medium. Then, they were separately suspended in the same medium, and the nucleated spleen cells and the myeloma cells were mixed for fusion. About $8.0 \times 10^7$ myeloma cells were combined with about $4.0 \times 10^8$ nucleated spleen cells.

Then, the solution mixed each cell was centrifuged to precipitate a cell. The supernatant was completely removed by aspiration. RPMI-1640 medium containing 50% PEG-400, which had been warmed to 37° C. (the volume of the medium was determined so as to finally give a myeloma cells population of about $3 \times 10^7$ cells/mL) was added dropwise to precipitated cells. The medium was stirred to allow cells to be resuspended and dispersed. Then, RPMI-1640 medium having two-fold volume of the added RPMI-1640 medium suspension containing 50% PEG-4000 and warmed to 37° C., was added dropwise. Still further, RPMI-1640 medium having a seven-fold volume of the added RPMI-1640 medium containing 50% PEG-4000, was added dropwise, while the medium being always stirred, to disperse cells evenly in the medium. The cell suspension was centrifuged, and the supernatant was completely removed via aspiration. Next, NS-1 medium which had been warmed to 37° C. was rapidly added to the precipitated cells to make the final concentration of myeloma cells be $3 \times 10^6$ cells/mL. Large cell clusters, were carefully dispersed via pipetting. The same medium was added to further dilute the cells, and the cell suspension was inoculated to a 96-well microwell plate made from polystyrene to make the number of the myeloma cells per well to be about $6.0 \times 10^5$. Each plate, to which the cells added, transferred into an incubator kept at 37° C. and filled with 7% carbon dioxide/93% air, and incubated in the carbon dioxide/93% air at 37° C. under 100% humidity.

(f) Selective Growth of Hybridoma on Selective Medium
  (1) The used media are as follows.
  HAT medium: this was obtained by further adding hypoxanthine (100 μM), aminopterin (0.4 μM) and thymidine (16 μM) to NS-1 medium mentioned in above step (e).
  HT medium: this was the same as HAT medium described above except that aminopterin was removed from it.
  (2) Next day (Day 1) after the start of incubation mentioned in above step (e), two drops (about 0.1 ml) of HAT medium were added to the cells by Pasture pipette culture (culture plate). At Day 2, 3, 5 and 8, half of the medium about 0.1 ml was replaced with the same volume of fresh HAT medium, of Day 10, half of the medium was replaced with the same volume of fresh HT medium. Enzyme-linked immunosorbent assay (ELISA) was performed on all the wells, wherein the growth of the hybridoma was found by the naked eye, to check the positive well. Firstly, the antigen polypeptide diluted with 20 mM carbonate buffer (pH9.6) was coated onto a polystylene 96 well plate (100 ng/well). Then, the plate was washed with PBS containing 0.05% Tween, to wash out unbound peptide. A 0.1 ml of culture supernatant of the well, wherein the growth of the hybridoma was found, was added to each well, and the plate was still standing at room temperature for one hour. After washing, horseradish peroxidase (HRP)-labeled goat anti-mouse immunoglobulin (Cappel) serving as a secondary antibody was added to each well. The plate was further incubated at room temperature for another one hour. After washing, hydrogenperoxide and 3,3',5, 5'-tetramethylbenzidine (TMB) serving as a substrate were added to each well for color development. A 2N sulfuric acid was added to each well to arrest the coloring reaction, and the extent of the coloring on the each well was determined as the absorbance at 450 nm using a spectrometer for microplate (MRP-A4, Toso).

(g) Cloning of Hybridoma

Cloning of hybridomas, which had been found to positively react with the antibody peptide in step (f), were achieved by limiting dilution. A cloning medium containing about $10^7$ cells of mouse thymocytes per NS-1 medium 1 ml as a feeder, was prepared the hybrydomas were diluted to be five hybridomes, one and 0.5 hybridoma per well, and these three kinds of the dilutions were added to 36 wells, 34 wells and 24 wells, respectively, in a 96-well microwell plate. On Days 5 and 12, additional about 0.1 ml of NS-1 medium was added to all the wells. ELISA was performed on the wells exhibiting sufficient growth of the hybridomas, and on the group having 50% or more of the colonization-negative wells. When all the checked wells were not found positive, four to six wells have one colony were selected from the antibody-positive wells and re-cloning of them was performed. Ultimately, hybridomas that could produce monoclonal antibody to each polypeptide could be obtained. From them four different monoclonal antibodies were obtained.

(h) Determination of Class and Subclass of Monoclonal Antibody

According to ELISA as described above, the supernatant of the hybridomas obtained in above step (g) was added to a 96-well plate made from polystyrene coated with each polypeptide. After washing with PBS, horseradish peroxydase-labeled goat anti-rabbit IgG (H+L) was added to each well; and hydrogen peroxide and 2,2'-azino-di(3-ethylbenzothiazolinic acid) serving as a substrate was used, to determine the class and subclass of the monoclonal antibody.

TABLE 1

Anti-human soluble RAGE C-terminal polypeptide monoclonal antibody

| Clone No. | Subclass |
|---|---|
| 269-1D10 | γ1/κ |
| 269-4C9 | μ/κ |
| 269-6B12 | μ/κ |
| 269-9C2 | γ1/κ |

(i) Cultivation of Hybridoma and Purification of Monoclonal Antibody

The obtained hybridoma cells were grown on NS-1 medium. Then, it was possible to obtain a monoclonal antibody from the supernatant. Moreover, about $10^7$ obtained hybridomas were injected intraperitoneally into a mouse (Balb/c strain, female 6 week old) which had previously received the intraperitoneal injection of pristane one week before, then one to two weeks later, abdominal dropsy containing the monoclonal antibody at a concentration of 4-7 mg/ml can be obtained from the abdominal dropsy. The obtained abdominal dropsy was salted out by 40% saturated ammonium sulfate. Then the IgG class antibody was absorbed to protein A Affi-Gel (Bio-Rad); and it was purified by eluting with 0.1M citiric acid buffer, pH5.0.

Example 3

Western Blotting

A 9 μl of supernatant of the culture of COS7 cells expressing the human soluble RAGE polypeptide, 750 ng of the extract of COS cells expressing human recombinant matured full-length RAGE polypeptide (membrane-type RAGE polypeptide), and 150 ng of human lung extract protein were separated with 10% SDS-PAGE under reductive condition, and then transferred to a polyvinylidene difluoride (PVDF) membrane (MILLIPORE). Then, blocking of the membrane was performed with PBS containing 1% BSA, 5% skim milk and 0.1% Tween20 (blocking buffer) at room temperature for one hour, and then they were incubated at 25° C. for one hour in the culture supernatant of the hybridoma cell lines 269-1D10, 269-4C9, 269-6B12 or 269-9C2, which expressed an antibody specific to anti-human soluble RAGE. The respective membrane was washed four times with PBS containing 0.1% Tween 20 (0.1% PBS-T). The bound antibodies were allowed to react at 25° C. for one hour with HRP-bound sheep anti-mouse immunoglobulin antibody (Amersham Pharmacia) diluted with the blocking buffer at a ratio of 1:1,000. After the reaction, each membrane was washed four times with 0.1% PBS-T, and bound antibodies were detected by Enhanced chemiluminescence (ECL, Amersham Pharmacia). As the positive control, 3 μl of the supernatant of the culture of COS7 cells expressing the human soluble RAGE polypeptide, 250 ng of the extract of COS cells expressing human recombinant matured full-length RAGE polypeptide, and 50 ng of human lung extract protein were used respectively. They were treated with rabbit anti-human RAGE antisera diluted with the blocking buffer to 1:500 and with HRP-bound goat anti-rabbit IgG (H+L) antibody, (Zymed) diluted with the blocking buffer to 1:2,000 in the same manner as above, and binding reaction was detected using ECL. The result is shown in FIG. 7.

M: molecular weight marker 1, 4, 7, 10, 16: recombinant membrane type RAGE 2, 5, 8, 11, 17: recombinant soluble RAGE 3, 6, 9, 12, 18: human lung extract (rich in membrane penetrating RAGE)

Result

Each monoclonal antibody did not cross-react with the recombinant transmembrane RAGE polypeptide, and with the transmembrane RAGE polypeptide in human lung extract, but reacted with the soluble RAGE polypeptide.

Example 4

Assay of Human Soluble RAGE Polypeptide Monoclonal Antibody Western Blotting

Figure 8:
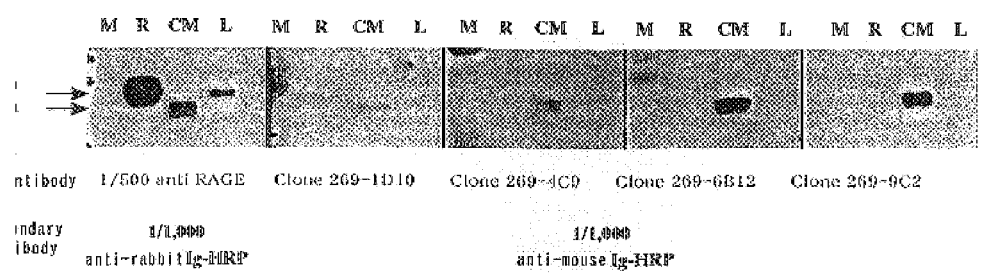
FIG. 8 is a photograph of the electrophoresis of the western blotting for verification of hybridoma clones.

A cell extract from GEN-T cells over-expressing the matured human RAGE polypeptide (corresponding to 750 ng protein); 3 μl of supernatant from the culture of COS7 cells over-expressing the human soluble RAGE polypeptide; human lung extract (equal to 150 ng protein); and Rainbow Marker (myosin, phosphorylase b, bovine serum albumin, ovalbumin, carbonic anhydrase, trypsin inhibitor, lysozyme, each 3 μg) (Amersham Pharmacia) were separated by 10% SDS-PAGE under a reducing condition, and were then transferred to Immobilon transfer membrane (MILLIPORE). The membrane was gently shaken at room temperature for one hour in a solution comprising PBS/0.1% Tween20/5% skim milk. Then, the membranes were reacted in the culture supernatants clone No. 269-1D10, 269-4C9, 269-6B12, and 269-9C2 at room temperature for one hour. After incubation, each membrane was washed four times with 0.1% Tween20/PBS solution for 15 minutes. Then, each membrane was incubated with horseradish peroxidase linked anti mouse Ig antibody (from sheep) (Amersham Pharmacia) diluted 1000-fold with PBS/0.1% Tween20/5% skim milk solution at room temperature for one hour, and each membrane was washed four times with PBS/0.1% Tween20 solution for 15 minutes. After it, each membrane was treated with an ECL Western Blotting Detection System (Amersham Pharmacia), and the signal was detected on an X-ray film. The result is shown in FIG. 8. In FIG. 8, M represents molecular weight markers (3 μg for each molecular marker); R, matured human RAGE polypeptide with His tag; CM, COS7 cell over-expressing human soluble RAGE polypeptide; and L, human lung extract. Any monoclonal antibodies tested did not react with the matured human RAGE polypeptide nor with the human lung extract, but reacted only with the human soluble RAGE polypeptide.

Example 5

Immunoprecipitation

A 1 ml of Protein G Sepharose (Amersham Pharmacia) was centrifuged at 200×g for one minute. After the supernatant was removed, TSA was added to the resin. The resin was washed three times using the same operation. Then, 600 μl of the culture supernatant of cos7 cell over-expressing the human soluble RAGE polypeptide, centrifuged at 10,000 rpm for 20 minutes, was added to the resin. The resultant suspension was gently stirred at room temperature for two hours, centrifuged at 200×g for one minute, and the supernatant was used for the following. A 50 μg of human soluble RAGE polypeptide monoclonal antibody 269-1D10, 269-9C2, or normal mouse immunoglobulin, respectively, dissolved in each 100 μL of PBS were added to 50 μl of resin previously washed with TSA in the same manner as above, and each resultant suspension was left at 4° C. for two hours while being stirred occasionally. Then, each resultant suspension was centrifuged at 200×g for one minute, the supernatant was removed, and 150 μl of the above culture supernatant was then added to each precipitate, each resultant suspension was left at 4° C. for two hours while being stirred occasionally. After it, each resultant suspension was centrifuged at 200×g for one minute, the supernatant was removed, and then, 500 μl of TSA was added, and the resin was washed three times using the same operation. Finally, 500 μl of Tris-HCl, pH6.8 was added to wash the resin, and then each resultant suspension was centrifuged at 200×g for one minute, and the supernatant was removed. 50 μl of SDS-PAGE sample buffer (0.05M Tris-HCl, pH6.8/2% SDS/0.6% 2-mercaptoethanol/10% glycerol/0.005% bromophenol blue/) was added to each resin, and each resultant suspension was heated at 100° C. for three minutes, centrifuged at 200×g for one minute, and 20 μl of each supernatant was separated by 10% SDS-PAGE. After separation, the separated proteins were transferred to Immobilon transfer membrane (MILLIPORE), and the membrane was gently shaken in PBS/0.1% Tween20/5% skim milk solution at room temperature for one hour. Next, the membrane was incubated in a solution comprising rabbit anti-human soluble RAGE polypeptide polyclonal antibody at 5 µg/ml and PBS/0.1% Tween20/5% skim milk at room temperature for one hour. Then, the membrane was washed with four times for 15 minutes with 0.1% Tween20/PBS solution. Then, the membrane was incubated with horseradish peroxidase linked anti-mouse Ig antibody (from sheep)(Amersham Pharmacia) diluted 1000-fold with PBS/0.1% Tween20/5% skim milk solution, at room temperature for one hour, and was washed four times with PBS/0.1% Tween20 solution for 15 minutes. Then, the membrane was treated with an ECL Western Blotting Detection System (Amersham Pharmacia). The signal was detected on an X-ray film. The result is shown in FIG. 9. In FIG. 9, 1 represents monoclonal antibody 269-1D10, 2 represents monoclonal antibody 269-9C2, and 3 represents normal mouse immunoglobulin. An affinity column to which the anti-soluble RAGE polypeptide monoclonal antibody was bound, trapped human soluble RAGE polypeptide. Another affinity column, to which normal mouse immunoglobulin used as the control was bound, could not trap human soluble RAGE polypeptide.

Example 6

Preparation of Human Soluble RAGE Antibody Immunoaffinity Column

The solvent of human soluble RAGE monoclonal antibody 269-1D10 was exchanged for coupling buffer (0.2M NaHCO$_3$, 0.5M NaCl, pH8.3) via a disposable PD-10 column (Amersharm Pharmacia). A 1 ml of the above solution containing the human soluble RAGE polypeptide monoclonal antibody was applied on a HiTrap NHS-activated column (1 ml)(Amersham Pharmacia), which was previously washed with 6 ml of ice-cooled 1 mM hydrochloric acid, and the column was incubated at room temperature for 30 minutes. Then, 3 ml of coupling buffer was applied on into the column. One ml of 2M Glysine-HCl, pH2.0 was added to the eluate and A280 was measured to calculate coupling efficiency. The column was washed with 6 ml of buffer A (0.5M ethanolamine, 0.5M NaCl, pH8.3), and 6 ml of buffer B (0.1M acetate, 0.5M NaCl, pH4.0) sequentially, and then 6 ml of buffer A was injected into the column, and the column was left at room temperature for 30 minutes. The column was again washed with 6 ml of buffer B and 6 ml of buffer A sequentially in this order, and finally with 6 ml of buffer A. After a preserving solution (0.05M Na$_2$HPO$_4$, 0.1% NaN$_3$, pH7.0) was injected into the column, the column was kept at 4° C. All the above operations were carried out at a flow rate of 200 µl/min.

Example 7

Isolation of Soluble RAGE Polypeptide from Human Serum

The immunoaffinity column for the soluble RAGE polypeptide prepared as above method was installed in.S-MART System; and the column was washed sequentially with 5 ml of start buffer (50 mM Tris-HCl, 150 mM NaCl, pH8.0) and 5 ml of elution buffer (100 mM glycine HCl, 150 mM NaCl, pH2.5), and then equibrilated with 10 ml of start buffer. Then, 8 ml of start buffer was added to 2 ml of human serum filtered with MILLEX-GV 0.22 µm Filter Unit (Millipore) and the solution was fed to the column at a flow rate of 100 µl/min, and the column was washed with 10 ml of start buffer. The binding substance was made to elute by 3 ml of elution buffer while the ultraviolet absorption at 230, 280 and 300 nm was monitored, and 100 µl fractions were collected. A 0.9-fold volume of trichloroacetate was added to the obtained peak fraction, and the mixture was left for 30 minutes on ice. The mixture was then centrifuged at 15,000 rpm for 20 minutes, the supernatant was removed. Then, 750 µl of ethanol was added to the precipitate, followed by centrifugation at 15,000 rpm for five minutes. Then the supernatant was removed, and the precipitate was left to be air-dried. The resultant precipitate was separated under a reducing condition by 10% SDS-PAGE, and proteins were transferred to an Immobilon transfer membrane (MILLIPORE). The membrane was gently shaken at room temperature for one hour in PBS/0.1% Tween20/5% skim milk solution. Next, the membrane was incubated in a solution comprising rabbit anti-human soluble RAGE polypeptide polyclonal antibody at 5 µg/ml and PBS/0.1% Tween20/5% skim milk at room temperature for one hour. The membrane was then washed four times for 15 minutes with PBS/0.1% Tween20 solution. Then, the membrane was incubated at room temperature for one hour with a solution comprising HRP conjugated anti-rabbit IgG(H+L) (Zymed) at 1.5 µg/ml and PBS/0.1% Tween20/5% skim milk. The membrane was washed four times with PBS/0.1% Tween20 solution for 15 minutes, and the membrane was then treated with an ECL Western Blotting Detection System (Amersham Pharmacia). The signal was detected on an X-ray film. The result is shown in FIG. 10.

The soluble RAGE polypeptide in human serum was trapped by anti-soluble RAGE monoclonal antibody-conjugated affinity column. It was demonstrated by western blotting that the polypeptide trapped by the affinity column was the human RAGE polypeptide. This finding established that the soluble RAGE polypeptide lacking the C terminal peptide of the RAGE polypeptide actually existed in a human serum.

Example 8

Study on the Neutralizing Effect of the Soluble RAGE Polypeptide Against AGE (Effect of Soluble RAGE Polypeptide on AGE-Induced VEGF Expression)

In this experiment, the inventors used the primary cultures of micro-vasculature endothelial cells from human skin (purchased by Cascade Biologics, Inc., Portland, Oreg. Kurabo, Osaka), which were grown in a flask of 25 cm$^2$ until the cells reached to subconfluent. The cells were washed with freshly prepared Hu-Media MV2 medium (assay medium) containing 5% fetal bovine serum, 5 ng/ml basic fibroblast growth factor, and 10 µg/ml heparin. Then, the medium was exchanged for assay medium (1) without additive, (2) with addition of 10 µg/ml of AGE-BSA, or (3) with addition of 10 µg/ml of AGE-BSA and 25 µg/mol purified soluble RAGE, and the culture was kept warm at 37° C. for four hours. After the treatment, poly(A)$^+$ RNA was isolated from the cells using Quickprep micro mRNA isolation kit (Amersham Pharmacia Biotech). Detection of VEGF mRNA was achieved by using SuperScript One-Step RT-PCR kit (GIBCO BRL). For the amplification of VEGF mRNA, 30 ng of poly(A)$^+$RNA and 30 cycle PCR were used. β-actin was used as an internal standard (30 ng, 20 cycles). RT-PCR products were separated by 3% agarose-gel electrophoresis; gel bands were alkali-transferred to a nylon membrane; and hybridization was achieved by using a $^{32}$P-labeled VEGF specific oligonucleotide probe. The primer and probe used for amplifying VEGF mRNA were the same with those used in Nomura et al., J. Biol. Chem. 1995.

The result is shown in FIG. 11. The expression level of VEGF mRNA in primary cultures of the microvascular endothelial cells from human skin was enhanced about two times by the addition of AGE. However, when the soluble RAGE polypeptide was allowed to coexist with the AGE, the soluble RAGE polypeptide effected in the dominant-negative manner, and suppressed the elevation of VEGF mRNA level due to AGE.

Use of the soluble RAGE polypeptide according to this invention will enable the measurement of native soluble RAGE polypeptide, and thus be useful for diagnosing diseases caused by the interaction of AGE with RAGE, and investigation on the cause, diagnosis and risk prediction of diabetic complications. According to this invention, it is possible to prepare biologically active substances such as monoclonal antibodies to human soluble RAGE polypeptide, to develop novel measurement systems of said protein by using such biologically active substances, so it is useful for predicting risk of development and progress of diabetic complications. Moreover, it is possible to develop compound capable of controlling the production of soluble RAGE polypeptide. It is also useful for diagnosing the metastasis and invasion of a cancer.

The soluble RAGE polypeptide according to this invention is a native polypeptide (intrinsic or endogenous polypeptide) existing in the body, and is different from the RAGE protein in the 16 amino acid residues at the C-terminal. The soluble RAGE polypeptide according to this invention is a native form produced intrinsically, so it is physiologic. Therefore, there is little risk of raising antibody to it. Moreover, if a compound and an agent that controls production of the soluble RAGE capable of oral administration are developed, such a drug would induce expression of the soluble RAGE of this invention. Then, it would enable prevention of diabetic patient from development of the complications without giving pain to the patients. According to this invention, it becomes possible to obtain endogenous soluble RAGE polypeptide or a salt thereof or a variant thereof, modifications, derivatives designed based on basis of these compounds, and to also provide nucleic acids coding for them, vectors containing these nucleic acids, and host cells transformed by these vectors. This invention will be helpful for studies of diseases associated with endogenous soluble RAGE, such as diabetic complications, various diseases accompanied by aging, Alzheimer disease, arteriosclerosis, and diseases caused by glycation of proteins in vivo, or development and/or progress of the diseases and pathological conditions, such as invasion or diffusion of tumors, or symptoms as such, and is expected to give a way for the medicines, the diagnostic agents, as well as genetic diagnosis and gene therapy.

This invention obviously has many applications other than those described in the above explanations and examples. It should be understood that many modifications and variants will be obviously performed, therefore such are also included in the range of the claims attached to this application.

What is claimed is:

1. An isolated soluble polypeptide comprising:
   (a) the amino acid sequence described in SEQ ID NO:2 of the sequence listing; or
   (b) an amino acid sequence having at least 97% homology with the amino acid sequence described in SEQ ID NO:2 of the sequence listing, and comprising from 1 to 16 amino acids of $Glu^{332}$ to $Met^{347}$ of the amino acid sequence described in SEQ ID NO:2 of the sequence listing at the C-terminus;

wherein the soluble polypeptide has Advanced Glycation Endproducts (AGE) binding activity.

* * * * *